(12) United States Patent
Groves, Jr. et al.

(10) Patent No.: US 11,744,671 B2
(45) Date of Patent: *Sep. 5, 2023

(54) SYSTEM AND METHODS FOR PREVENTATIVE DENTAL HARD TISSUE TREATMENT WITH A LASER

(71) Applicant: Convergent Dental, Inc., Needham, MA (US)

(72) Inventors: William Harris Groves, Jr., Arlington, MA (US); Charles H. Dresser, Arlington, MA (US); Nathan P. Monty, Shrewsbury, MA (US); Zhijie Wang, Worcester, MA (US); Christopher Ricci, Brighton, MA (US); Jon Robert Quillard, Carlisle, MA (US)

(73) Assignee: Convergent Dental, Inc., Needham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/806,449

(22) Filed: Mar. 2, 2020

(65) Prior Publication Data
US 2020/0205934 A1 Jul. 2, 2020

Related U.S. Application Data

(63) Continuation of application No. 15/976,272, filed on May 10, 2018.
(Continued)

(51) Int. Cl.
*A61C 1/00* (2006.01)
*A61C 1/05* (2006.01)
(Continued)

(52) U.S. Cl.
CPC ............ *A61C 1/0046* (2013.01); *A61B 18/22* (2013.01); *A61C 1/0015* (2013.01);
(Continued)

(58) Field of Classification Search
CPC ... A61C 1/0046; A61C 1/0015; A61C 1/0061; A61C 1/052; A61C 19/066; A61B 18/22;
(Continued)

(56) References Cited

U.S. PATENT DOCUMENTS 4,273,535 A * 6/1981 Yamamoto ........... A61C 1/0046
433/216
4,877,401 A 10/1989 Higuchi et al.
(Continued)

FOREIGN PATENT DOCUMENTS

CA 2867703 A1 9/2013
EP 2030591 3/2009
(Continued)

OTHER PUBLICATIONS

Correa-Afonso et al, "Influence of Laser Irradiation on Pits and Fissures: An In Situ Study" <https://www.ncbi.nlm.nih.gov/pmc/articles/PMC3565555/ Feb. 2013.
(Continued)

*Primary Examiner* — Nicholas D Lucchesi
*Assistant Examiner* — Hao D Mai
(74) *Attorney, Agent, or Firm* — Goodwin Procter LLP

(57) ABSTRACT

This disclosure relates to various systems and methods related to preventative laser-based treatment of a dental tissue; for example, to prevent a patient from forming cavities. In some instances, a laser-based treatment system can generate a laser beam pulse with a fluence profile at a treatment site that results in either an increase in acid resistance of the tissue or removal of carbonate from the tissue, without melting or ablating the tissue. In some instances, the laser-based treatment system can direct the laser beam to various locations within a treatment site according to a temporal and/or spatial pattern, that results in either an increase in acid resistance of the tissue or removal
(Continued)

of carbonate from the tissue, without melting or ablating the tissue. Many other systems and techniques for preventative and other laser-based treatment are also described.

23 Claims, 42 Drawing Sheets

Related U.S. Application Data

(60) Provisional application No. 62/505,450, filed on May 12, 2017.

(51) Int. Cl.
*A61B 18/22* (2006.01)
*A61N 5/06* (2006.01)
*A61C 19/06* (2006.01)
*H01S 3/02* (2006.01)
*A61N 5/067* (2006.01)

(52) U.S. Cl.
CPC .......... *A61C 19/066* (2013.01); *A61N 5/0603* (2013.01); *A61C 1/0061* (2013.01); *A61C 1/052* (2013.01); *A61N 5/067* (2021.08); *A61N 2005/0606* (2013.01); *H01S 3/02* (2013.01)

(58) Field of Classification Search
CPC .. A61N 5/0603; A61N 2005/0606; H01S 3/02
See application file for complete search history.

(56) References Cited

U.S. PATENT DOCUMENTS

| | | | |
|---|---|---|---|
| 5,374,266 A | 12/1994 | Kataoka et al. | |
| 5,388,987 A | 2/1995 | Badoz et al. | |
| 5,435,724 A | 7/1995 | Goodman et al. | |
| 6,026,828 A * | 2/2000 | Altshuler | A46B 15/0002 132/308 |
| 6,669,685 B1 | 12/2003 | Rizoiu et al. | |
| 7,931,645 B2 | 4/2011 | Strassl et al. | |
| 8,011,923 B2 | 9/2011 | Lukac et al. | |
| 10,045,833 B2 | 8/2018 | Monty et al. | |
| 10,779,908 B2 | 9/2020 | Dresser et al. | |
| 2002/0164291 A1 * | 11/2002 | Cozean | A61K 8/21 433/215 |
| 2003/0170586 A1 | 9/2003 | Cozean et al. | |
| 2004/0248060 A1 | 12/2004 | Cozean et al. | |
| 2005/0255053 A1 | 11/2005 | Cozean et al. | |
| 2007/0160958 A1 | 7/2007 | Belikov et al. | |
| 2008/0280260 A1 * | 11/2008 | Belikov | A61C 3/00 433/215 |
| 2009/0061391 A1 * | 3/2009 | Lukac | A61Q 11/00 433/215 |
| 2011/0032960 A1 * | 2/2011 | Gerlitz | B23K 26/0006 372/29.021 |
| 2011/0076645 A1 | 3/2011 | Torres Zaragoza | |
| 2011/0189628 A1 | 8/2011 | Monty | |
| 2011/0207075 A1 | 8/2011 | Altshuler et al. | |
| 2013/0059264 A1 * | 3/2013 | Monty | A61B 1/24 433/29 |
| 2014/0093843 A1 | 4/2014 | Altshuler et al. | |
| 2015/0147718 A1 | 5/2015 | Khakpour et al. | |
| 2016/0135937 A1 | 5/2016 | Jeng et al. | |
| 2016/0143703 A1 | 5/2016 | Monty et al. | |
| 2017/0319277 A1 | 11/2017 | Cantor-Balan et al. | |
| 2018/0325622 A1 | 11/2018 | Groves, Jr. et al. | |
| 2019/0117333 A1 | 4/2019 | Groves, Jr. et al. | |

FOREIGN PATENT DOCUMENTS

| | | |
|---|---|---|
| JP | 2004049577 A | 2/2004 |
| JP | 2009167135 A | 7/2009 |
| JP | 2016-163749 | 9/2016 |
| WO | WO-2003059305 A1 | 7/2003 |
| WO | WO-2003076015 A1 | 9/2003 |
| WO | WO-2012008599 | 1/2012 |
| WO | WO-2012105972 A1 | 8/2012 |

OTHER PUBLICATIONS

Daniel Nguyen et al., "High-speed scanning ablation of dental hard tissues with a ? =9.3 ?m CO2 laser: adhesion, mechanical strength, heat accumulation, and peripheral thermal damage"; Journal of Biomedical Optics 16 (7), 071410 (Jul. 2011).
Lidiany Azevedo, et al, "Carbon dioxide laser in dental caries prevention", Oct. 2004 <https://www.researchgate.net/publication/ 8407439Carbon_dioxide_laser_in_dental_caries_prevention>.
Marcella Esteves-Oliveira et al, "Screening of CO2 Laser (10.6??m) Parameters for Prevention of Enamel Erosion" Photomedicine and Laser Surgery, vol. 30, Nov. 6, 12, pp. 330-338.
Kwang K. Chang, et al. "Adhesion studies on dental enamel surfaces irradiated by a rapidly scanned carbon dioxide laser", Proc SPIE Int Soc Opt Eng. Jan. 1, 2011; 7884: doi:10,1117/12.878892.
Kenneth H. Chan, et al., "Analysis of enamel surface damage after selective laser ablation of composite from tooth surfaces", Photonics Lasers Med. Feb. 1, 2014; 3(1): 37-45.
Daniel Fried, et al., "Infrared Spectroscopy of Laser Irradiated Dental Hard Tissues Using the Advanced Light Source" Apr. 27, 2001 <http://citeseerx.ist.psu.edu/viewdoc/download?doi=10.1.1. 158.7297&rep=rep1&type=pdf>.
Michael Staninec, et al., "Pulpal Effects of Enamel Ablation With a Microsecond Pulsed ?=9.3–?m CO2 Laser" Lasers Surg Med. Apr. 2009; 41 (4): 256-263.
Shlomo Assa, et al. "Ablation of Dental Hard Tissues With a Microsecond Pulsed Carbon Dioxide Laser Operating at 9.3–?m With An Integrated Scanner" Proc SPIE Int Soc Opt Eng. 2008; 6843:684308. doi:10.1117/12.778799.
Saba Hedayatollahnajafi, et al."Dentin Bond Strength After Ablation Using a Co2 Laser Operating at High Pulse Repetition Rates" Proc SPIE Int Soc Opt Eng. Feb. 18, 2009; 7162:71620F-.doi:1117/ 12.816862.
Saba Hedayatollahnajafi, et al."Relation between Acid Dissolution and Histological Alteration of Heated Tooth Enamel (with 1 color plate)" Proc SPIE Int Soc Opt Eng. Feb. 18, 7162: 71620F-.doi:10. 11/12.816862.
Fowler Bo, et al., "Changes in heated and in laser-irradiated human tooth enamel and their probable effects on solubility" Calcif Tissue Int. Apr. 1986; 38(4):197-208.
Giselle rodrigues de Sant'Anna, et al. "Dental Enamel Irradiated with Infrared Diode Laser and Photo-Absorbing Cream: Part 2-EDX Study" Photomed Laser Surg. Oct. 2009; 27(5): 771-782.
Kenneth H. Chan, et al., "Rapid and Selective Removal of Composite From Tooth Surfaces With a 9.3 μm CO2 Laser Using Spectral Feedback" Lasers Surg Med. Sep. 2011; 43(8): 824-832.
Kenneth H. Chan, et al. "Selective Removal of Demineralization Using Near Infrared Cross Polarization Reflectance and a Carbon Dioxide Laser".
Leon C. Chung, et al, "Image-guided removal of occlusal caries lesions with a ?=9.3-μm CO2 laser using near-IR transillumination" Proc SPIE Int Soc Opt. Eng. Feb. 24, 2015; 9306.
Saman K. Manesh, et al, "Nondestructive assessment of dentin demineralization using polarization sensitive optical coherence tomography after exposure to fluoride and laser irradiation" J. Biomed Mater Res B. Appl Biomater. Aug. 2009; 90(2): 802-812.
Peter Rechmann, et al., :"Caries inhibition in vital teeth using 9.6-?m CO2-laser irradiation" Journal of Biomedical Optics 16 (7), 071405 (Jul. 2011).
JD Featherstone, et al., "CO2 laser inhibitor of artificial caries-like lesion progression in dental enamel" J Dent Res. Jun. 1998;77(6):1397-403.
S.M. McCormack, et. al., "Scanning Electron Microscope Observations of Co2 Laser Effects on Dental Enamel" J Dent Res 74(10): 1702-1708, Oct. 1995.
S.M. McCormack, et. al., "Scanning Electron Microscope Observations of Co2 Laser Effects on Dental Enamel" *J Dent Res* 1995 74: 1702.

(56) References Cited

OTHER PUBLICATIONS

M. Hossain, et al. "Effect of Pulsed Nd:YAG Laser Irradiation on Acid Demineralization of Enamel and Dentin" J Clin Laser Med Surg. Apr. 2001;19(2): 105-8.

D. Fried, et al., "Dissolution Studies of Bovine Dental Enamel Surfaces Modified by High-Speed Scanning Ablation With a Lambda=9.3-Microm Tea CO(2) Laser" Lasers Surg Med. Oct. 2006;38(9):837-45.

S. Tagomori, et al., "Ultrastructural Change of Enamel Exposed to a Normal Pulsed IMd-YAG Laser" Caries Res 1995;29:513-520.

Byung J. Nahm, et al. "Investigation of Acid-Etched CO2 Laser Ablated Enamel Surfaces Using Polarization Sensitive Optical Coherence Tomography" Proc SPIE Int Soc Opt Eng. Feb. 9, 2012; 8208.

Kenneth H. Chan, et al., "Selective Removal of Dental Composite using a Rapidly Scanned Carbon Dioxide Laser" Proc SPIE Int Soc Opt Eng. 2011 ; 7884.

Mozammal Hossain, et al., "Acquired Acid Resistance of Dental Hard Tissues by CO2 Laser Irradiation" Journal of Clinical Laser Medicine & Surgery </journal/pho.1>vol. 17, No. 5 | <https://www.liebertpub.eom/toc/pho.1/17/5>.

J.H. Meurman, et al., "Transformation of Hydroxyapatite to Fluorapatite by Irradiation with High-Energy CO2 Laser" Caries Res 1997;31:397-400.

Daniel Fried, et al., "Multiple-Pulse Irradiation of Dental Hard Tissues at Co2 Laser Wavelengths" Proc. SPIE 2394, Lasers in Dentistry, (May 1, 1995).

Daniel Fried, et al., "Thermal and Chemical Modification of Dentin Ba Pulsed Co2 Laser Irradiation at 9 to 11 Um" Proc. SPIE 2973, Lasers in Dentistry III, (May 15, 1997).

Pinabel Viraparia, et. al., "CO2 Laser: Evidence Based Applications in Dentistry" CO2 Laser—Optimisation and Application, Dr. Dan C. Dumitras (Ed.), ISBN: 978-953-51-0351-6, InTech, Available from: http://www.intechopen.com/books/co2-laser-optimisation-and-application/co2-laserevidence-based-applications-in-dentistry.

Linn H. Maung, et al. "Near-Ir Imaging of Thermal Changes in Enamel During Laser Ablation" Proc SPIE Int Soc Opt Eng. Mar. 5, 2010; 7546(1).

JD Featherstone, "Lasers in Dentistry 3. The Use of Lasers for the Prevention of Dental Caries" Ned Tijdschr Tandheelkd. May 2002;109(5):162-7.

JD Featherstone, et al., "Rational Choice of Laser Conditions for Inhibition of Caries Progression" Proc. SPIE 2394, Lasers in Dentistry, (May 1, 1995).

Joyce Y. Cheng, et al., "Use of a Compact Fiber Optic Spectrometer for Spectral Feedback During the Laser Ablation of Dental Hard Tissues and Restorative Materials" . SPIE 6137, Lasers in Dentistry XII, 61370F (Feb. 13, 2006).

JD Featherstone, et al. "Mechanism of Laser-Induced Solubility Reduction of Dental Enamel" Proc. SPIE 2973, Lasers in Dentistry III, (May 15, 1997).

Michael J. Zuerlein, et al. "Modeling thermal emission in dental enamel induced by 9-11 μm laser light" Applied Surface Science 127:863-868 • May 1998.

JD Featherstone, et al., "Effect of Pulse Duration and Repetition Rate on Co2 Laser Inhibition of Caries Progression" Proc. SPIE 2672, Lasers in Dentistry II, (Apr. 23, 1996).

JD Featherstone, et al., "Surface Dissolution Kinetics of Dental Hard Tissue Irradiated Over a Fluence Range of 1 to 8 J/Cm2" Proc. SPIE 3248, Lasers in Dentistry IV, (Apr. 22, 1998).

Daniel Fried, et al., "Thermal response of hard dental tissues to 9-through 11-μm CO2-laser irradiation" Optical Engineering 35(7), (Jul. 1, 1996). <https://doi.org/10.1117/1.600774>.

International Search Reporting and Written Opinion issued for PCT/US2018/032022, dated Sep. 18, 2018.

Ertl, et al., "Hard Tissue Ablation With Pulsed CO2 Lasers", SPIE vol. 1800 pp. 176-181.

Gerold K.H. Eyrich, "Laser-osteotomy induced changes in bone", Medical Laser Application 20 (2005) 25-36.

M. Frentzen, et al., "Osteotomy with 80 μs CO2 laser pulses—histological results", Lasers Med Sci (2003)18:119-124.

Werner, et al., "CO2 laser free-form processing of hard tissue", Therapeutic Laser Applications and Laser-Tissue Interactions III, Feb. 24, 2010 vol. 6632 663202-1-663202-6.

Ivanenko, et al., Ablation of hard bone tissue with puled CO2 Lasers, Medical Laser Application 20 (2005) 13-23.

G. D. Rajitha Gunaratne, Riaz Khan, Daniel Fick, Brett Robertson, Narendra Dahotre & Charlie Ironside (2016): A review of the physiological and histological effects of laser osteotomy, Journal of Medical Engineering & Technology, DOI: 10.1080/03091902.2016.1199743 (published online Jun. 27, 2016).

Ivanenko, et al., "Hard tissue ablation with sub-μS CO2 laser pulses with the use of air-water spray", Optical Biopsy and Tissue Optics, Proceedings of SPIE vol. 4161 (2000).

Ivanenko, et al., "In Vivo animal trials with a scanning CO2 laser Osteotome," Lasers in Surgery and Medicine 37:144-148 (2005).

Ivanenko, et al., "System development and clinical studies with a scanning CO2 laser osteotome," Optical Interactions with Tissue and Cells XVII, Proc. of SPIE vol. 6084, 60840H, (2006) 1605-7422.

Kahrs, et al., "Planning and simulation of microsugrical laser bone ablation," Int J Cars (2010) 5:155-162 (DOI 10.1007/s11548-009-0303-4).

Kuttenberger, et al., "Bone healing of the sheep tibia shaft after carbon dioxide laser osteotomy; histological results," Lasers Med Sci (2010) 25:239-249 (DOI 10.1007/s10103-009-0714-z).

Nair, et al., "Observations on pulpal response to carbon dioxide laser drilling of dentine in healthy human third molars," Lasers in Medical Science (2005) 19: 240-247 (DOI 10.1007/s10103-004-0317-7).

Werner, et al., "CO2 laser "milling" of hard tissue" Optical Interactions with Tissue and Cells XVIII, Proc. of SPIE vol. 6435, 64350E, (2007) 1605-7422.

Zhang, et al., "Optimization of Line Cut Strategy for Bone tissue ablation using Short-pulsed CO2 laser based on thermal relaxation,".

Kuttenberger, et al., "Computer-Guided CO2-laser osteotomy of the SheepTibia: Technical prerequisites and first resultes," Photomedicine and Laser Surgery, vol. 26, No. 2, 2008, pp. 129-136 (DOI: 10.1089/pho.2007.2139).

Rechmann, P., et al., "In vitro CO2 9.3-mm short-pulsed laser caries prevention—effects of a newly developed laser irradiation pattern", Lasers in Medical Science (2020) 35, 13 pages.

Zhu Y, Zhang X, Chen Y, et al. A comparative study on the dissolution and solubility of hydroxylapatite and fluorapatite at 25° C. and 45° C. Chem Geol. 2009;268(1-2):89-96. doi:10.1016/j.chemgeo.2009.07.014.

Shellis RP, Barbour ME, Jones SB, Addy M. Effects of pH and acid concentration on erosive dissolution of enamel, dentine, and compressed hydroxyapatite. Eur J Oral Sci. 2010;118(5):475-482. doi:10.1111/j.1600-0722.2010.00763.x.

Shellis RP r., Featherstone JDB, Lussi A. Understanding the Chemistry of Dental Erosion. Erosive Tooth Wear From Diagnosis to Ther. 2012;25:163-179. doi:10.1159/000359943.

Shi J, Klocke A, Zhang M, Bismayer U. Thermally-induced structural modification of dental enamel apatite: Decomposition and transformation of carbonate groups. Eur J Mineral. 2005;17(5):769-776. doi:10.1127/0935-1221/2005/0017-0769.

Barinov SM, Rau J V., Cesaro SN, et al. Carbonate release from carbonated hydroxyapatite in the wide temperature rage. J Mater Sci Mater Med. 2006;17(7):597-604. doi:10.1007/s10856-006-9221-y.

Featherstone JDB, Fried D. Fundamental Interactions of Lasers with Dental Hard Tissues. Med Laser Appl. 2001;16(3):181-194. doi:http://dx.doi.org/10.1078/1615-1615-00022.

Kayano T, Ochiai S, Kiyono K, Yamamoto H, Nakajima S, Mochizuki T. [Effects of Er:YAG laser irradiation on human extracted teeth]. Kokubyo Gakkai Zasshi. 1989;56(2):381-392. http://www.ncbi.nlm.nih.gov/pubmed/2794701. Accessed Aug. 28, 2019.

Rechmann P, Fried D, Le CQ, et al. Caries inhibition in vital teeth using 9.6-?m CO2-laser irradiation. J Biomed Opt. 2011;16(7):071405. doi:10.1117/1.3564908.

(56) References Cited

OTHER PUBLICATIONS

Rechmann P, Charland DA, Rechmann BMT, Le CQ, Featherstone JDB. In-vivo occlusal caries prevention by pulsed CO 2 -laser and fluoride varnish treatment—A clinical pilot study. Lasers Surg Med. 2013;45(5):302-310. doi:10.1002/lsm.22141.
González-Rodriguez A, de Dios López-González J, del Castillo J de DL, Villalba-Moreno J. Comparison of effects of diode laser and CO2 laser on human teeth and their usefulness in topical fluoridation. Lasers Med Sci. 2011;26(3):317-324. doi:10.1007/s10103-010-0784-y.
Cohen J, Featherstone JDB, Le CQ, Steinberg D, Feuerstein O. Effects of CO 2 laser irradiation on tooth enamel coated with biofilm. Lasers Surg Med. 2014;46(3):216-223. doi:10.1002/lsm.22218.
Stern RH, Vahl J, Sognnaes RF. Lased Enamel: Ultrastructural Observations of Pulsed Carbon Dioxide Laser Effects. J Dent Res. 1972;51(2):455-460. doi:10.1177/00220345720510023501.
Beeking PO, Herrmann C, Zuhrt R. [Examination of laser-treated tooth surfaces after exposure to acid]. Dtsch Stomatol. 1990;40(12):490-492. http://www.ncbi.nlm.nih.gov/pubmed/2132112. Accessed Aug. 28, 2019.
Steiner-Oliveira C, Nobre-dos-Santos M, Zero DT, Eckert G, Hara AT. Effect of a pulsed CO2 laser and fluoride on the prevention of enamel and dentine erosion. Arch Oral Biol. 2010;55(2):127-133. doi:10.1016/j.archoralbio.2009.11.010.
Ana PA, Bachmann L, Zezell DM. Lasers effects on enamel for caries prevention. Laser Phys. 2006;16(5):865-875. doi:10.1134/S1054660X06050197.
Hossain M, Nakamura Y, Kimura Y, Yamada Y, Ito M, Matsumoto K. Caries-Preventive Effect of Er:YAG Laser Irradiation with or without Water Mist. J Clin Laser Med Surg. 2000;18(2):61-65. doi:10.1089/clm.2000.18.61.
Corrêa-Afonso AM, Bachmann L, De Almeida CG, Corona SAM, Borsatto MC. FTIR and SEM analysis of CO2 laser irradiated human enamel. Arch Oral Biol. 2012;57(9):1153-1158. doi:10.1016/j.archoralbio.2012.02.004.
Zezell DM, Benetti C, Veloso MN, Castro PAA, Ana PA. FTIR spectroscopy revealing the effects of laser and ionizing radiation on biological hard tissues. J Braz Chem Soc. 2015;26(12):2571-2582. doi:10.5935/0103-5053.20150246.
Nelson DGA, Wefel JS, Jongebloed WL, Featherstone JDB. Morphology, Histology and Crystallography of Human Dental Enamel Treated with Pulsed Low-Energy Infrared Laser Radiation. Caries Res. 1987;21(5):411-426. doi:10.1159/000261047.
Featherstone JDB. The science and practice of caries prevention. J Am Dent Assoc. 2000;131(7):887-899. doi:10.14219/jada.archive.2000.0307.
Featherstone JDB, Barrett-Vespone NA, Fried D, Kantorowitz Z, Seka W. CO2 laser inhibition of artificial caries-like lesion progression in dental enamel. J Dent Res. 1998;77(6):1397-1403. doi:10.1177/00220345980770060401.
Esteves-Oliveira M, Pasaporti C, Heussen N, Eduardo CP, Lampert F, Apel C. Rehardening of acid-softened enamel and prevention of enamel softening through CO2 laser irradiation. J Dent. 2011;39(6):414-421. doi:10.1016/j.jdent.2011.03.006.
Rechmann P, Rechmann BMT, Groves WH, et al. Caries inhibition with a CO 2 9.3??m laser: An in vitro study. Lasers Surg Med. 2016;554(February):1-9. doi:10.1002/lsm.22497.
Zuerlein M, Fried D, Featherstone JDB. Modeling the Modification Depth of carbon Dioxide Laser Treated Enamel. Lasers Surg Med. 1999;25(May):335-347.
Argenta RMO, Tabchoury CPM, Cury JA. A modified pH-cycling model to evaluate fluoride effect on enamel demineralization. Pesqui Odontol Bras. 2003;17(3):241-246. doi:10.1590/S1517-74912003000300008.
Stookey GK, Featherstone JDB, Rapozo-Hilo M, et al. The Featherstone laboratory pH cycling model: A prospective, multi-site validation exercise. Am J Dent. 2011;24(5):322-328.
Featherstone JD, ten Cate JM, Shariati M, Arends J. Comparison of artificial caries-like lesions by quantitative microradiography and microhardness profiles. Caries Res. 1983;17(5):385-391. doi:10.1159/000260692.
Bahrololoomi Z, Fotuhi Ardakani F, Sorouri M, Fotuhi Ardakani F. In Vitro Comparison of the Effects of Diode Laser and CO 2 Laser on Topical Fluoride Uptake in Primary Teeth. J Dent. 2015;12(8). www.jdt.tums.ac.ir. Accessed Jul. 24, 2018.
Tepper SA, Zehnder M, Pajarola GF, Schmidlin PR. Increased fluoride uptake and acid resistance by CO 2 laser-irradiation through topically applied fluoride on human enamel in vitro. J Dent. 2004;32(8):635-641. doi:10.1016/j.jdent.2004.06.010.
International Search Report and Written Opinion for PCT/US2020/067656 dated Apr. 21, 2021.

\* cited by examiner

SYSTEM AND METHODS FOR PREVENTATIVE DENTAL HARD TISSUE TREATMENT WITH A LASER

CROSS-REFERENCE TO RELATED APPLICATIONS

This application is a continuation of and claims the benefit of priority to U.S. patent application Ser. No. 15/976,272, titled "System and Methods for Preventative Dental Hard Tissue Treatment with a Laser," filed May 10, 2018, which claims priority to U.S. Provisional Patent Application No. 62/505,450, titled "Systems and Methods for Preventative Dental Hard Tissue Treatment with a Laser," filed May 12, 2017, the disclosures of both of which are incorporated herein by reference in their entireties.

BACKGROUND

Dental caries are caused by bacteria. The bacteria convert sugars, such as glucose, fructose and sucrose, into acids, such as lactic, butyric and acetic. Bacteria-born acid over time breaks down dental hard tissue in a process known as demineralization. Unfortunately, the treatment for dental caries, or cavities, is experientially known by most readers. It is therefore understood by most readers why it is desirable to avoid 'getting cavities.'

Academic research has shown that lasers can be used to render dental hard tissue more resistant to caries formation, and acid dissolution in general. For over twenty years, research on dental enamel has shown that laser treatment reduces the acid dissolution rate. These findings have been corroborated by in vivo and in situ studies. For example, work done by Dr. Peter Rechmann et al. at the University of California San Francisco and published in 2011 found 87% demineralization inhibition over 12 weeks for patients' enamel treated with a 9.6 micron laser. Because of the amount and quality of research related to this topic, the premise: that specific laser treatments inhibit the formation of cavities is now widely considered uncontroversial in the dental research community.

Dental erosion is defined as the acidic dissolution of dental hard tissue by acids not formed by intra-oral bacteria. Primary causes of dental erosion include: acidic beverages and acid reflux. Unlike cavities, the treatment for dental erosion is less widely known. Also unlike cavities, treatment for dental erosion is more likely to impact other aspects of the patient's life. Fluoride treatment may be used to retard dental erosion, but often with mixed results. More effective treatment for dental erosion is usually prescribed lifestyle changes, for example prolonged abstinence from drinking acidic beverages, like soda and juice. Lifestyle changes are difficult for most patients to subscribe to, and are practically impossible for some dental erosion patients. For example, a sommelier suffering from dental erosion from repeatedly holding acidic wine in his mouth cannot make the necessary lifestyle changes to treat his dental erosion without a career change. A dental treatment that retards dental erosion and inhibits cavity formation is therefore desired.

SUMMARY

In one aspect, the invention relates to a system for treating a dental hard tissue to resist acid dissolution. The system can include a laser source for generating at least one pulse of a laser beam; at least one optic in optical communication with the laser source, the at least one optic adapted to define laser beam width and focus the laser beam at or near a surface of the dental hard tissue; and a controller adapted to control pulse energy based on the defined beam width, such that the laser beam pulse has a fluence profile at a focus having a maximum local fluence less than an upper threshold fluence, the upper threshold fluence defined as a minimum fluence that causes a surface modification of the dental hard tissue, and at least one other local fluence greater than a lower threshold fluence, the lower threshold fluence defined as a fluence that causes at least one of (i) a minimum increase in an acid dissolution resistance of the dental hard tissue and (ii) a minimum decrease in an amount of surface carbonate of the dental hard tissue.

In some embodiments of the above aspect, the surface modification includes melting and/or ablation. The melting and/or ablation can be determined by a visual inspection of a treated surface at at least one of 200×, 500×, and 1000× magnification. The acid dissolution resistance can be determined by at least one of an acidic challenge and a pH cycling study. The acidic challenge can include using at least one of citric acid, acetic acid, and lactic acid. In some cases, the amount of surface carbonate can be measured by at least one of reflectance FTIR, FTIR-ATR, Ramen Spectroscopy, and XRD. In some instances, the fluence profile can further include a Gaussian profile, a near-Gaussian profile, and/or a top-hat profile. The laser source can produce a laser beam having a wavelength in a range from 8 to 12 microns. In some instances, the controller is adapted to control a pulse duration, an average laser input power, and/or an average laser output power, to control the pulse energy.

In another aspect, the invention relates to a method of treating a dental hard tissue to resist acid dissolution. The method can include the steps of: generating at least one pulse of a laser beam; defining a laser beam width and focusing the laser beam at or near a surface of the dental hard tissue using at least one optic; and controlling pulse energy based on the defined beam width, such that the laser beam pulse has a fluence profile at a focus having: a maximum local fluence less than an upper threshold fluence, the upper threshold fluence defined as a minimum fluence that causes a surface modification of the dental hard tissue, and at least one other local fluence greater than a lower threshold fluence, the lower threshold fluence defined as a fluence that causes at least one of (i) a minimum increase in an acid dissolution resistance of the dental hard tissue and (ii) a minimum decrease in an amount of surface carbonate of the dental hard tissue.

In some embodiments of the above aspect, the surface modification can include melting and/or ablation. The melting and/or ablation can be determined by a visual inspection of a treated surface at at least one of 200×, 500×, and 1000×. The acid dissolution can be determined by at least one of an acidic challenge and a pH cycling study. The acidic challenge can include using at least one of citric acid, acetic acid, and lactic acid. In some cases, the amount of surface carbonate is measured by at least one of reflectance FTIR, FTIR-ATR, Ramen Spectroscopy, and XRD. The fluence profile can further include a Gaussian profile, a near-Gaussian profile, and/or a top-hat profile. In some instances, the laser beam pulse has a wavelength in a range from 8 to 12 microns. In some cases, controlling the pulse energy can include controlling a pulse duration, average laser input power, and average laser output power. The method can further include applying a post-treatment solution to the dental hard tissue. The post-treatment solution can include hydrogen peroxide, fluoride, chitosan, xylitol, calcium, and/or phosphate.

In another aspect, the invention relates to another system for treating a dental hard tissue to resist acid dissolution. The system can include: a laser source for generating a plurality of pulses of a laser beam; and a beam guidance system adapted to: direct a first laser pulse to an initial location within a treatment region of the dental hard tissue, such that a surface temperature of the initial location is raised from an initial surface temperature to a raised surface temperature during the first laser pulse, the raised temperature being below an upper temperature threshold defined as a minimum temperature that causes a surface modification of the dental hard tissue; direct one or more intermediate laser pulses to one or more intermediate locations within the treatment region; and direct another laser pulse to the initial location (or a neighbor of the initial location), after a cooling-off period during which cooling of the initial location causes a difference between the surface temperature and the initial surface temperature to be less than or equal to 50% of the raised temperature.

In some embodiments of the above aspect, the initial surface temperature is in a range from 20 to 40 degrees Celsius. The raised surface temperature can be in a range from 300 to 1800 degrees Celsius. In some instances, the first laser pulse has a pulse duration in a range from 0.1 to 100 microseconds. In some instances, the first laser pulse has a pulse energy in a range from 0.05 to 100 mJ. The initial location can have a width in a range from 0.1 to 10 millimeters. In some cases, the cooling-off period is at least 500 microseconds. In some instances, the one or more intermediate locations do not overlap the initial location. In some instances, the one or more intermediate locations overlap the initial location by no more than a specified threshold amount, which can be a function of at least one of laser pulse energy and laser beam width. The laser beam can have a wavelength in a range from 8 to 12 microns (e.g., 9 to 10 microns or 10 to 11 microns). In some instances, the raised temperature is at least equal to a lower temperature threshold defined as a temperature that causes at least one of (i) a minimum increase in an acid dissolution resistance of the dental hard tissue and (ii) a minimum decrease in an amount of surface carbonate of the dental hard tissue.

In another aspect, the invention relates to another method of treating a dental hard tissue to resist acid dissolution. The method can include the steps of: directing a first laser pulse to an initial location within a treatment region of the dental hard tissue; raising a surface temperature of the initial location from an initial surface temperature to a raised surface temperature during the first laser pulse, the raised temperature being below an upper temperature threshold defined as a minimum temperature that causes a surface modification of the dental hard tissue; directing one or more intermediate laser pulses to one or more intermediate locations within the treatment region; and directing another laser pulse to the initial location (or a neighbor of the initial location), after a cooling-off period during which cooling of the initial location causes a difference between the surface temperature and the initial surface temperature to be less than or equal to 50% of the raised temperature.

In some embodiments of the above aspect, the initial surface temperature is in a range from 20 to 40 degrees Celsius. The raised surface temperature can be in a range from 300 to 1800 degrees Celsius. In some instances, the first laser pulse has a pulse duration in a range from 0.1 to 100 microseconds. In some instances, the first laser pulse has a pulse energy in a range from 0.05 to 100 mJ. The initial location can have a width in a range from 0.1 to 10 millimeters. In some cases, the cooling-off period is at least 500 microseconds. In some instances, the one or more intermediate locations do not overlap the initial location. In some instances, the one or more intermediate locations overlap the initial location by no more than a specified threshold amount, which can be a function of at least one of laser pulse energy and laser beam width. The laser beam can have a wavelength in a range from 8 to 12 microns (e.g., 9 to 10 microns or 10 to 11 microns). In some instances, the raised temperature is at least equal to a lower temperature threshold defined as a temperature that causes at least one of (i) a minimum increase in an acid dissolution resistance of the dental hard tissue and (ii) a minimum decrease in an amount of surface carbonate of the dental hard tissue. The method can further include applying a post-treatment solution to the dental hard tissue. The post treatment solution can include hydrogen peroxide, fluoride, chitosan, xylitol, calcium, and/or phosphate.

In another aspect, the invention relates to another system for treating a dental hard tissue to resist acid dissolution. The system can include: a laser source for generating a plurality of pulses of a laser beam; at least one optical component adapted to define laser beam width; a controller adapted to control pulse energy based on the defined beam width, such that the laser beam pulse has a fluence profile at a surface of the dental hard tissue, the profile comprising a local fluence at least equal to a lower threshold fluence defined as a fluence that causes at least one of (i) a minimum increase in an acid dissolution resistance of the dental hard tissue and (ii) a minimum decrease in an amount of surface carbonate of the dental hard tissue; and a beam guidance system adapted to direct the plurality of laser beam pulses to respective locations on the dental hard tissue, such that: a first laser beam pulse is directed to a first location, and another laser beam pulse is directed to another location separated from the first location by a spacing based upon the laser beam width.

In some embodiments of the above aspect, the acid dissolution resistance is determined by at least one of an acidic challenge and a pH cycling study. The acidic challenge can include using at least one of citric acid, acetic acid, and lactic acid. In some cases, the amount of surface carbonate is measured by at least one of reflectance FTIR, FTIR-ATR, Ramen Spectroscopy, and XRD. The fluence profile can further include a Gaussian Profile, a near-Gaussian profile, and/or a top-hat profile. The plurality of laser beam pulses can have a wavelength in a range from 8 to 12 microns. In some cases, the controller is adapted to control a pulse duration, average laser input power, and/or average laser output power, to control the pulse energy. In some instances, the spacing can be further based upon a therapeutic fluence width (defined below).

In another aspect, the invention relates to another method of treating dental hard tissue to resist acid dissolution. The method can include the steps of: generating a plurality of pulses of a laser beam; defining a laser beam width using at least one optical component; controlling pulse energy based on the defined beam width, such that the laser beam pulse has a fluence profile at a surface of the dental hard tissue, the profile comprising a local fluence at least equal to a lower threshold fluence defined as a fluence that causes at least one of (i) a minimum increase in an acid dissolution resistance of the dental hard tissue and (ii) a minimum decrease in an amount of surface carbonate of the dental hard tissue; directing a first laser beam pulse to a first location on the dental hard tissue; and directing another laser beam pulse to another location separated from the first location by a spacing based on the laser beam width.

In some embodiments of the above aspect, the acid dissolution resistance is determined by at least one of an acidic challenge and a pH cycling study. The acidic challenge can include using at least one of citric acid, acetic acid, and lactic acid. In some cases, the amount of surface carbonate is measured by at least one of reflectance FTIR, FTIR-ATR, Ramen Spectroscopy, and XRD. The fluence profile can further include a Gaussian Profile, a near-Gaussian profile, and/or a top-hat profile. The plurality of laser beam pulses can have a wavelength in a range from 8 to 12 microns. In some cases, controlling the pulse energy includes controlling a pulse duration, average laser input power, and/or average laser output power. In some instances, the spacing can be further based upon a therapeutic fluence width (defined below). The method can further include applying a post-treatment solution to the dental hard tissue. The post-treatment solution can include hydrogen peroxide, fluoride, chitosan, xylitol, calcium, and/or phosphate.

In another aspect, the invention relates to another system for treating a dental hard tissue to resist acid dissolution. The system can include: a laser source for generating at least one pulse of a laser beam directed toward a location within a treatment region of the dental hard tissue; a controller adapted to control the laser source such that a surface temperature of the location is increased by a temperature increase amount up to a raised temperature during the laser pulse, the raised temperature being below an upper temperature threshold defined as a minimum temperature that causes a surface modification of the dental hard tissue; and a fluid system for directing a fluid to flow at least one of onto and across the dental hard tissue.

In various embodiments, the fluid can include air, nitrogen, water, a liquid, fluoride, and/or a compressible fluid. The system can further include a fluid expansion element. In some cases, the system includes a fluid controller that controls the fluid system such that the fluid is directed at least one of onto and across the dental hard tissue asynchronously or concurrently with the laser pulse. The laser pulse can include a pulse duration in a range from 0.1 to 1000 microseconds. The laser pulse can include a pulse energy in a range from 0.05 to 100 mJ. The laser beam can have a wavelength in a range from 8 to 12 microns (e.g., 9 to 10 microns or 10 to 11 microns). The location can have a width in a range from 0.1 to 10 millimeters. In some cases, the system includes a flow controller to adjust a flow rate of the fluid sufficient to decrease the surface temperature of the location to a lowered temperature while no laser beam pulse is directed toward the location, wherein a sum of the lowered temperature and the temperature increase amount is at most equal to the raised temperature. In some cases, the fluid can include compressed air and the flow rate is in a range from 1 SLPM to 100 SLPM. The fluid system can include a vacuum source adapted to generate a negative pressure differential that causes the fluid to flow across the dental hard tissue.

In another aspect, the invention relates to another method of treating a dental hard tissue to resist acid dissolution. The method can include the steps of: generating from a laser source at least one pulse of a laser beam directed toward a location within a treatment region of the dental hard tissue; controlling the laser source such that a surface temperature of the location is increased by a temperature increase amount up to a raised temperature during the laser pulse, the raised temperature being below an upper temperature threshold defined as a minimum temperature that causes a surface modification of the dental hard tissue; and directing a fluid to flow at least one of onto and across the dental hard tissue.

In various embodiments, the fluid can include air, nitrogen, water, a liquid, fluoride, and/or a compressible fluid. The method can include expanding a compressible fluid prior to directing the fluid upon the dental hard tissue. The directing the fluid step can be performed asynchronous or concurrent with the generating the laser pulse step. The laser pulse can include a pulse duration in a range from 0.1 to 1000 microseconds. The laser pulse can include a pulse energy in a range from 0.05 to 100 mJ. The laser beam can have a wavelength in a range from 8 to 12 microns (e.g., 9 to 10 microns or 10 to 11 microns). The location can have a width in a range from 0.1 to 10 millimeters. The method can further include adjusting a flow rate of the fluid sufficient to decrease the surface temperature of the location to a lowered temperature while no pulse burst is directed toward the location, wherein a sum of the lowered temperature and the temperature increase amount is at most equal to the raised temperature. In some cases, the fluid can include compressed air and the flow rate is in a range from 1 SLPM to 100 SLPM. The method can further include generating a negative pressure differential that causes the fluid to flow across the dental hard tissue. In some cases, the method can further include applying a post-treatment solution to the dental hard tissue. The post-treatment solution can include hydrogen peroxide, fluoride, chitosan, xylitol, calcium, and/or phosphate.

In another aspect, the invention relates to a system for treating a treatment region of a dental hard tissue to resist acid dissolution, where the treatment region has a stained pellicle adhered thereto. The system can include: a laser source for generating at least one pulse of a laser beam directed toward a location in the treatment region; and controller adapted to control the laser source such that a surface temperature of the location is raised during the laser pulse to at least a temperature necessary for removal of at least a portion of the stained pellicle.

In various embodiments, the stain can include erythosine, phloxine, bismarck brown, mucicarmine, and/or a food coloring. In some cases, the controller can be further adapted to raise the surface temperature of the location during the laser pulse above a lower therapeutic threshold temperature defined as a temperature that causes at least one of (i) a minimum increase in an acid dissolution resistance of the dental hard tissue and (ii) a minimum decrease in an amount of surface carbonate of the dental hard tissue. In some cases, the lower therapeutic threshold temperature is greater than 300 degrees Celcius. The laser pulse can include a pulse duration in a range from 0.1 to 100 microseconds. The laser pulse can include a pulse energy in a range from 0.05 to 100 mJ. The location can include a width in a range from 0.1 to 10 millimeters. The laser beam can have a wavelength in a range from 8 to 12 microns (e.g., 9 to 10 microns or 10 to 11 microns). In some instances, the stain includes hydrogen peroxide, fluoride, chitosan, xylitol, calcium, and/or phosphate.

In another aspect, the invention relates to another method of treating a treatment region of a dental hard tissue to resist acid dissolution, where the treatment region includes a stained pellicle adhered to the treatment region. The method can include the steps of: generating from a laser source at least one pulse of a laser beam; directing the laser pulse toward a location in the treatment region; and controlling the laser source such that a surface temperature of the location is raised during the laser pulse to at least a temperature necessary for removal of at least a portion of the stained pellicle.

In various embodiments, the stain can include erythosine, phloxine, bismarck brown, mucicarmine, and/or a food coloring. In some cases, the method can further include raising the surface temperature. The lower therapeutic temperature can be defined as a temperature that causes at least one of (i) a minimum increase in an acid dissolution resistance of the dental hard tissue and (ii) a minimum decrease in an amount of surface carbonate of the dental hard tissue. In some cases, the lower therapeutic threshold temperature is greater than 300 degrees Celcius. The laser pulse can include a pulse duration in a range from 0.1 to 100 microseconds. The laser pulse can include a pulse energy in a range from 0.05 to 100 mJ. The location can include a width in a range from 0.1 to 10 millimeters. The laser beam can have a wavelength in a range from 8 to 12 microns (e.g., 9 to 10 microns or 10 to 11 microns). In some instances, the stain includes hydrogen peroxide, fluoride, chitosan, xylitol, calcium, and/or phosphate. The method can further include applying a post-treatment solution to the dental hard tissue. The post-treatment solution can include hydrogen peroxide, fluoride, chitosan, xylitol, calcium, and/or phosphate.

In another aspect, the invention relates to another system for treating a dental hard tissue to resist acid dissolution. The system can include: a laser source for generating a plurality of pulses of a laser beam; at least one optic in optical communication with the laser source, the at least one optic adapted to focus the laser beam at or near a surface of the dental hard tissue; a laser energy sensor adapted for measuring an energy of at least a portion of the plurality of laser pulses; and a controller adapted to control the laser source in response to the measured energy, such that each one of the plurality of laser beam pulses has a fluence profile at a focus having a maximum local fluence less than an upper threshold fluence, the upper threshold fluence defined as a minimum fluence that causes a surface modification of the dental hard tissue.

In various embodiments, the laser energy sensor can include an indium arsenide sensor, a mercury cadmium telluride sensor, a thermopile, a photodiode, and/or a photodetector. The system can further include a beam pickoff adapted to direct the portion of the plurality of laser pulses toward the laser energy sensor. The beam pickoff can include a reflective neutral density filter, a partially transmissive mirror, and/or a beam combiner. The beam pickoff can be selected based on a damage threshold of the laser energy sensor. In some cases, the controller can be adapted to control a width of the laser beam at focus and tapering of the laser beam according to laser energy per pulse. In some cases, the controller is adapted to control (i) laser power and/or (ii) pulse duration, according to a width of the laser beam at the focus.

In another aspect, the invention relates to another method of treating a dental hard tissue to resist acid dissolution. The method can include the steps of: generating from a laser source a plurality of pulses of a laser beam; focusing the laser beam at or near a surface of the dental hard tissue using at least one optic in optical communication with the laser source; measuring an energy of at least a portion of the plurality of laser beam pulses; and controlling the laser source in response to the measured energy, such that each one of the plurality of laser beam pulses has: a fluence profile at the focus having a maximum local fluence less than an upper threshold fluence, the upper threshold fluence defined as a minimum fluence that causes a surface modification of the dental hard tissue.

In various embodiments, the measured energy can include (i) a portion of energy from each laser beam pulse and/or (ii) substantially all of the energy from each laser beam pulse. The method can include sensing a measured energy of at least a portion of the plurality of laser beam pulses. The method can include picking off a signal portion of energy from the plurality of laser beam pulses, wherein sensing the measured energy of at least a portion of the plurality of laser beam pulses comprises sensing the measured energy of the signal portion of energy. In some cases, the method can include controlling a width of the laser beam at focus; and tapering the laser beam according to laser energy per pulse. In some cases, the method can include controlling (i) laser power and/or (ii) pulse duration, according to a width of the laser beam at focus. In some instances, the method can include applying a post-treatment solution to the dental hard tissue. The post-treatment solution can include hydrogen peroxide, fluoride, chitosan, xylitol, calcium, and/or phosphate.

In another aspect, the invention relates to another system for treating a dental hard tissue to resist acid dissolution. The system can include: a laser source for generating at least one pulse of a laser beam; at least one optic in optical communication with the laser source, the at least one optic adapted to define laser beam width and focus the laser beam at or near a surface of the dental hard tissue; a controller adapted to control pulse energy based on the defined beam width, such that the laser beam pulse has a fluence profile at a focus having a maximum local fluence less than an upper threshold fluence, the upper threshold fluence defined as a minimum fluence that causes a surface modification of the dental hard tissue; and a post-treatment delivery system adapted to apply a post-treatment solution to the dental hard tissue. In various embodiments, the post-treatment solution can include hydrogen peroxide, fluoride, chitosan, xylitol, calcium, and/or phosphate. In some instances, the controller is adapted to control a pulse duration, average laser input power, and/or average laser output power, to control the pulse energy.

In another aspect, the invention relates to another method of treating dental hard tissue to resist acid dissolution. The method can include the steps of: generating at least one pulse of a laser beam; defining laser beam width and focusing the laser beam at or near a surface of the dental hard tissue using at least one optic; controlling pulse energy based on the defined beam width, such that the laser beam pulse has a fluence profile at a focus having a maximum local fluence less than an upper threshold fluence, the upper threshold fluence defined as a minimum fluence that causes a surface modification of the dental hard tissue; and delivering a post-treatment solution to the dental hard tissue. In various embodiments, the post-treatment solution can include hydrogen peroxide, fluoride, chitosan, xylitol, calcium, and/or phosphate. In some instances, controlling the pulse energy includes controlling a pulse duration, average laser input power, and/or average laser output power.

DETAILED DESCRIPTION

Definition of Problems to be Solved

Figure 1:
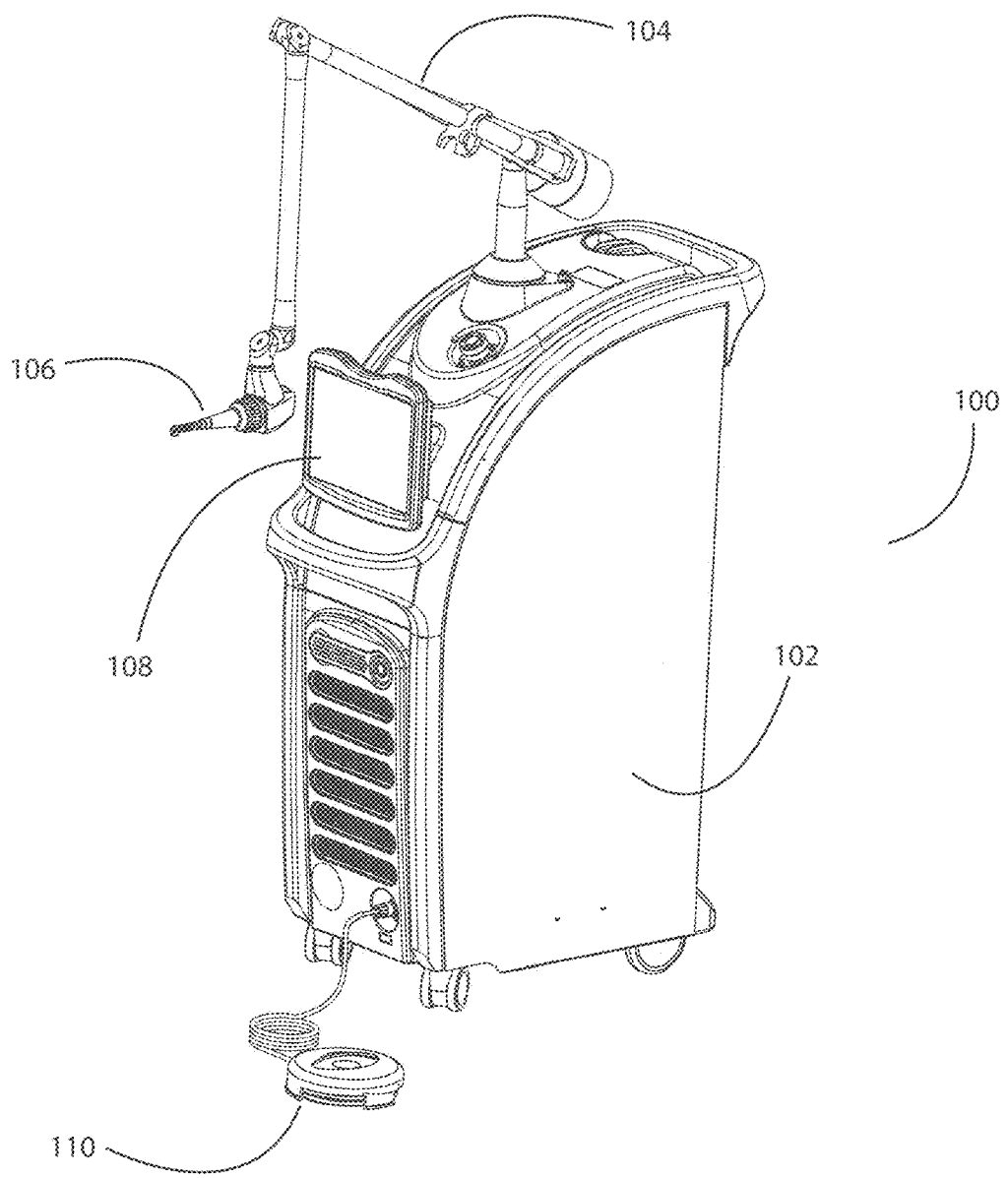
FIG. 1 shows a dental laser system suitable for acid dissolution resistance (ADR) treatment, according to some embodiments.

Currently in spite of twenty plus years of scientific research demonstrating the efficacy of preventative laser treatment, no product or procedure exists that makes use of a laser to inhibit caries-formation or dental erosion. The reasons for this are manifold, and include:

1.) Laser Size

The most useful lasers for preventative dental treatment are carbon dioxide or TEA lasers, which are typically large. Dental operatories are typically small. Some are too small to physically house the lasers used in much of the early research, even without a patient, a dentist, and a dental-assistant in the room.

2.) Therapeutic Range

The heating of the surface must produce surface temperatures generally within a therapeutic range being above a lower treatment threshold, and below an upper melting/ablation threshold to be effective. This specification sometimes uses the term "surface modification" to describe melting and/or ablation of the dental tissue; for example, if the treatment parameters result in the upper melting/ablation threshold being exceeded. As used in this specification, surface modification does not refer to any observable or measurable modification of the surface of a dental tissue;

rather it only refers to melting and/or ablation of the dental tissue. For example, removal of carbonate from the surface of a dental tissue may be observable or measurable, but it would not be considered a "surface modification," as that term is defined in this specification unless the dental tissue was either melted or ablated.

Typically, carbon dioxide lasers produce a laser beam having a Gaussian or near-Gaussian energy profile. The result of which is that the energy density within the laser beam varies over the cross-section of the beam, the highest energy density being at the center of the beam. And, the lowest energy density is at the periphery of the beam. This is why it is possible for a single laser pulse to have energy densities (local fluences) which are below, within, and above the therapeutic range. Much research has focused on the "[global] fluence" required for treatment. Global fluence is total beam area divided my total pulse energy. The non-constant energy density of the laser beam produces variable heating on the surface of the tooth, causing less effective treatments and/or surface melting/ablation (i.e., a surface modification, as defined in this specification). This is generally why, research papers on the acid resistant effects of lasers on dental enamel, which include microscope images of the treated surface will show some degree of tooth surface melting or ablation.

3.) Treatment Speed

The treatment heats the outer surface of the tooth. This heating requires treatment times longer than a typical dentist visit, in order to prevent overheating and necrosis of the pulpal tissue within the tooth. For example, a paper titled "Rational choice of laser conditions for inhibition of caries progression" authored by John Featherstone et al. suggests that repetition rates of about 10 Hz should be selected to prevent pulpal heating. Featherstone goes on to suggest "that a minimum of 10 pulses should be used for each treatment [location]," and that "25 pulses was the optimum." Treatment of a single location of the tooth, which can be less than 1 mm in diameter, will therefore take between 1 to 2.5 seconds. Approximating a human molar's surface area from a five-sided box of dimensions 10 mm by 10 mm by 5 mm yields a surface area of about 300 mm$^2$. A laser treatment spot 1 mm in diameter has an area of about 0.8 mm$^2$. Ignoring the circle packing problem associated with treating an entire surface with circular treatment spots, and assuming no overlap of treatment spots requires about 375 treatment locations per molar. At a rate of 1 to 2.5 seconds per location completely treating a single fully exposed molar, would take between 6 to 16 minutes. Treating all of the exposed enamel surfaces in a patient's mouth, or even just the occlusal surfaces, is therefore not feasible during a regular dental visit given these laser settings.

4.) Indication of Laser Treatment

The laser treatment makes no visible changes to the surface of a treated tooth. Therefore a clinician is ill-equipped to recognize what regions have been treated and what regions have not been treated. As the laser treatment is localized to regions irradiated by the laser beam, any locations that have not been irradiated by the laser beam will remain untreated and will be susceptible to acid. Ensuring that a procedure will be effective is an important requirement of a medical procedure and a medical device. Without a means of differentiating treated from untreated dental hard tissue, it is not possible to ensure that every treatment will be effective.

A laser-based treatment system and method that addresses the above-mentioned problems is therefore needed to more effectively treat dental erosion and prevent dental caries. A laser-based treatment system and method that addresses these problems is described below.

Laser Parameter Selection

Problems No. 1.) LASER SIZE and No. 2.) THERAPEUTIC RANGE above are largely addressed through an appropriate selection of laser parameters.

Referring to FIG. 1, an exemplary dental laser system, 100, such as a Solea from Convergent Dental of Needham, Mass., is shown. In some embodiments, the dental laser system, 100, may ablate dental hard tissues, like enamel, dentin and bone, as well as dental soft tissues at a clinically viable rate. For example, the Solea is FDA approved for cavity preparations, as well as procedures requiring the ablation of soft and osseous tissue. The dental laser system, 100, comprises: a cart, 102, which houses a laser (not shown). An articulated arm, 104, internally directs a laser beam from the cart, 102, to a hand piece, 106. During treatment, the laser beam is further directed out a distal end of the hand piece, 106, and toward dental tissue. The clinician may interface with the dental laser system, 100, through a touch screen, 108, and a foot pedal, 110. In some embodiments the dental laser system, 100, comprises an isotopic carbon dioxide laser (Coherent E-150i) that has a specified maximum average power of about 150 Watts and has a wavelength of about 9.35 micron. This laser in this package size has been proven in the market to be sized appropriately for dental operatories. Nevertheless, it is likely still advantageous for a preventative laser treatment to be housed in a smaller package for use in hygienist operatories.

Figure 2:
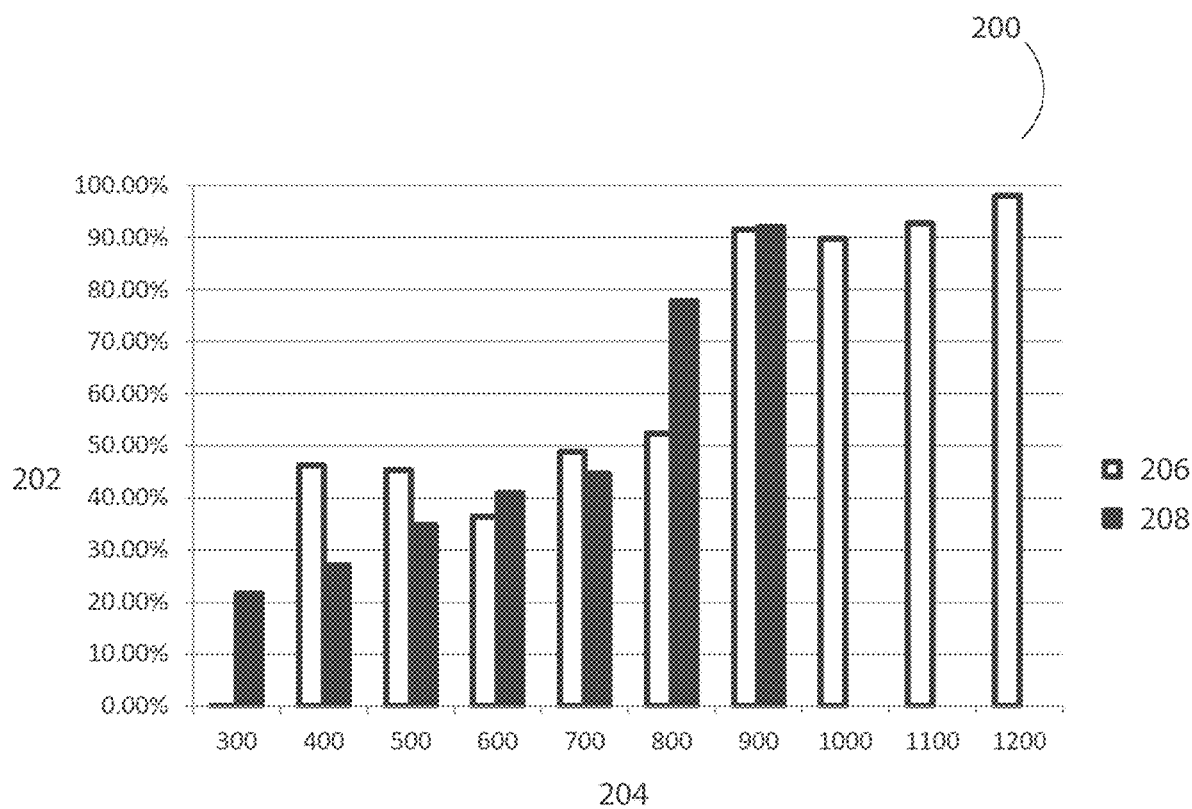
FIG. 2 graphs the effects of temperature on carbonate content of human dental enamel.

Featherstone et al. concluded in his paper titled "Mechanism of Laser Induced Solubility Reduction of Dental Enamel" that "the [laser] fluences that caused complete carbonate loss from the surface coincided with optimum caries inhibition." It has been repeatedly found that removal of carbonate (typically measured by FTIR) from enamel correlates with the enamel having an increased resistance to acid. A widely held theory posits that: it is the lack of carbonate (which is known to be especially soluble in acid) that makes the carbonate-reduced enamel surface more resistant. Carbonate is removed from dental hard tissue through heating. Referring to FIG. 2, carbonate was measured (by FTIR-ATR) in ground human molar before and after it was placed within a furnace and heated. A graph, 200, shows carbonate removed in percent along a vertical axis, 202, and furnace temperature in degrees Celsius along a horizontal axis, 204. A first test. 206, and a second test, 208, are both included in the graph, 200. The results show in the graph, 200, corroborates earlier research showing that enamel begins carbonate loss at about 300° C. or 400° C., and loses nearly all carbonate at temperatures in excess of about 800° C. or 900° C.

In order to better understand how a laser pulse heats dental enamel, a mathematical model has been created, which models the temperature of dental enamel as it undergoes heating from a laser pulse. The model is intended to exhaustively describe all the significant temperature related phenomena occurring within the enamel during the laser pulse. The model was derived from first principles including: Beer's law of absorption, Newton's law of cooling, and Fourier's law of conduction. The model further assumes the laser to have a Gaussian energy profile, and constant peak power during the pulse. Coefficients related to absorbance, reflectivity, etc. were taken from the most recent sources. The model can be run on Matlab R2016a which is included as Appendix A to U.S. Provisional Patent Application No. 62/505,450, which is incorporated by reference herein in its entirety. FIGS. 3A, 4A, 5, 6A, and 7A illustrate results of the model. FIGS. 3B, 4B, 6B, and 7B are FTIR absorbance charts indicating carbonate removed from laser settings based upon modeled results.

Figure 3A:
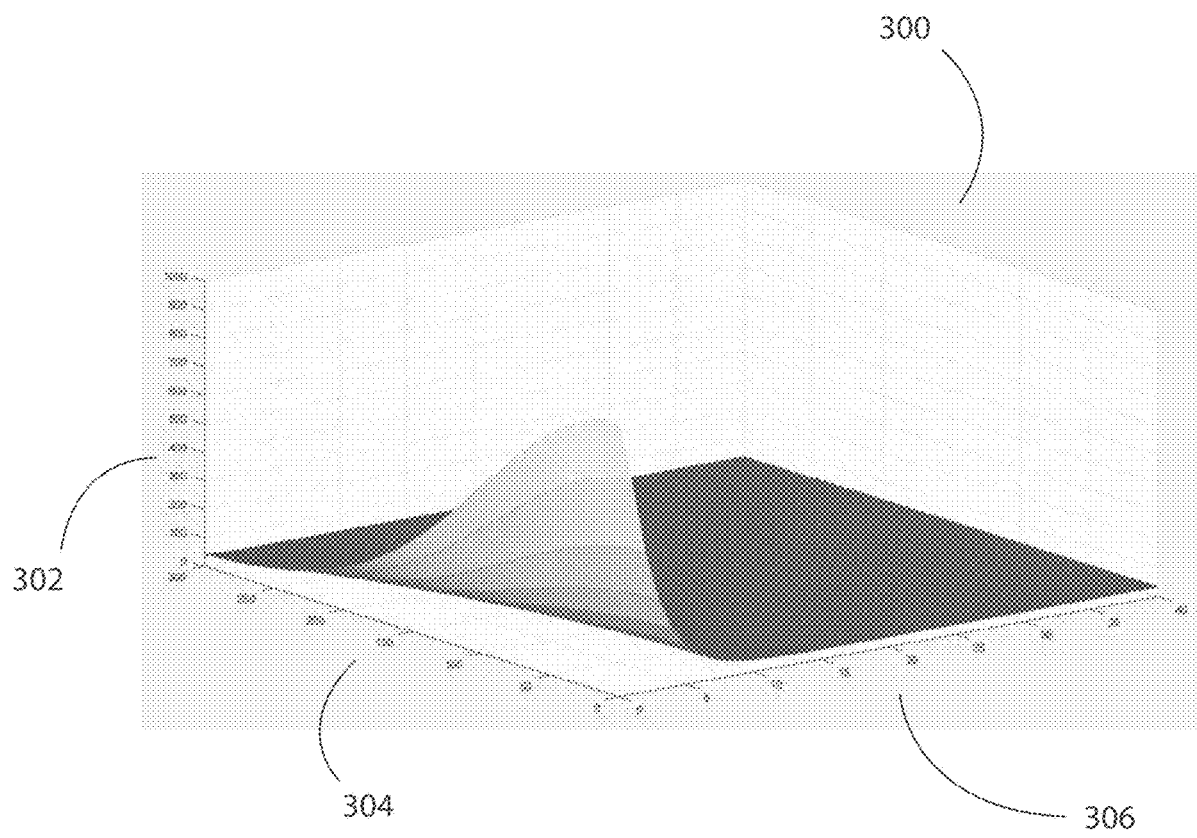
FIG. 3A illustrates modeled temperature results for a human molar undergoing a laser pulse, according to some embodiments.
Figure 3B:
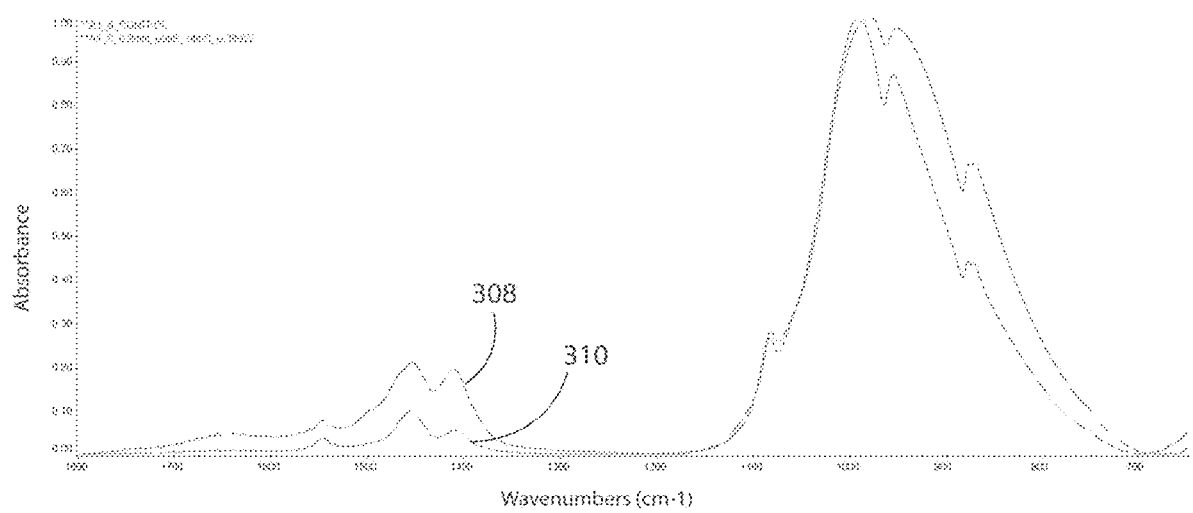
FIG. 3B illustrates measured carbonate content of enamel treated by laser parameters, according to some embodiments.

The usefulness of the model was verified by comparing the enamel temperature predicted by the model at various laser parameters, and the carbonate content of enamel samples after undergoing treatment at these laser parameters with a Coherent E-150i. Specifically, laser parameters of: a 9.35 micron wavelength, a 1 microsecond pulse duration, a peak power of 500 W, and a $1/e^2$ beam diameter at focus of 0.39 millimeters was found empirically to reliably produce more than 40% carbonate removal with little-to-no surface melt. A plot, 300, detailing results from the model for a single laser pulse at these parameters is shown in FIG. 3A. Referring to FIG. 3A, a vertical Temperature axis, 302, represents temperature in degrees Celsius, a Radial axis, 304, directed from the upper-left to the bottom-right represents distance away from a center of a Gaussian laser beam, and a Depth axis, 306, directed from the lower-left to the upper-right represents depth into the enamel. It can be seen from FIG. 3A that the highest temperature occurs at the center of the laser beam, and at the surface of the enamel. Temperature decreases radially from the center of the laser beam according to the Gaussian energy profile of the laser beam. Temperature also decreases with greater depth into the enamel. The model reports: a peak surface temperature of 958 degrees Celsius, an average surface temperature over the irradiated surface of 591 degrees Celsius, and a maximum depth at a temperature greater than 400 degrees Celsius of 3 micron. Referring back to FIG. 2, it can be seen that at about 600 degrees Celsius the amount of Carbonate removed in the furnace is about 40%. FIG. 3B shows spectra for control enamel prior to treatment, 308, and enamel that has undergone treatment, 310, with the following parameters: a 9.35 micron wavelength, a 19 location scanned pattern with 0.2 mm between adjacent locations, a 1.6 microsecond pulse duration, and a 0.39 mm beam width. Carbonate appears in the FTIR absorbance charts as two peaks between 1500 $cm^{-1}$ and 1400 $cm^{-1}$. A larger peak at about 1000 $cm^{-1}$ is used as a reference in a calculation for carbonate removal. The calculation for carbonate removal is shown below:

$$\%_{Removed} = 1 - \frac{\frac{A_{carb,treat}}{A_{ref,treat}}}{\frac{A_{carb,ctrl}}{A_{ref,ctrl}}}$$

Or simplified (assuming that carbonate is always removed not added), $$\%_{Removed} = \frac{A_{ref,treat} A_{carb,ctrl}}{A_{carb,treat} A_{ref,ctrl}}$$

Where $A_{carb,treat}$ is the area under the carbonate peaks for a treated sample, $A_{ref,treat}$ is the area under the reference peak for the treated sample, $A_{carb,ctrl}$ is the area under the carbonate peaks for an untreated sample, and $A_{ref,ctrl}$ is the area under the reference peak for the untreated sample. Referring to FIG. 3B, approximately 60% of the carbonate has been removed from, and no surface melt was observed. It is possible to predict approximately using this model what parameters are needed to produce similar results with different lasers or laser parameters.

Figure 4A:
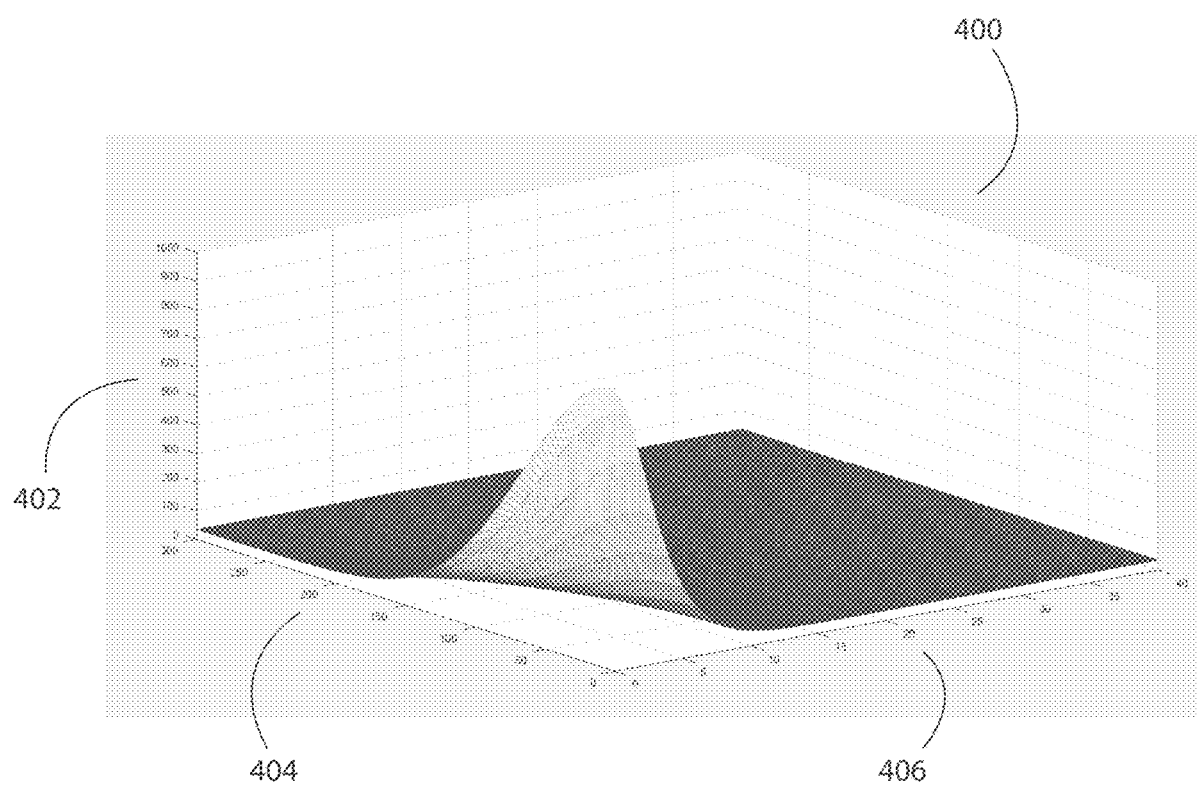
FIG. 4A illustrates modeled temperature results for a human molar undergoing a laser pulse, according to some embodiments.
Figure 4B:
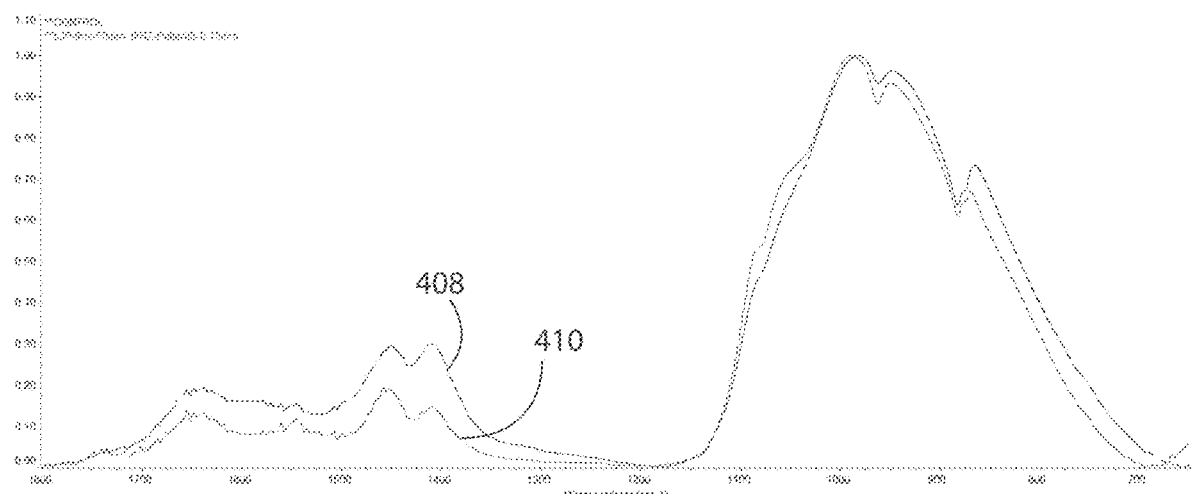
FIG. 4B illustrates measured carbonate content of enamel treated by laser parameters, according to some embodiments.
Figure 5:
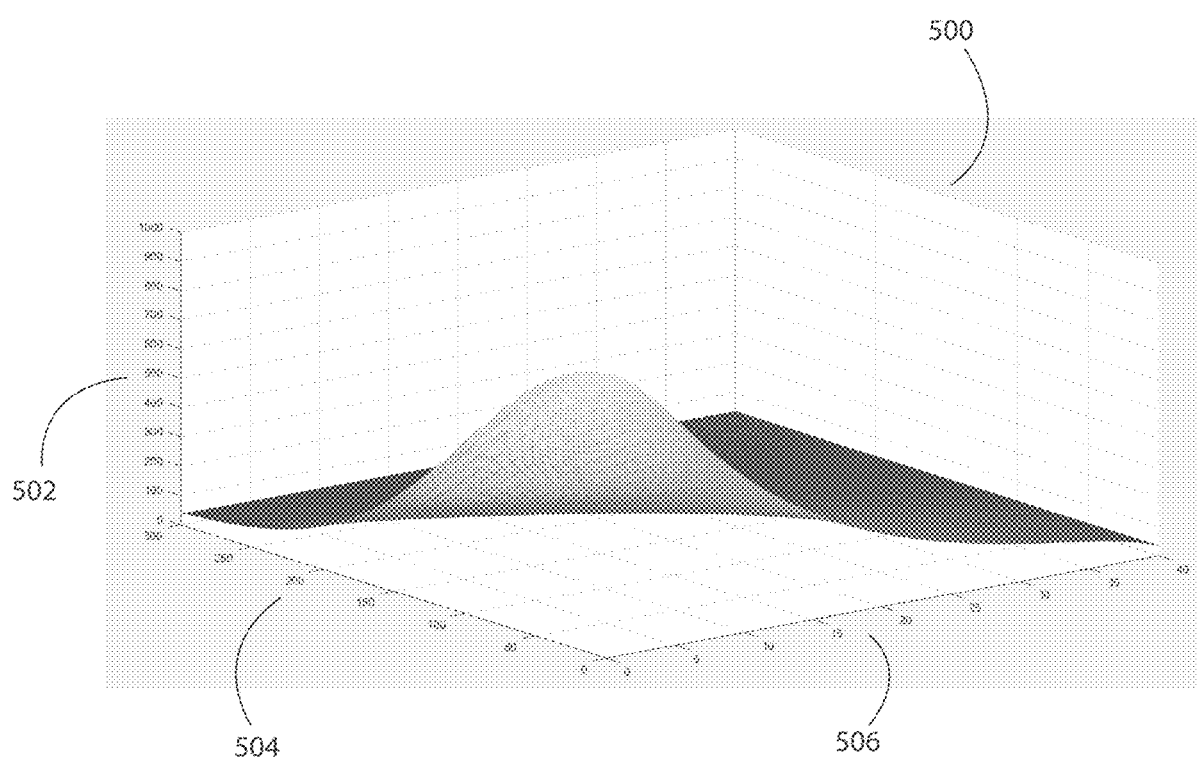
FIG. 5 illustrates modeled temperature results for a human molar undergoing a laser pulse, according to some embodiments.

A Coherent C30 $CO_2$ laser is much smaller than the E-150i and has: a wavelength of 9.35 micron, and a peak power of about 35 W. The C30 laser may be housed in a table-top package, thus limiting the space it occupies in a dental operatory. Prior to modeling it was not immediately recognizable that a laser as small as the C30 could be reliably used for preventative treatment. The mathematical model was used to determine laser parameters that produce a similar modeled result as the Coherent E-150i above. Referring to FIG. 4A, the model predicts a 9 microsecond pulse width and a 0.26 $l/e^2$ beam diameter to produce: a peak surface temperature of 983 degrees Celsius, an average surface temperature within the beam diameter of 606 degrees Celsius, and a maximum depth having a temperature greater than 400 degrees Celsius of 4 micron. A plot, 400, having a Temperature axis, 402, a Radial axis, 404, and a Depth axis, 406 is shown in FIG. 4A. In order to demonstrate the usefulness of the C30, a 49-location scanned laser pattern was developed in response to the above modeled results. The 49 locations are arranged in a hexagonal packing arrangement and adjacent locations are separated by 0.15 mm. Scanned laser patterns are further explained below. Using the C30 laser, with the pattern described above, a 9 microsecond pulse duration, and a 0.26 beam width resulted in about 50% of the carbonate being removed from a Bovine enamel sample, FTIR spectra of the Bovine enamel sample untreated, 408, and treated, 410, are shown in FIG. 4B.

According to some embodiments a $CO_2$ laser having a wavelength of about 10.6 micron is used. Again the mathematical model is used to guide parameter selection, and predict performance. A 10.6 micron laser having a peak power of 100 W, such as a Coherent C50, is modeled and results are plotted in FIG. 5. A plot, 500, has a Temperature axis, 502, a Radial axis, 504, and a Depth axis, 504. A beam width of 0.39 mm, and a pulse duration of 20 microseconds results in: a peak surface temperature of 966 degrees Celsius, an average surface temperature within the beam diameter of 595 degrees Celsius, and a maximum depth having a temperature greater than 400 degrees Celsius of 14 micron. It should be noted that the 10.6 micron laser penetrates deeper into enamel, and therefore requires more energy to treat the same surface area. Total energy delivered into the tooth is estimated at 2 mJ per pulse. A 9.35 micron wavelength E-150i having the same beam width, and parameters resulting in similar surface temperatures delivers only an estimated 0.4 mJ per pulse. However, the E-150i only treats to a depth of about 3 micron, as the 10.6 micron wavelength laser treats to a depth of about 14 micron.

Figure 6A:
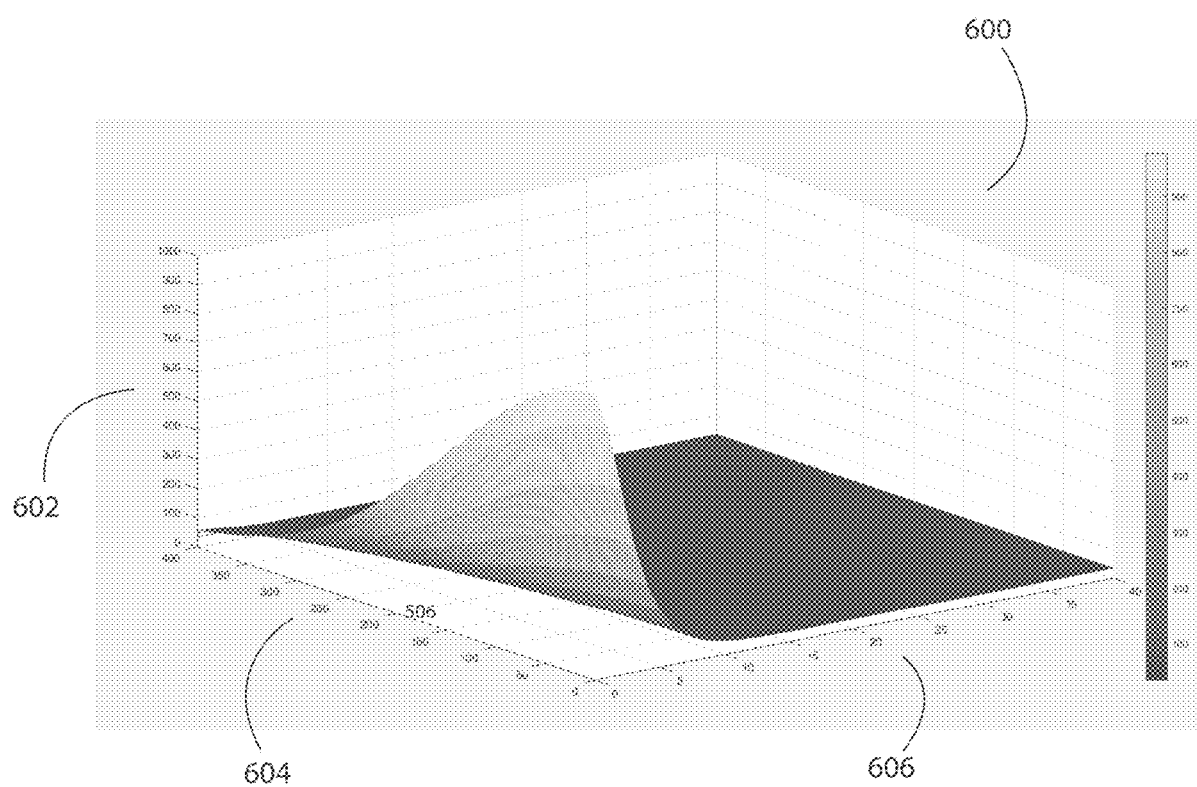
FIG. 6A illustrates modeled temperature results for a human molar undergoing a laser pulse, according to some embodiments.
Figure 6B:
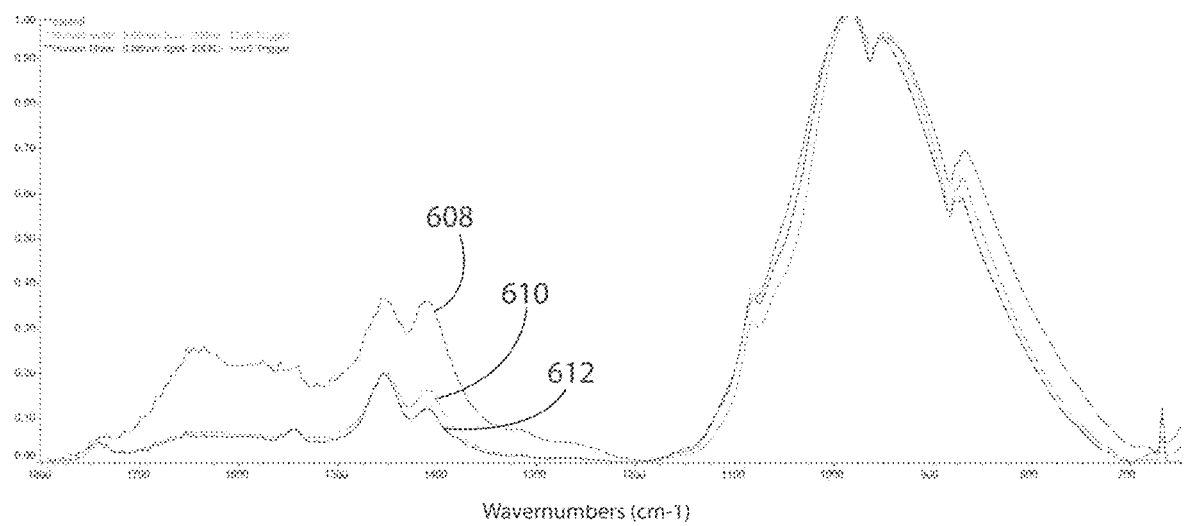
FIG. 6B illustrates measured carbonate content of enamel treated by laser parameters, according to some embodiments.

Returning again to the E-150i laser, some embodiments require the E-150i to be pulsed at pulse durations greater than 5 microseconds. Assuming the peak power of the E-150i to be 300 W at 5 microseconds, a 0.6 mm beam width produces modeled results of: a peak surface temperature of 976 degrees Celsius, an average surface temperature within the beam width of 600 degrees Celsius, and a maximum depth with a temperature greater than 400 degrees Celsius of 4 micron. A plot, 600, of the modeled results of these parameters are shown in FIG. 6A. The plot, 600, includes a Temperature axis, 602, a Radial axis, 604, and a Depth axis, 606. An E-150i producing laser pulses having a 0.66 mm beam width, and a 4.6 and 6.6 microsecond pulse durations was used to treat bovine enamel. The 0.66 mm beam width is large enough that the laser beam was not scanned in a pattern, instead laser pulses were directed at a single location. Approximately 41% of the carbonate in the enamel was removed using the 4.6 microsecond pulse durations, and approximately 50% of the carbonate in the enamel was removed using the 6.6 microsecond pulse durations. FIG. 6B shows FTIR spectra for untreated bovine enamel, 608, bovine enamel treated with a 4.6 microsecond pulse, 610, and bovine enamel treated with a 6.6 microsecond pulse, 612.

Figure 7A:
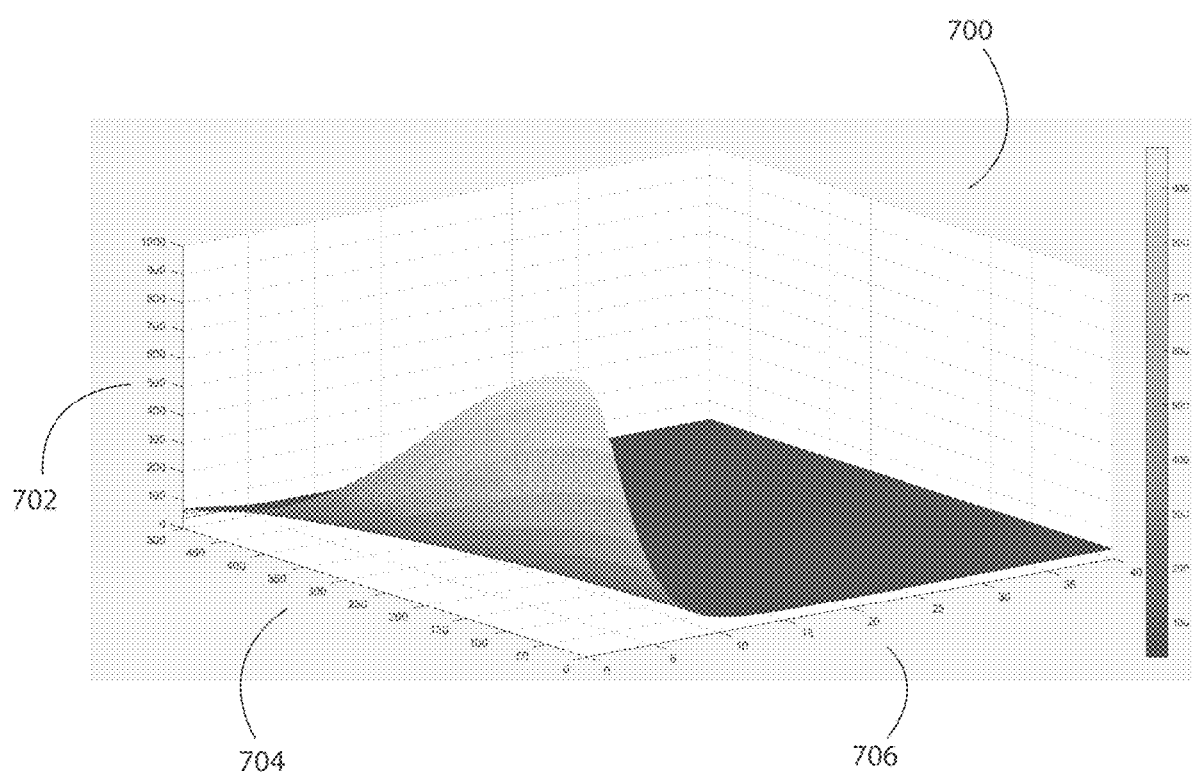
FIG. 7A illustrates modeled temperature results for a human molar undergoing a laser pulse, according to some embodiments.

In some embodiments, parameters are modified to allow the E-150i to pulse at laser pulses having a pulse duration of 10 microseconds. For example, operating the E-150i at a pulse duration of approximately 10 microseconds, results in a peak power of about 300 W. According to the mathematical model a spot size of around 0.79 mm results in: a peak surface temperature of 974 degrees Celsius, an average surface temperature within the beam width of 598 degrees Celsius, and a maximum depth with a temperature greater than 400 degrees Celsius of 4 micron. FIG. 7A illustrates a plot, 700, having a Temperature axis, 702, a Radial axis, 704, and a Depth axis, 706.

Figure 7B:
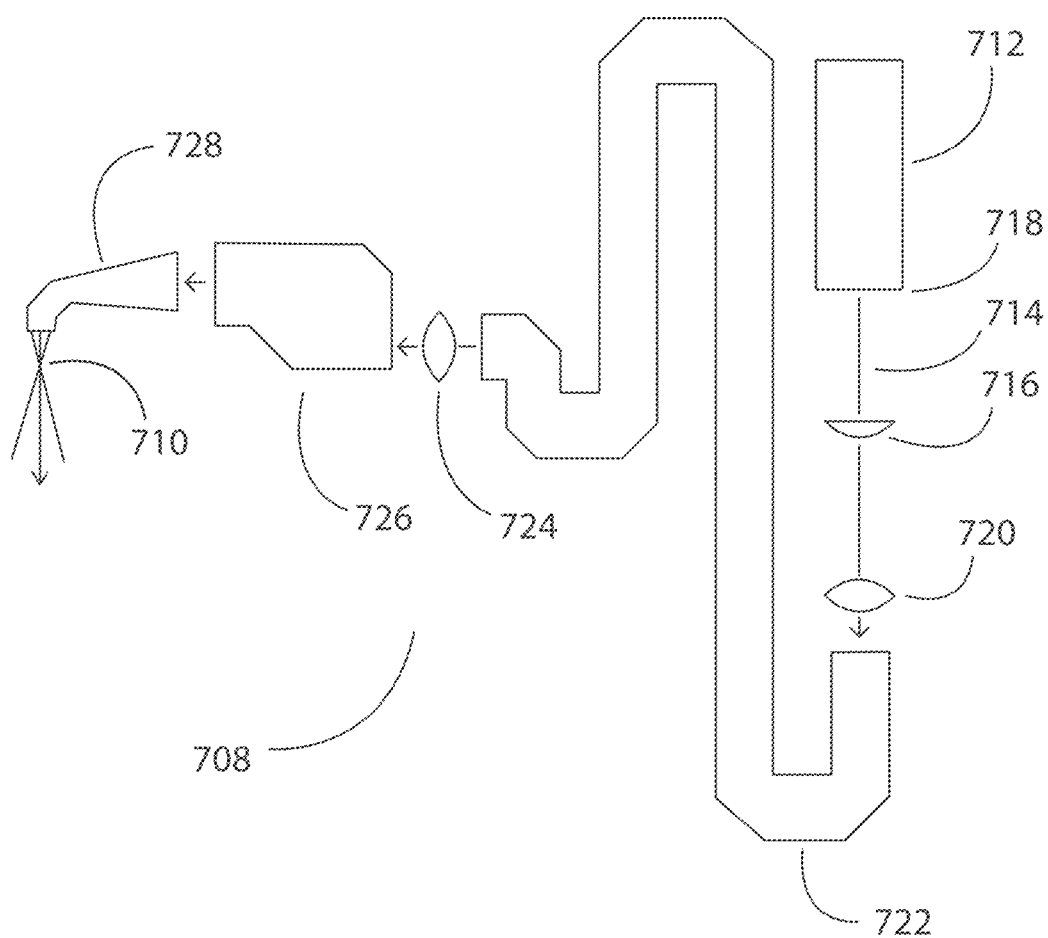
FIG. 7B illustrates an optical system for acid dissolution resistance (ADR) according to some embodiment.

An optical system, 708, used to produce a focus, 710, having a $1/e^2$ width of between 0.65 mm and 0.85 mm is shown in FIG. 7B. Beginning in the top-right corner of the sheet, a laser source, 712, (e.g. Coherent E-150i) generates a laser, 714. A correction optic, 716, corrects the divergence of one axis of the laser, 713. An exemplary correction optic, 716, is a ZnS plano-convex cylinder lens having a radius of curvature of 544.18 mm and is located 160 mm from a distal face, 718, of the laser source, 712. A collimation optic, 720, may be used to slowly focus the laser, 714. An exemplary collimation optic, 720, is a ZnS plano-convex lens having a curvature of about 460 mm and is located about 438 mm from the distal face, 718, of the laser source, 712. In some embodiments, an articulating arm, 722, is used to direct the laser, 714. A focus optic, 724, is located after the articulating arm, 722. In some embodiments, the focus optic, 724, is a ZnSe plano-convex lens having a radius of curvature of about 280.5 mm (e.g. Thorlabs Part No. LA7228-G) located about 1802 mm from the distal face, 718, of the laser source, 712. In some embodiments, a beam guidance system, 726, such as two axis galvanometers are located down beam of the focus optic, 724. A hand piece, 728, is located after the focus optic, 724, as well, and directs the laser, 714, toward a treatment region. In some embodiments, the focus, 710, is located about 240 mm from the focus optic, 724, and about 15 mm outside of the hand piece, 728.

Figure 7C:
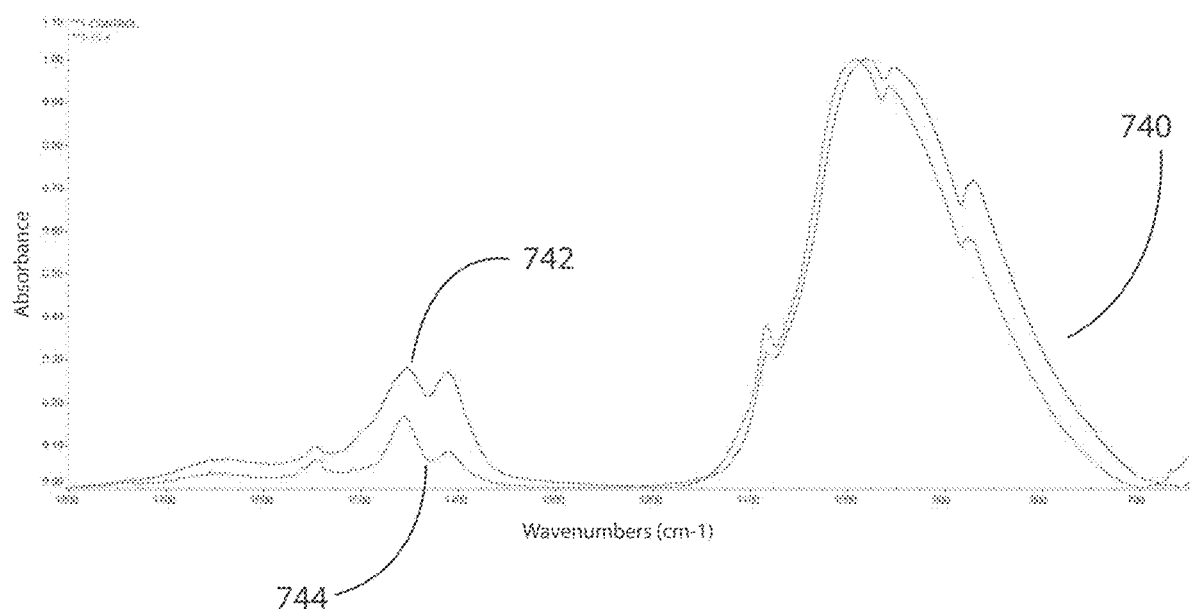
FIG. 7C illustrates measured carbonate content of enamel treated by laser parameters, according to some embodiments.
Figure 7D:
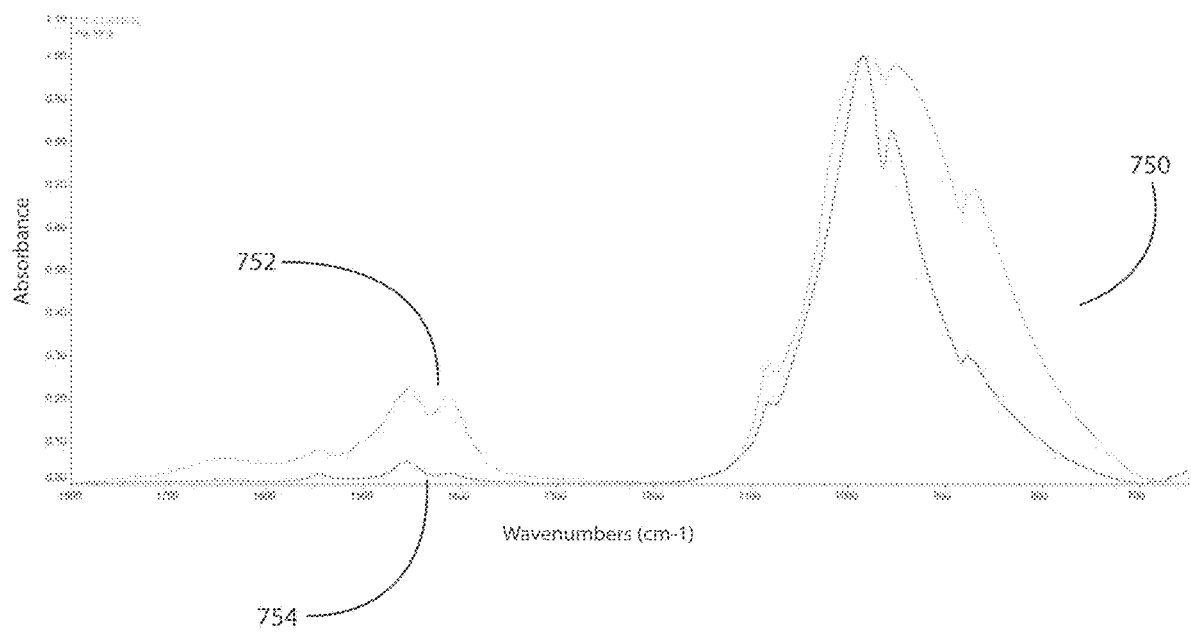
FIG. 7D illustrates measured carbonate content of enamel treated by laser parameters, according to some embodiments.
Figure 7E:
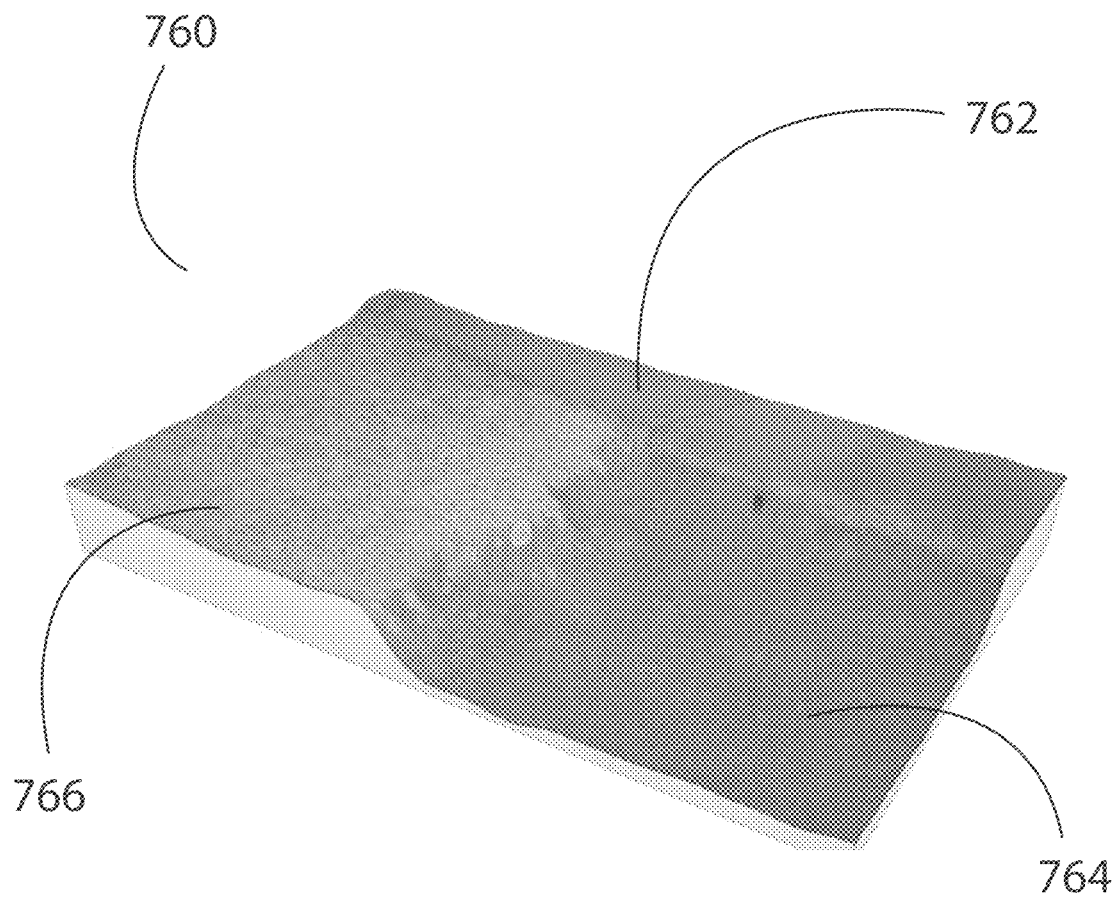
FIG. 7E illustrates an ADR laser treated human molar after undergoing an erosive challenge, according to some embodiments.
Figure 7F:
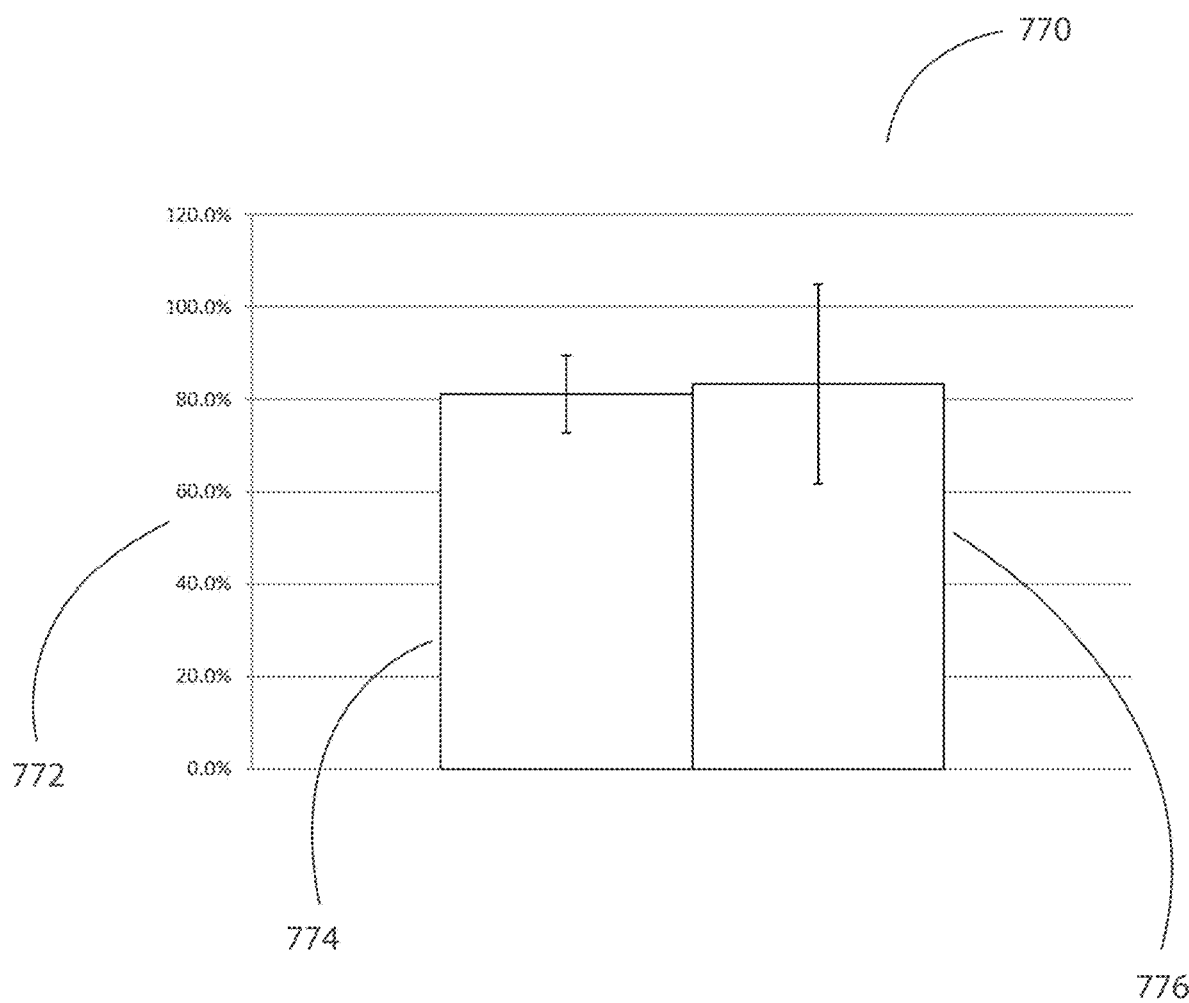
FIG. 7F comprises a graph that shows acid dissolution resistance for laser treatments according to some embodiments.
Figure 7G:
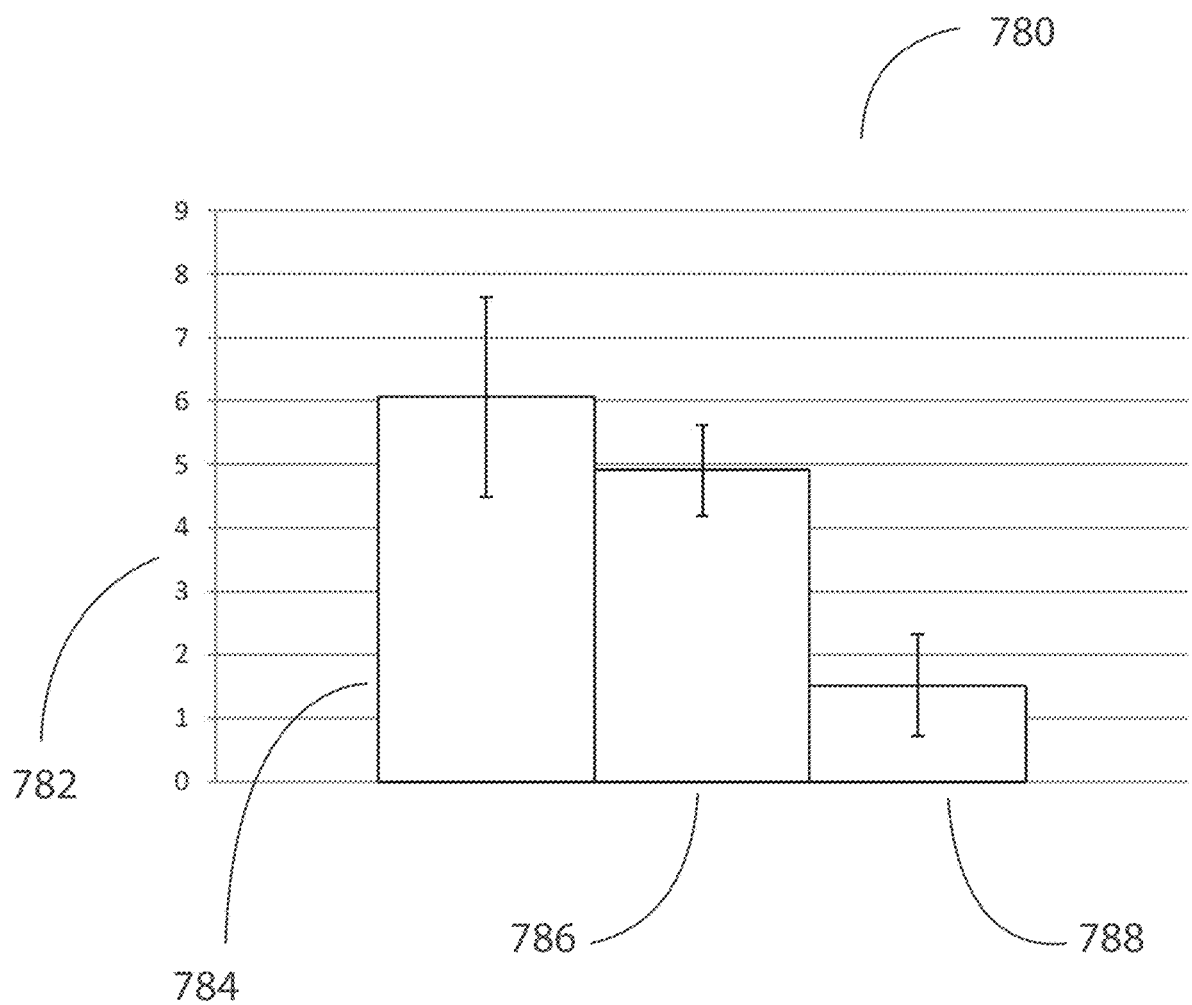
FIG. 7G comprises a graph of erosion depths for laser ADR treated and untreated human molar samples after undergoing an erosive challenge according to some embodiments.

In reference to FIGS. 7C, 7F, and 7G, the E-150i is used with a beam width of 0.82 mm at focus, a 8 uS pulse duration, a 7-location scanned pattern with a 0.35 mm spacing, and a 200 Hz repetition rate. A human enamel sample was moved in front of the scanned laser pattern on a motorized stage for two passes at 3.0 mm/S. FIG. 7C shows an FTIR graph, 740, of human enamel before, 742, and after treatment with these parameters, 744. Carbonate removed was found to be about 50%.

In reference to FIGS. 7D, and 7F, the E-150i is used with a beam width of 0.82 mm at focus, a 10 uS pulse duration, a 7-location scanned pattern with a 0.35 mm spacing, and a 200 Hz repetition rate. A human enamel sample was moved in front of the scanned laser pattern on a motorized stage for two passes at 3.0 mm/S. FIG. 7D shows and FTIR graph, 750, of human enamel before, 752, and after treatment with these parameters, 754. Carbonate removed was found to be about 75%. The only difference in laser parameters between the treatments show in FIGS. 7C and 7D is pulse duration, 8 uS and 10 uS respectively. It can been seen that the samples being treated with the 10 uS parameters had more carbonate removed than the sample treated with the 8 uS parameters.

In order to demonstrate acid resistance, methods and results from a test utilizing an embodiment are disclosed in reference to FIG. 7E-G. A number of human molar samples were treated as described above with both 8 and 10 microsecond pulses. The samples were then masked with nail polish and placed in an erosive challenge for 30 minutes. The erosive challenge had parameters comprising: Temperature: 35 degrees Celsius, pH: 3.6 (Citrate buffer), Acid: 0.052M Citric Acid, and Agitation: 150 RPM stir bar. After the erosive challenge the samples were removed and acetone was used to remove the nail polish. A 3d microscope (Hirox RH-2000 with a 1000× objective) was used to measure eroded surface depths. FIG. 7E shows an image of a sample surface, 760. A masked surface, 762, shows no sign of erosion. An untreated (control) surface, 764, shows pronounced erosion. And, a treated surface, 766, shows only slight erosion. Erosion resistance, $\%_{resistance}$, was calculated based upon height differences between: control, 764, and masked, 762, surfaces, $D_{control}$, and control, 764, and treated, 766, surfaces, $D_{difference}$.

$$\%_{resistance} = \frac{D_{difference}}{D_{control}}$$

FIG. 7F, contains a graph, 770, showing acid resistance, 772, on a vertical axis for both 8 uS, 774, and 10 uS, 776, parameters. Error bars on the graph, 770, represent a 95% confidence interval for acid resistance. A null hypothesis, $H_0$, being: laser treatment does not affect acid dissolution is addressed in reference to FIG. 7G. FIG. 7G contains a graph, 780, of eroded samples treated with the 8 uS laser parameters. The graph has a vertical axis, 782, of eroded depth in micron. The graph, 780, shows three different depths: 1.) $D_{control}$, 784, between the control, 764, and masked, 762, surfaces, 2.) $D_{difference}$, 786, between control, 764, and treated, 766, surfaces, and 3.) $D_{treated}$, 788, between treated, 766, and masked, 762, surfaces. Error bars in FIG. 7G again represent a 95% confidence interval. As can be seen from the graph, 780, the treated surface depth, 788, and the control surface depth, 784, do not overlap. The null hypothesis, $H_0$, is therefore demonstrated to be false as there is greater than a 95% confidence that the treated surface depth mean, 788, and the control surface depth mean, 784, are different.

Disclosure related to FIGS. 3A, 4A. 5, 6A, and 7A is summarized in Table 1 below.

TABLE 1

Different Laser Parameters Yielding Similar Enamel Temperature Results

| FIG. | Parameter: Wavelength [micron] | Parameter: 1/e² Beam Width [mm] | Parameter: Pulse Duration [microseconds] | Parameter: Peak Power [W] | Modeled Result: Peak Surface Temperature [° C.] | Modeled Result: Avg. Spot Temperature [° C.] | Modeled Result: Max Depth with Temperature Greater than 400° C. [micron] |
|---|---|---|---|---|---|---|---|
| 3A | 9.35 | 0.39 | 1 | 500 | 958 | 591 | 3 |
| 4A | 9.35 | 0.26 | 9 | 35 | 983 | 606 | 4 |
| 5 | 10.6 | 0.39 | 20 | 100 | 966 | 595 | 14 |
| 6A | 9.35 | 0.6 | 5 | 300 | 976 | 600 | 4 |
| 7A | 9.35 | 0.79 | 10 | 300 | 974 | 598 | 4 |

Disclosure related to FIGS. 3B, 4B, 6B, 7C, and 7D is summarized in Table 2 below.

TABLE 2

Different Laser Parameters Yielding Similar Carbonate Removal Results

| FIG. | Parameter: Laser Model | Parameter: Wavelength [micron] | Parameter: 1/e² Beam Width [mm] | Parameter: Pulse Duration [microsecond] | Parameter: Scanned [Y/N] | Parameter: No. of Locations [No.] | Parameter: Location Spacing, Ctr-to-Ctr [mm] | Empirical Result: Carbonate Removed [%] |
|---|---|---|---|---|---|---|---|---|
| 3B | E-150i | 9.35 | 0.39 | 1.6 | Y | 19 | 0.2 | 60% |
| 4B | C30 | 9.35 | 0.26 | 9 | Y | 49 | 0.15 | 50% |
| 6B | E-150i | 9.35 | 0.66 | 4.6 | N | 1 | — | 41% |
| 6B | E-150i | 9.35 | 0.66 | 6.6 | N | 1 | — | 50% |
| 7C | E-150i | 9.35 | 0.82 | 8 | Y | 7 | 0.35 | 50% |
| 7D | E-150i | 9.35 | 0.82 | 10 | Y | 7 | 0.35 | 75% |

Disclosure related to FIG. 7F is summarized in Table 3 below.

TABLE 3

Different Laser Parameters Yielding Similar Add Erosion Results

| FIG. | Parameter: Laser Model | Parameter: Wavelength [micron] | Parameter: 1/e² Beam Width [mm] | Parameter: Pulse Duration [microsecond] | Parameter: Scanned [Y/N] | Parameter: No. of Locations [No.] | Parameter: Location Spacing, Ctr-to-Ctr [mm] | Empirical Result: Acid Resistance [%] |
|---|---|---|---|---|---|---|---|---|
| 7F | E-150i | 9.35 | 0.82 | 8 | Y | 7 | 0.35 | 81% |
| 7F | E-150i | 9.35 | 0.82 | 10 | Y | 7 | 0.35 | 83% |

Figure 8A:
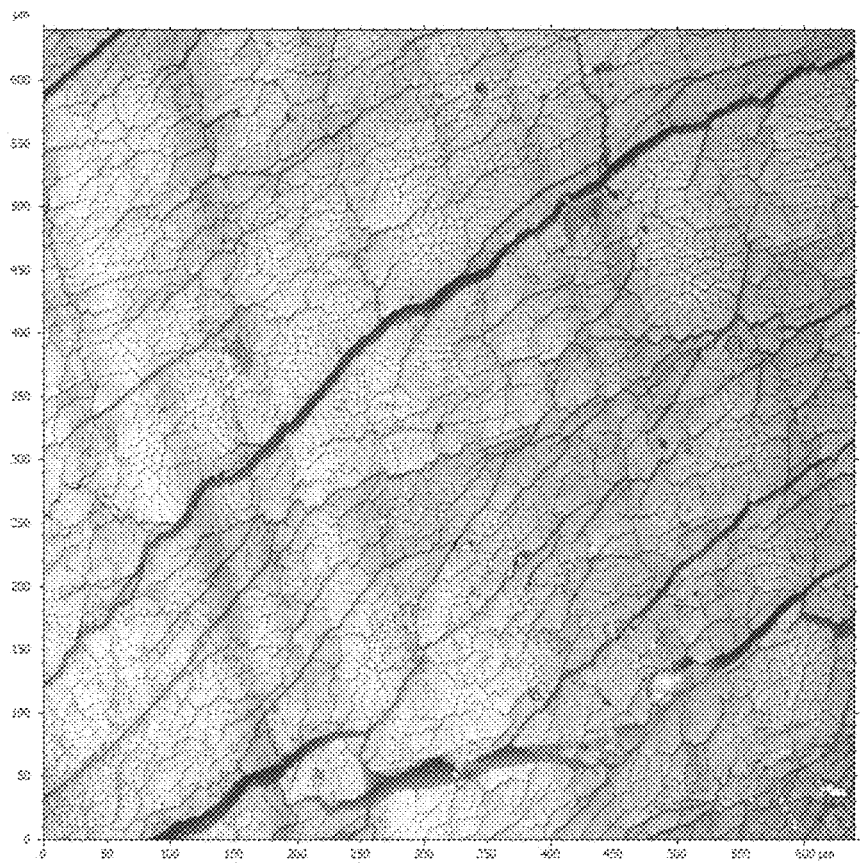
FIG. 8A depicts a microscopic image of ground human enamel heated to about 400 degrees Celsius.

Ground flat enamel when heated can be seen under a microscope to have "scales." These scales are believed to be enamel rods, or groupings of enamel rods. Ground enamel was placed in a furnace and heated. It was found that "scales" began to present at temperatures of about 400 degrees Celsius, see FIG. 8A. At temperatures of about 900 degrees Celsius the "scales" almost entirely cover the surface, see FIG. 8B. At temperatures of about 1200 degrees Celsius surface melting begins to present, see FIG. 8C. The "scales" only present under magnification in ground enamel samples. In unground samples, "scales" do not present, likely because the outer surface of dental enamel is not an aggregate of enamel rods, but is instead a more homogenous layer of enamel. The "scaling" effect correlates well with carbonate removal. "Scales" begin to present at temperatures where carbonate begins to be removed, and "scaling" is largely complete at temperatures where carbonate is largely removed. Because carbonate removal has been repeatedly demonstrated to correlate with acid resistance, the presence of "scales" in ground enamel can be a visual cue for effective treatment in vitro.

Figure 9A:
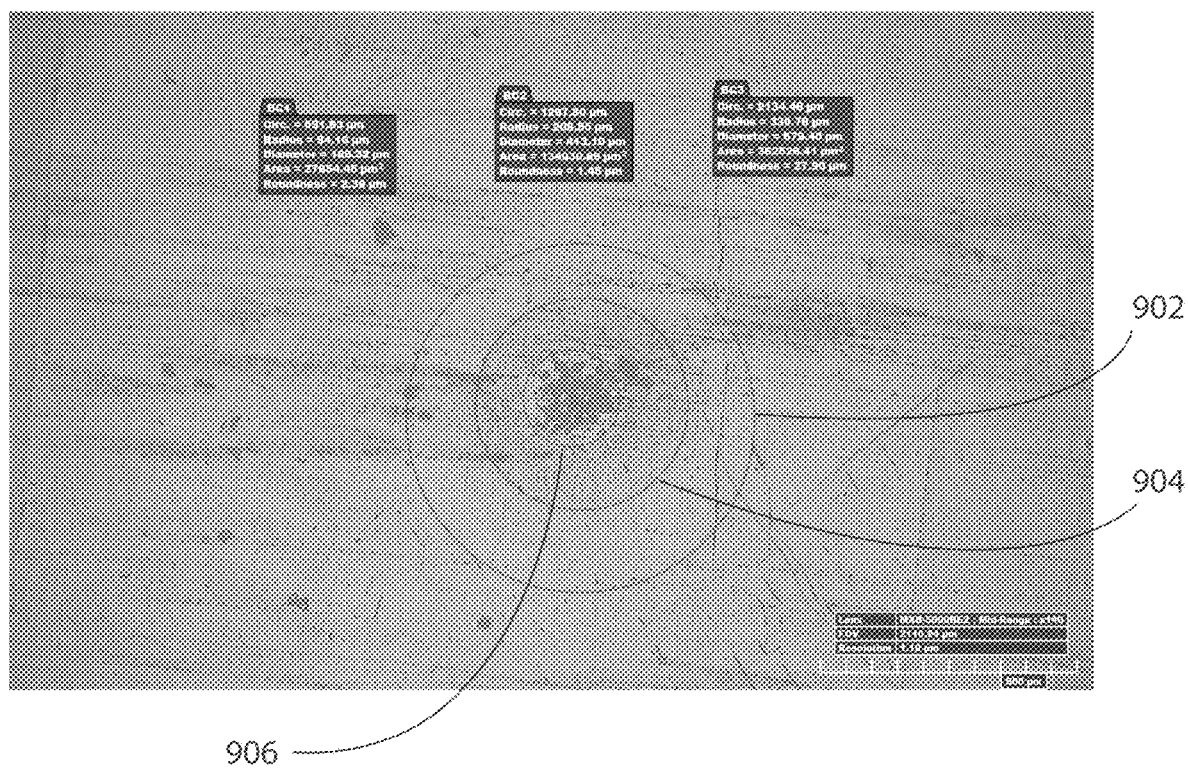
FIG. 9A depicts a microscope image of ground enamel treated by a plurality of laser pulses directed to a single location, according to some embodiments.
Figure 9B:
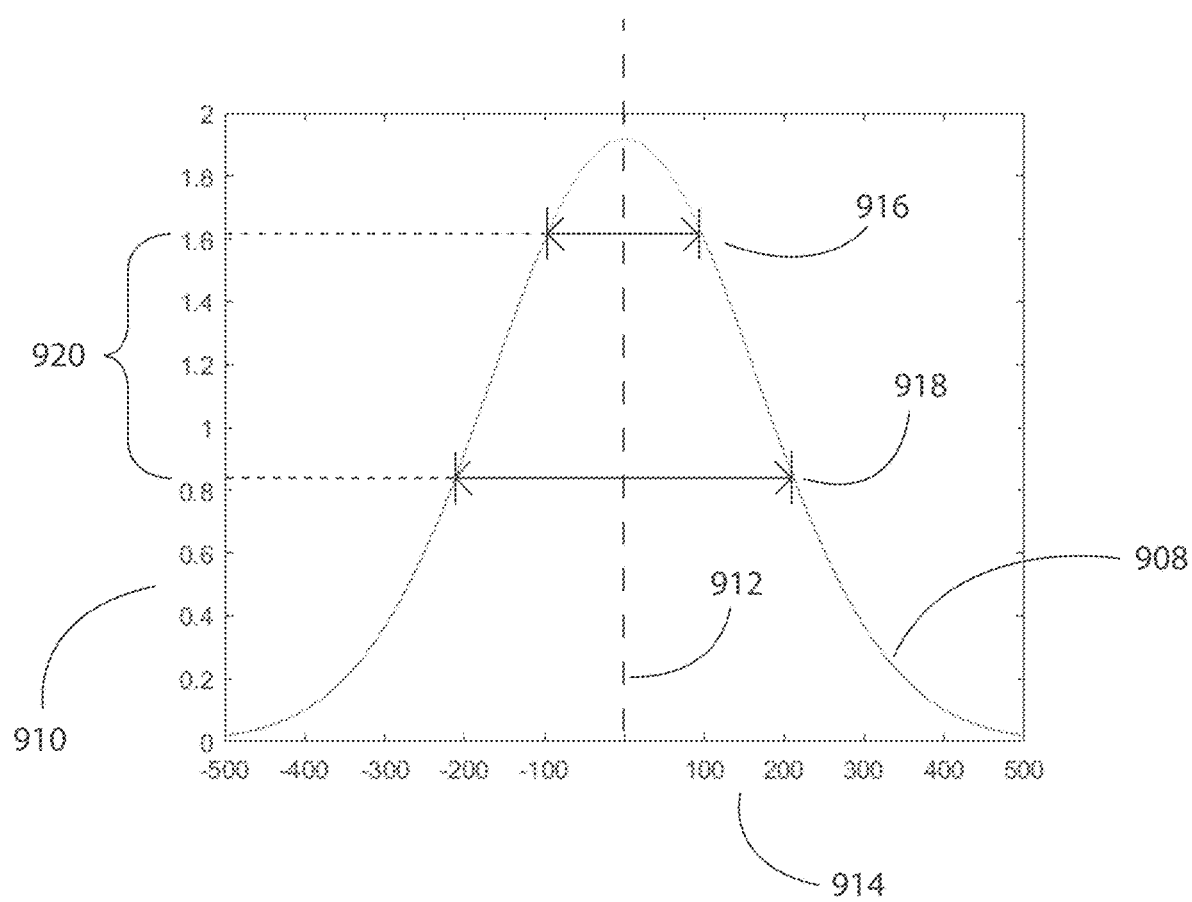
FIG. 9B graphs a fluence profile, indicating an upper fluence threshold and a lower fluence threshold, according to some embodiments.

Using visual cues from a treated surface may inform our understanding of energy density thresholds. For example, an E-150i laser was used to produce 10 pulses at a single location using the following parameters: 0.66 mm beam width, 200 Hz repetition rate, and a 10.6 microsecond pulse duration producing a 3.28 mJ energy pulse. A bovine enamel sample was irradiated and viewed at 200× magnification. An image of the sample is shown in FIG. 9A. Three circles are present in FIG. 9A. An outer circle, 902, estimates a demarcation between slight surface effects and no surface effects. A middle circle, 904, estimates a demarcation having near-complete or complete "scaling" within the middle circle and little or incomplete scaling outside the middle circle. Finally, an inner circle, 906, estimates a demarcation between melt inside the inner circle and no-melt outside the inner circle. Referring to FIG. 9B, given pulse energy and laser beam width and assuming a Gaussian energy profile an energy density profile, 908, can be estimated. The energy density profile, 908, shows a relationship between a local fluence, in $J/cm^2$, on a vertical axis, 910, and a radial distance, in micron, from a center of the laser beam, 912, on a horizontal axis, 914. Plotting a middle circle diameter, 918, and an inner circle diameter, 916, centered upon the energy density profile, 908, provides an estimate at what local fluence a surface effect occurs. It can therefore be estimated from FIG. 9B that complete "scaling" fluences, 920, are between about 0.8 J/cm$^2$ and about 1.6 J/cm$^2$. According to some embodiments, the "scaling" fluences range, 920, represents a therapeutic fluence range between a lower threshold fluence (or a lower therapeutic fluence) represented by a local fluence at the middle circle, 918, and an upper threshold fluence represented by a local fluence at the inner circle, 916.

Figure 10A:
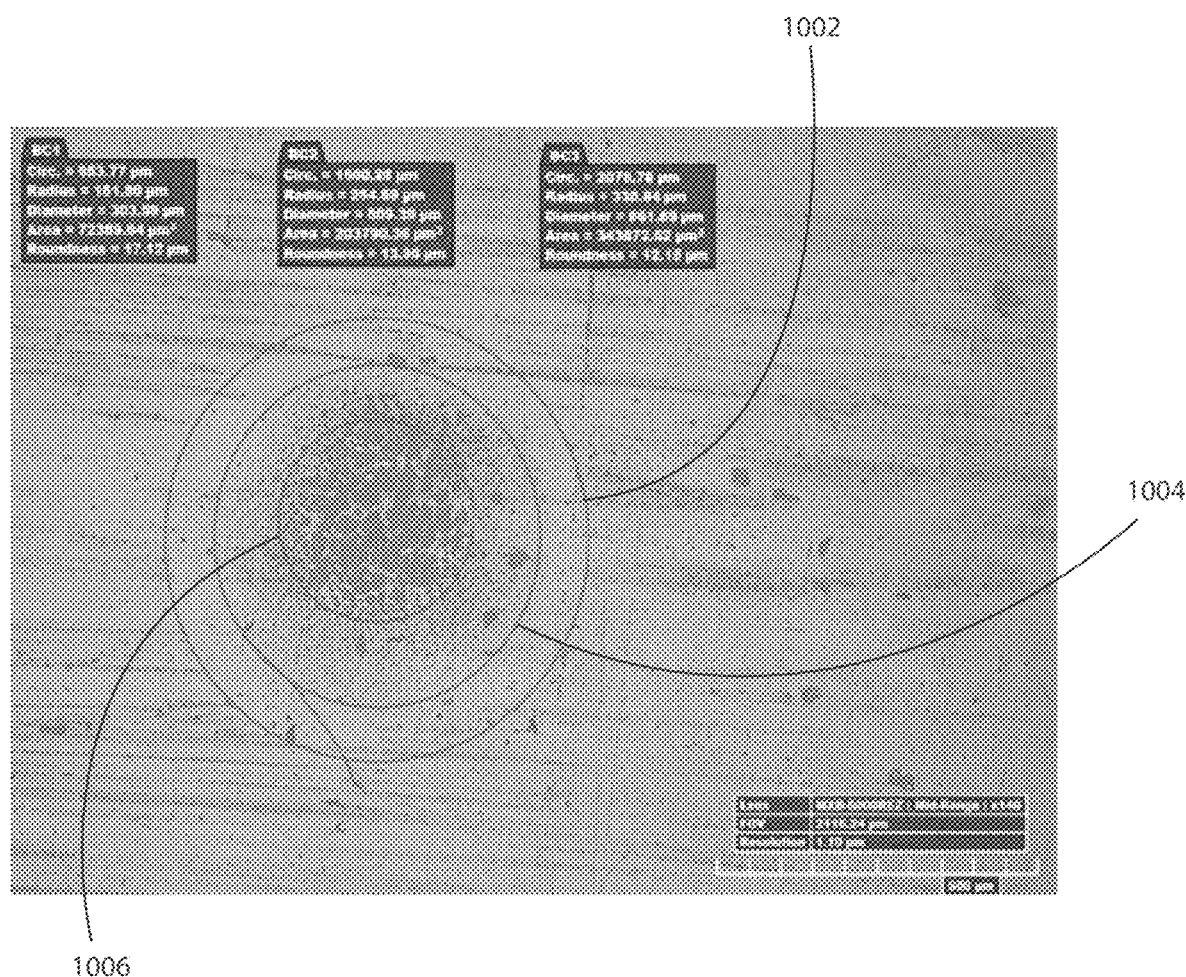
FIG. 10A depicts a microscope image of ground enamel treated by a plurality of laser pulses directed to a single location, according to some embodiments.
Figure 10B:
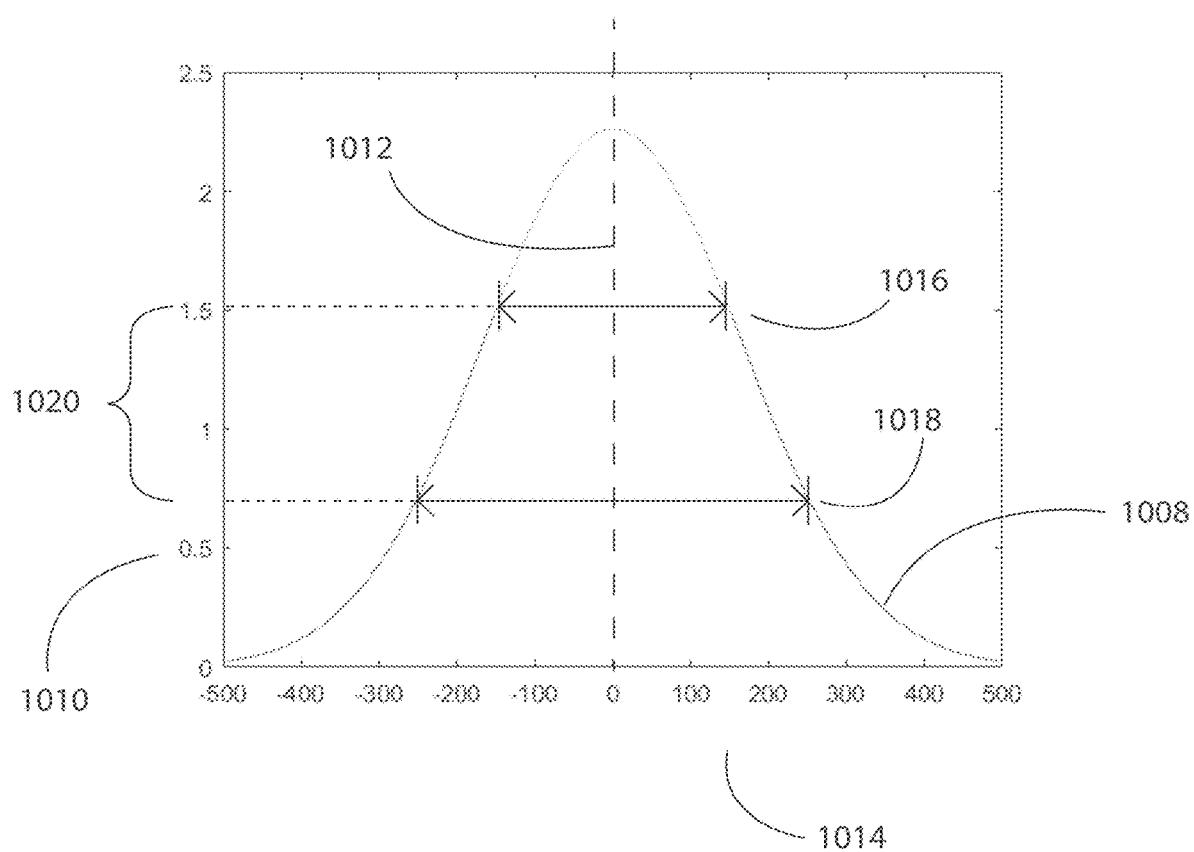
FIG. 10B graphs a fluence profile, indicating an upper fluence threshold and a lower fluence threshold, according to some embodiments.
Figure 10C:
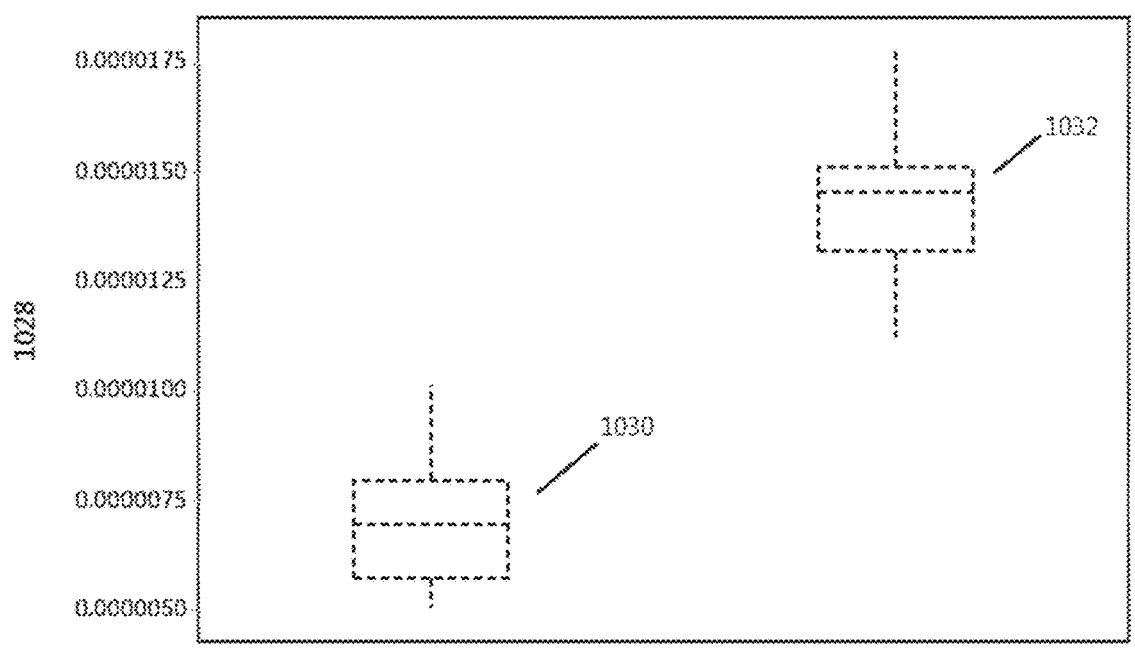
FIG. 10C comprises box plots for a scaling threshold fluence and a melting threshold fluence according to some embodiments.

The above process was repeated with an E-150i laser was used to produce 10 pulses at a single location using the following parameters: 0.66 mm beam width, 200 Hz repetition rate, and a 12.6 microsecond pulse duration producing a 3.87 mJ energy pulse. A Bovine enamel sample was irradiated and viewed at 200× magnification. An image of the sample is shown in FIG. 10A. Three circles are present in FIG. 10A. An outer circle, 1002, estimates a demarcation between slight surface effects and no surface effects. A middle circle, 1004, estimates a demarcation having near-complete or complete scaling within the middle circle and little or incomplete scaling outside the middle circle. Finally, an inner circle, 1006, estimates a demarcation between melt inside the inner circle and no-melt outside the inner circle. Referring to FIG. 10B, given pulse energy and laser beam width and assuming a Gaussian energy profile an energy density profile, 1008, can be estimated. The energy density profile, 1008, shows a relationship between a local fluence, in J/cm$^2$, on a vertical axis, 1010, and a radial distance, in micron, from a center of the laser beam, 1012, on a horizontal axis, 1014. Plotting a middle circle diameter, 1016, and an inner circle diameter, 1018, centered upon the energy density profile, 1008, provides an estimate at what local fluence a surface effect occurs. It can therefore be estimated from FIG. 10B that complete scaling fluences, 1020, in reference to an embodiment disclosed in reference to FIGS. 10A-10B are between about 0.7 J/cm$^2$ and about 1.5 J/cm$^2$. This experiment has been run a number of times (n=35), with multiple: 9.35 micron lasers, beam widths, pulse energies, repetition rates, and number of laser pulses. FIG. 10C shows a box plot, having local fluence in mJ/micron$^2$, along a vertical axis, 1028. A "scaling" threshold, 1030, has a median value of about 0.7 J/cm$^2$. And, a melting threshold, 1032, has a median value of about 1.5 J/cm$^2$, and a lower whisker value greater than 1.1 J/cm$^2$. Given these findings, 9.35 micron lasers typically begin to show "scaling" at a local fluence threshold of about 0.7 J/cm$^2$, and melting begins to occur at local fluences about 1.5 J/cm$^2$. And, generally no 9.35 micron laser produce melt at local fluences below 1.1 J/cm$^2$. These estimations may be done for other wavelength lasers, such as 9.6, 10.2, and 10.6 micron. In some embodiments, local fluence estimations derived from visual cues aid in parameter selection, and can specifically address problem No. 2.) THERAPEUTIC RANGE. In some embodiments, a therapeutic range may be found between a lower threshold fluence, at which treatment generally occurs, and an upper threshold fluence above which undesirable results can occur. For example, in some embodiments a pulse duration (or pulse energy) and laser beam width are selected in order to produce a fluence profile having a maximum local fluence (located at the center of a laser beam) below a minimum melting fluence threshold (e.g. 1.1 J/cm$^2$), while keeping some portion of the fluence profile above a lower therapeutic fluence (e.g. 0.7 J/cm$^2$).

In various embodiments, a laser system achieves the therapeutic fluence range described above by defining a beam width using one or more optics and using a controller to control a pulse energy of the laser beam pulses based on the defined beam width, such that the resulting fluence is within the therapeutic range. As described above, the therapeutic fluence range is difficult to achieve and is highly dependent upon a precise and principled control of various laser parameters. In some instances, in order to achieve the therapeutic fluence range, the laser parameters must generally be controlled with the objective of achieving the therapeutic fluence range. For example, in a system in which pulse energy is controlled based on a defined beam width, the therapeutic fluence may only be achieved if it is an objective of the system. In other words, just because a conventional laser system can control pulse energy, does not mean it can control pulse energy to achieve the therapeutic fluence range, particularly if the system has no reason to operate within the therapeutic fluence range. For example, it would not be obvious to the skilled person to modify a laser system capable of controlling pulse energy, but that operates outside of the therapeutic fluence range (e.g., above the upper threshold to perform melting/ablation, i.e., a surface modification as that term is defined herein), such that it operates within the therapeutic fluence range, because operating within the fluence range is not an objective of such a system.

Referred to above, incorporation of laser beam scanning through the use of a beam guidance system, allows the laser beam to be directed to different areas in the treatment zone. Examples of a beam guidance system are described in U.S. patent application Ser. No. 13/603,165 and 62/332,586, which are incorporated herein by reference. Laser beam scanning allows larger areas to be treated by the laser, than would be possible with a single focused spot. Additionally, scanning ensures that more of the surface is irradiated evenly, with therapeutic fluences. A pattern is used to define parameters associated with scanning, e.g. jump interval, or the time between one point and another in a laser pattern; dwell time, or the time spent at a single point in the pattern; geometry, or the locations of all of the points in a pattern; and point sequence, or the listing of successive points that the beam is directed toward. Parameters associated with the use of a pulsed laser with a beam guidance system are disclosed in detail in U.S. patent application Ser. No. 14/172,562, which is incorporated herein by reference. An exemplary beam guidance system, employs scanners such as galvanometers, and a controller to control the beam guidance system as well as a laser source. An exemplary controller is Maestro 3000 Controller from Lanmark Controls of Acton, Mass.

A pulsed laser system having no beam guidance system or scanning capabilities may pulse the laser through the use of two parameters: pulse width, and repetition rate. A controller suitable for controlling a laser source is a signal generator. Previous studies performed at University of California San Francisco and elsewhere have shown that dental hard tissue being treated by a 9.3 micron laser has a thermal relaxation time of about 2 uS. This value serves to help define the desirable limits for the pulse width parameter. However, little work has been done to define suitable ranges for parameters associated with beam guidance, or scanning of the laser beam during dental hard tissue treatment.

Figure 11:
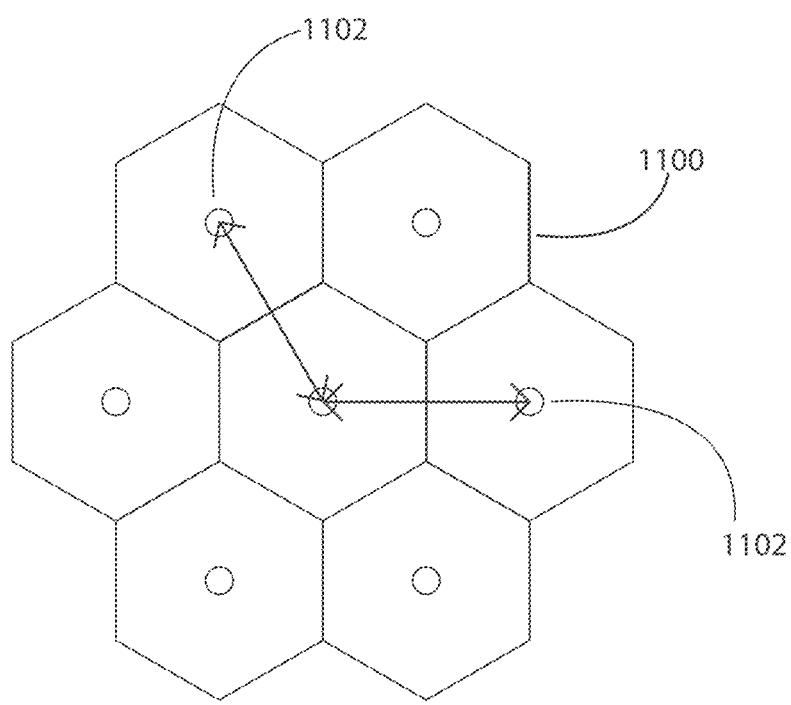
FIG. 11 symbolizes a 7-location laser pattern, according to some embodiments.
Figure 12:
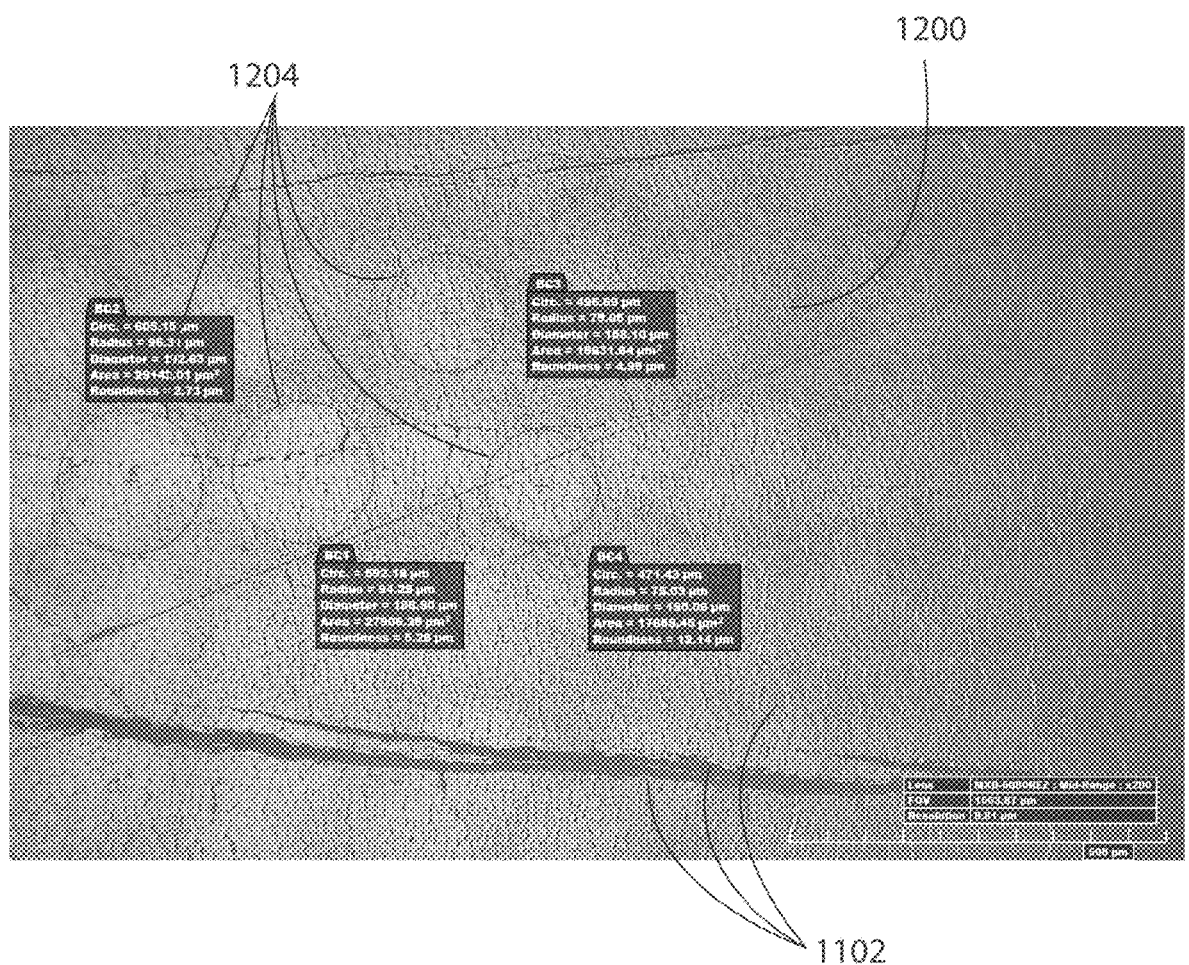
FIG. 12 depicts a microscope image of laser treated ground enamel with visual cues indicating greater heating, according to some embodiments.
Figure 13:
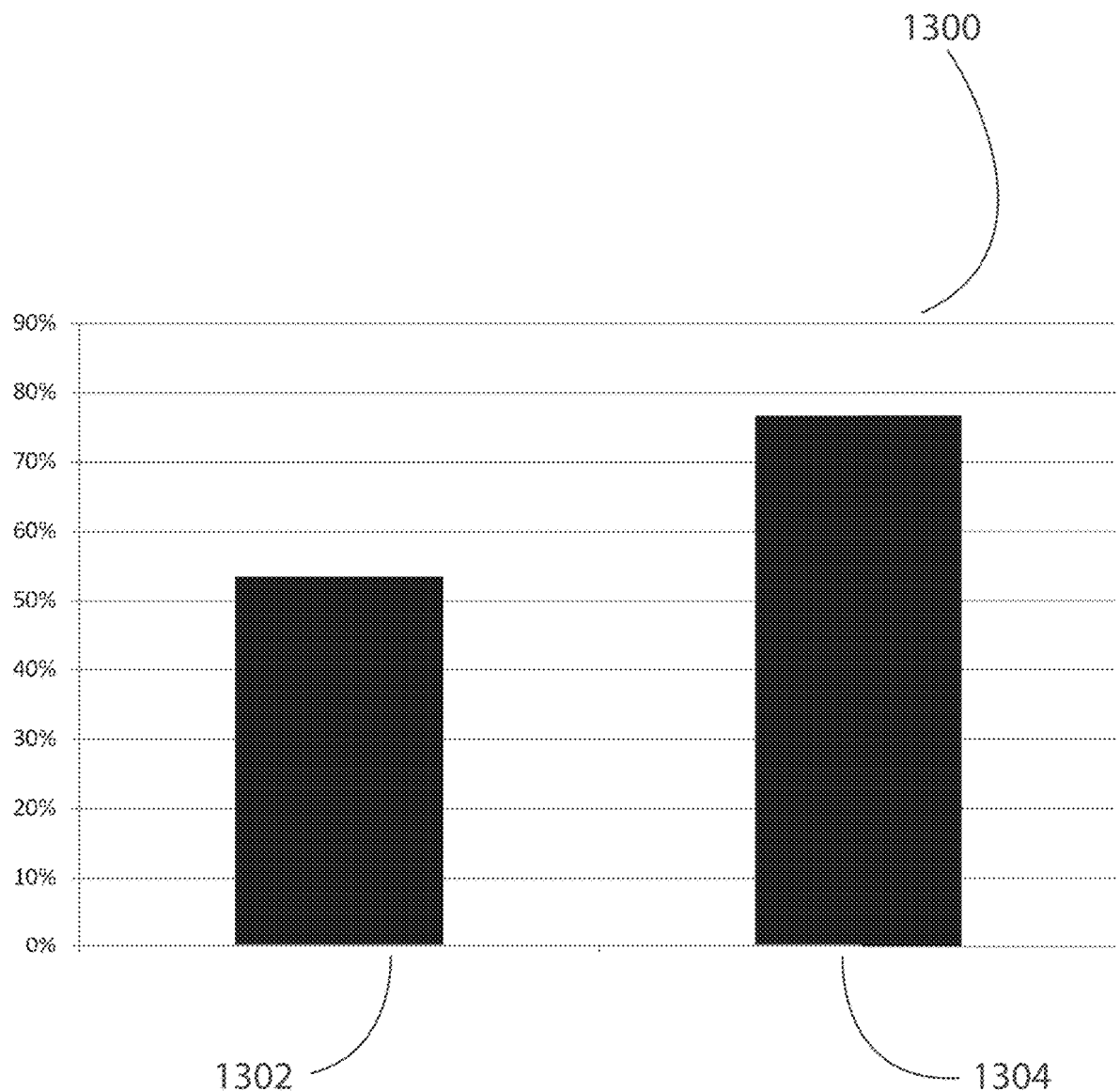
FIG. 13 graphs difference in carbonate removal for two sets of laser parameters having different spacings, according to some embodiments.

A 7-location pattern, 1100, arranged in a hexagonal pattern according to some embodiments is illustrated in FIG. 11. A spacing, 1102, exists between adjacent locations. The hexagonal pattern is advantageous in some embodiments, because it maintains a single spacing between all adjacent points, minimizing the number of parameters required to define the pattern. As mentioned above, in some embodiments the spacing, 1102, is selected based upon local fluence with a laser pulse, or visual cues. According to some embodiments, an E-150i laser is used with: a 0.9 mm beam width, an 18.6 microsecond pulse duration, a 200 Hz repetition rate, and a 7-location hexagonal pattern having a spacing of 0.45 mm. A ground enamel surface after laser treatment at the above parameters is shown in FIG. 12. FIG. 12 shows the surface, 1200, at a 200× magnification. It can be seen that the entire surface is partially "scaled", but that light marks, 1202, are present. Four circles, 1104, are shown as estimate diameters for four light marks in FIG. 12. An average circle diameter of about 0.17 mm was found. The light marks are believed to be visual cues representing greater heating (and more effective treatment) in the sample surface. A therapeutic fluence width is a width, or diameter, over which local fluence is above a lower therapeutic threshold. Referring to FIG. 12, the therapeutic fluence width corresponds to the average circle diameter of about 0.17 mm. In response, a 19-location hexagonal pattern of about the same total size as the 7-location pattern was selected having a location spacing of 0.17 mm based upon the therapeutic fluence width. FIG. 13 contains a graph, 1300, showing carbonate removal measurements for both the 0.45 mm spaced pattern, 1302, and the 0.17 mm spaced pattern, 1304, while all other laser parameters were held constant. It can be appreciated from FIG. 13 that more carbonate is removed by the 0.17 mm spaced pattern than the 0.45 mm spaced pattern. It is therefore advantageous in some embodiments to space scanned locations according to visual cues in a ground enamel sample.

In some embodiments, a spacing between adjacent locations in a scanned laser pattern is selected based according to: laser beam width, a lower threshold fluence, and a upper threshold fluence. Holding pulse energy constant and selecting beam width to ensure the maximum local fluence does not exceed the upper threshold fluence, may be done using an equation below:

$$I_0 = \frac{2*E}{\pi*\omega^2}$$

where E is the pulse energy, $\omega$ is half the beam width, and to $I_0 < I_{melt}$. A therapeutic fluence width exists within a radius, r, where $I(r) > I_{treat}$, $I(r)$, or local fluence at a given radius may be estimated as:

$$I(r) = I_0 * e^{\frac{-2*r^2}{\omega^2}}$$

The proportion of therapeutic fluence width to beam width, or $r/\Omega$, may be estimated according to:

$$\frac{r}{\omega} = \sqrt{\frac{\ln\left(\frac{I_{treat}}{I_0}\right)}{-2}}$$

For example returning again to FIG. 10C, where the lower threshold fluence, $I_{treat}$, is 0.7 (J/cm$^2$), and the upper threshold fluence, $I_{melt}$, and the maximum local fluence, $I_0$, are 1.1 (J/cm$^2$), the proportion of the beam width, $2\omega$, which is above the lower threshold fluence is about 47.5%. Therefore, spacing between adjacent locations should be less than 0.475*beam width to ensure even treatment of a surface.

Another manifestation of problem No. 2.) THERAPEUTIC RANGE relates not to energy density of a laser pulse, but to a number of laser pulses directed toward a single location. If each laser pulse heats the location, and each subsequent pulse acts upon the location while it has an elevated temperature, then surface melting can become a function of number of pulses acting at a location. According to some embodiments, a plurality of laser pulses irradiating a single location do not raise a surface temperature at the single location with each successive pulse. Instead, each of the plurality of laser pulses irradiate the single location once the surface temperature is about an initial surface temperature prior to a first laser pulse. Thus each laser pulse, regardless of a number of preceding laser pulses, will raise the surface temperature similarly to the first laser pulse. Said another way, each laser pulse will raise the surface temperature to a raised surface temperature, which is similar to the raised surface temperature resulting from the first laser pulse. The mathematical model described above was modified in order to estimate an amount of time needed for a surface temperature to return to an initial temperature after a laser pulse. An example estimation of this amount of time is described below.

The model was run with: a peak power of 500 W, a pulse duration of 1 microsecond, and a beam width of 0.385 millimeters. An initial surface temperature is 35 degrees Celsius and ambient temperature is 20 degrees Celsius. Resulting Temperatures were found after 0.1, 1, 10, 100, 1000, and 10000 microseconds, see Table 4 below:

TABLE 4

Modeled Enamel Temperatures after a Laser Pulse

| Time [1*10^n microseconds] | Time after Laser Pulse [microseconds] | Peak Surface Temperature [° C.] | Average Spot Temperature [° C.] |
|---|---|---|---|
| −1 | 0.1 | 955 | 587 |
| 0 | 1 | 840 | 518 |
| 1 | 10 | 527 | 330 |
| 2 | 100 | 232 | 153 |
| 3 | 1000 | 97 | 73 |
| 4 | 10000 | 36 | 36 |

Figure 14:
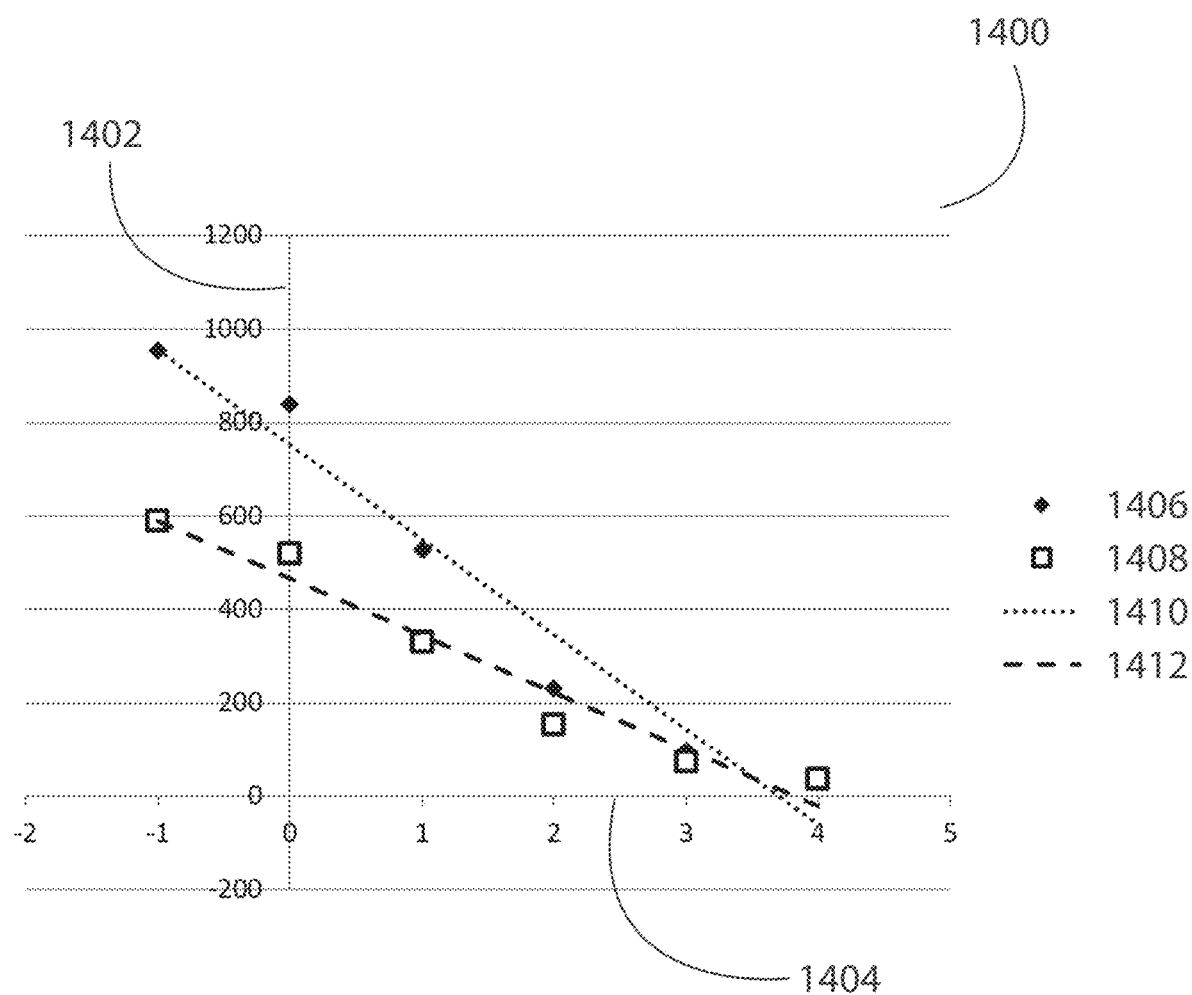
FIG. 14 graphs modeled enamel temperature as a function of cooling time after a laser pulse, according to some embodiments.

Contents of Table 3 are shown in a graph, 1400, in FIG. 14. Temperature is shown in degrees Celsius along a vertical axis, 402. Time after Laser Pulse is shown in microsecond orders of magnitude along a horizontal axis, 404. The graph, 1400, includes peak surface temperature data points, 1406, average spot temperature data points, 1408, a peak surface temperature trend line, 1410, and an average spot temperature trend line, 1412. Equations and R-squared values for the trend lines are recorded below:

$T_{peak} = -203.4*n + 752.93 \; R^2 = 0.957$ $T_{avg} = -121.91*n + 465.7 \; R^2 = 0.9568$ Where $T_{peak}$ is the peak surface temperature, n is orders of magnitude of a microsecond where time, $t = 1 \times 10^n$, and $T_{avg}$ is the average spot surface temperature. Based upon the trend lines the average spot surface temperature reaches 40 degrees Celsius after about $10^{3.492}$ microseconds, or 3.1 mS. And, the peak surface temperature reaches 40 degrees Celsius after about $10^{3.505}$ microseconds, or about 3.2 mS. Therefore, in some embodiments, at least 3.2 mS elapse between laser pulses directed to a single location or two overlapping locations.

Figure 15:
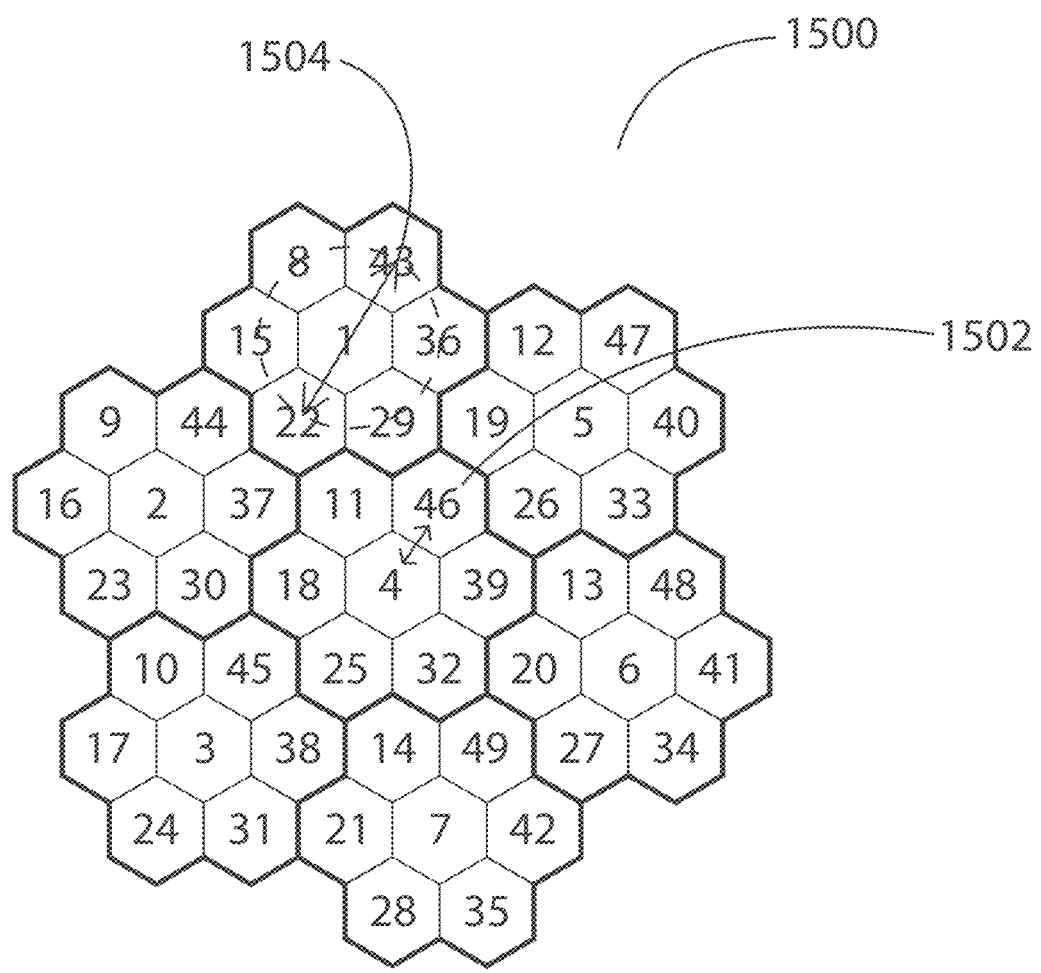
FIG. 15 symbolizes a 49-location pattern and pattern sequence according to some embodiments.

According to some embodiments, a scanned pattern sequence is employed that directs intermediate pulses to intermediate locations after a first pulse directed to a first location and before a second pulse directed to the first location (or, in some cases, a neighbor of the first location). As used herein, a neighbor of the first location is a location (e.g., area impinged by a laser pulse) that is tangent to, overlaps with, and/or is spaced from the first location by a distance below a predetermined threshold (e.g. a percentage of the size of the first location, e.g., 2%, 5%, 10%, 25%, 50%, 75%, and/or 100% of the diameter of the first location) An exemplary 49-location pattern, 1500, illustrating a sequence according to some embodiments, is shown in FIG. 15. The exemplary 49-location pattern, 1500, is well suited for spacings, 1502, that are smaller than laser beam width, 1504, and larger than about ⅓ beam width. Given this relationship, the sequence of the exemplary 49-location pattern, 1500, allows for 6 intermediate pulses between overlapping laser pulses. Referring back to FIG. 14, at least 3.2 mS cooling time should elapse between pulses acting at the same location. Parameters related to scanning can therefore be adjusted to ensure that 3.2 mS elapses between each overlapping location, e.g. location 1 and location 8. A pattern sequence having intermediate pulse locations that also maintains a sufficient cooling time between overlapping pulses increases number of pulses per unit time directed to a treatment region without introducing unwanted heating from additional pulse.

Dental Hard Tissue Cooling

In some embodiments, active cooling is implemented to cool dental hard tissue undergoing treatment. Active cooling allows more laser power to be directed toward a treatment region during treatment, therefore addressing slow treatment speeds, or problem No. 3.)

Treatment Speed.

In some embodiments active cooling is implemented through a fluid system proving a flow of fluid directed toward a dental hard tissue. In some embodiments, the fluid comprises air and is continuously directed toward the dental hard tissue. Referring again back to the mathematical model it was found that increasing the coefficient of convection from 10 W/m² representing natural convection, to 100 W/m² representing forced convection, caused negligible changes to heating of enamel during a laser pulse. It has been found through repeated tests that carbonate removal (as measured by FTIR-ATR) is not impacted by the presences of convective cooling.

Figure 16A:
FIG. 16A shows an X-ray of a human molar having a thermocouple secured in its pulpal chamber.
Figure 16B:
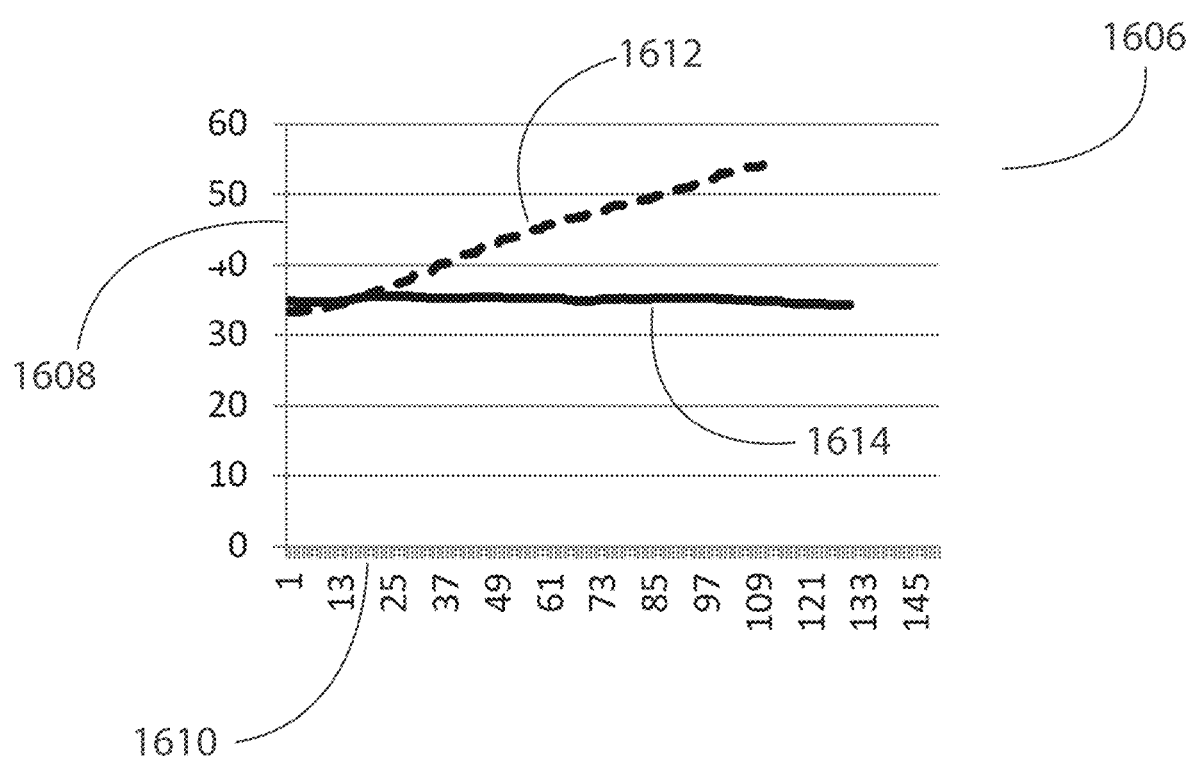
FIG. 16B graphs pulpal temperature rise during treatment with and without air cooling according to some embodiments.

Referring now to FIG. 16A an X-ray, 1600, of a human molar sample, 1602, with a thermocouple, 1604, in its pulpal chamber is shown. It is common practice to measure pulpal temperature rise during a dental treatment with a thermocouple, 1604, in the pulpal chamber of a sample, 1602. Typically dental treatments must stay below a 5.5 degree Celsius pulpal temperature rise to be considered safe. FIG. 16B contains a graph, 1606, having pulpal temperature in degrees Celsius displayed along a vertical axis, 1608, and treatment time in Seconds displayed along a horizontal axis, 1610. The graph, 1606, depicts pulpal temperature rise during an exemplary treatment with an E-150i producing about 0.7 W average power. Initial pulpal temperature is about 35 degrees Celsius. Ambient air temperature is about 20 degrees Celsius. Pulpal temperature of the sample, 1602, undergoing a 0.7 W treatment without cooling, 1612, climbs quickly to more than a 5.5 degree rise in less than one minute. Temperature rise during a 0.7 W treatment with cooling, 1614, is negligible over the same duration. In some embodiments, a fluid delivery system delivering approximately 14 SLPM of air toward the sample through two 1 mm ID holes located approximately 25 mm from the sample.

Figure 17:
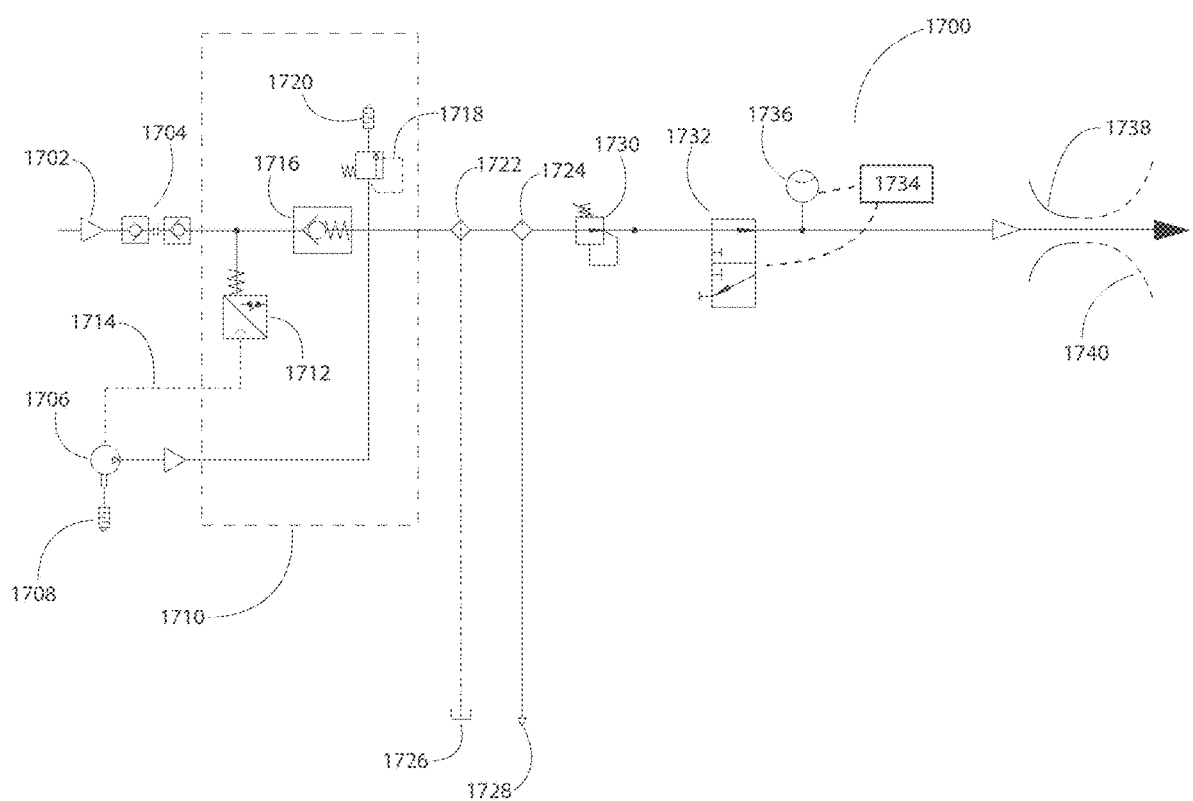
FIG. 17 illustrates a schematic of a fluid delivery system, according to some embodiments.

A fluid delivery system, 1700, is described according to some embodiments in reference to FIG. 17. Air is supplied to the fluid delivery system, 1700, through either: an external air source, 1702, through a quick disconnect fitting, 1704, or an onboard compressor, 1706. Exemplary air requirements for the external air source are a pressure range between 60 PSIG and 100 PSIG, and dry, clean air. An exemplary onboard air compressor, 1706, is a 415ZC36/24 Model from Gardner Denver Thomas running at an RPM of 3600. The onboard air compressor, 1706, may be fitted with a muffler, 1708, in order to quite its operation. In some embodiments, the fluid delivery system, 1700, is configured with an automatic air supply switching system, 1710, to automatically run off the onboard air compressor, 1706, when the external air source, 1702, is not present. The automatic air supply switching system, 1710, comprises an air supply pressure switch, 1712, that is in fluidic communication with the external air supply, 1702, and is in electrical communication with a brake, 1714, on the onboard compressor, 1708. In some embodiments, the air supply pressure switch, 1712, is a normally open switch trigged at pressures of at least 60 PSIG, such that the on board compressor, 1706, will run until the air supply pressure switch, 1712, senses the required pressure and engages the brake, 1714, halting the onboard air compressor, 1706. An air supply check valve, 1716, is located after the air supply pressure switch, 1712, such that air from the on board air compressor, 1706, cannot flow back to activate the air supply pressure switch, 1712. In some embodiments, a pressure relief valve, 1718, is located after the air supply check valve, 1716, in order to prevent greater than specified pressures from reaching the fluid delivery system. In some embodiments, the pressure relief valve, 1718, is set to 100 PSIG and includes a muffler, 1720. Typically, an air filter, 1722, and an air dryer, 1724, are included in the fluid delivery system, 1700. The air filter, 1722, in some embodiments is coupled to an auto drain, 1726, in order for moisture removed from the air. In some embodiments, the air dryer, 1724, is a membrane type air dryer and requires a dryer purge, 1728, for operation. A first air regulator, 1730, is located after the air dryer, 1724. In some embodiments, the first air regulator, 1730, is set to about 56 PSIG. A valve, 1732, is located after the first air regulator, 1730. The valve, 1732, may be a solenoid type valve and controlled by a fluid delivery system controller, 1734. Additionally, the valve, 1732, may include a feedback mechanism indicating to the controller, 1734, the position of the valve, 1732. It may be advantageous in some embodiments, to redundantly ensure that the valve, 1732, is in the correct position and that air is present during treatment. In such cases, an air sensor, 1736, is included in fluidic communication with the fluid delivery system, 1700, after the valve, 1732, and in electrical communication with the controller, 1734. In some embodiments, the air sensor, 1736, is a normally open air switch that closes at about 25 PSIG. The fluid delivery system, 1700, finally delivers the air to one or more orifices, 1738, where it is jetted, 1740, and directed toward a treatment region. Examples of fluids typically delivered by the fluid delivery system, 1700, include compressible fluids such as: air, nitrogen, and helium (for a squeaky clean).

Another embodiment of a fluid delivery system, 1800, which in some embodiments delivers a liquid fluid is described with reference to FIG. 18, and is conceptually similar to a fuel injection system. A fluid store, 1802, is provided in fluidic communication with a pump, 1804. The pump pressurizes the fluid downstream of it. A regulator, 1806, controls the pressure of the fluid. After the regulator, 1806, a high-speed valve, 1808, is located to control the flow of fluid out of one or more orifices, 1810. An example of the high-speed valve, 1808, is a VHS series valve from The Lee Company of Westbrook, Conn. The VHS series valve is capable of up to 1200 Hz operation speeds. The high-speed valve, 1808, is controlled by a controller, 1812. In some embodiments, the controller, 1812, additionally controls laser pulse generation by a laser, 1814. In some embodiments, the controller, 1812, is configured to deliver one or more jets of fluid, and laser pulses asynchronously, in order to prevent interaction between the laser pulse and the fluid. In some embodiments, the controller, 1812, comprises a fluid system controller, 1812A, and a laser controller, 1812B. Wherein, the fluid system controller, 1812A, controls generally just the fluid system, 1800, and the laser controller, 1812B, controls generally just the laser source, 1814, and the fluid system and laser controllers, 1812A-1812B, are synchronized. Repetition rates for laser pulse or fluid jets are in some versions between 20 and 2000 Hz, and typically about 200 Hz. Fluids typically delivered by the fluid delivery system, 1800, include non-compressible fluids, such as: water and alcohol.

Figure 18:
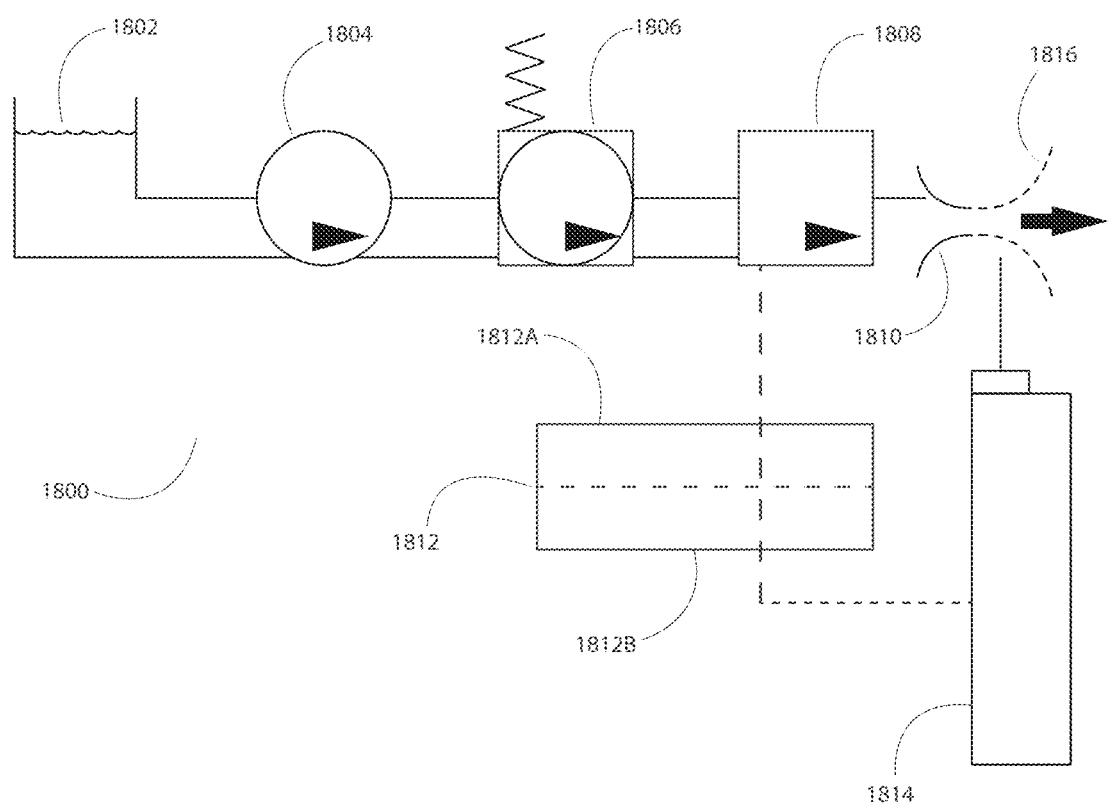
FIG. 18 illustrates a schematic of another fluid delivery system, according to some embodiments.

In some embodiments, both the fluid delivery system described in reference to FIGS. 17 and 18 are employed or a hybrid system incorporating components or designs from each system is implemented. In some embodiments, additives such as fluoride, xylitol, natural and artificial flavors, hydrogen peroxide, desensitizing agents, and chitosan may be included in a fluid directed by the fluid delivery system. The additives may further increase the effectiveness of treatment in the case of Fluoride, or increase the patient experience in the case of natural or artificial flavors. In some embodiments the fluid comprises a stain to aid in differentiation between treated and untreated dental hard tissue.

In various embodiments, the fluid delivery system described in FIG. 17 and/or FIG. 18 can be configured such that rather than directing a pressurized fluid onto the treatment surface, it generates a negative pressure differential such that environmental fluid (e.g., air) surrounding the tooth is pulled over the tooth, which can cause convective cooling of the treatment surface. In such embodiments, the air compressor 1706 in FIG. 17 and/or the pump 1804 in FIG. 18 can be replaced with a vacuum source that, when activated, can generate the negative pressure differential. In some instances, the negative pressure differential can cause air to be pulled across the tooth surface into a nozzle or other orifice of a laser treatment hand piece, advantageously located near the treatment surface. In various adaptations, once the air is pulled into the nozzle, it can be directed through some or all of the other fluid delivery components described above (e.g., valves, regulators, etc.), but in reverse. In other adaptations, some or all of the other fluid delivery components can be excluded and the pulled air can simply be directed through a flow line to a storage tank or an outlet. In some cases, the pulled air can be directed into a compressor or an expander and further used as a working fluid within the system.

Treatment Identification Solution

Figure 19A:
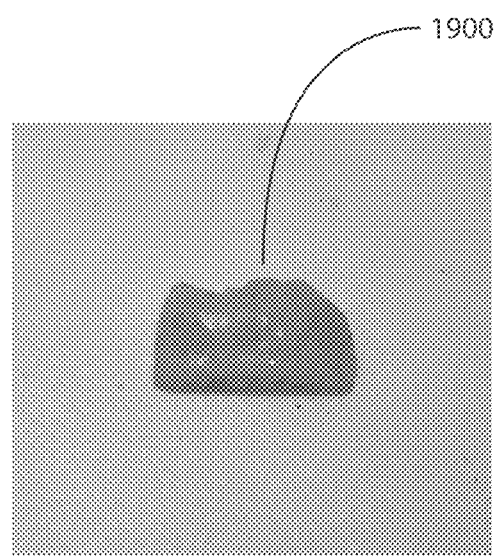
FIG. 19A shows a sectioned human molar having a stain applied according to some embodiments.

In some embodiments, a stain is used to address problem No 4.) INDICATION OF LASER TREATMENT. For example in reference to FIG. 19A, a sectioned extracted human molar, 1900, is completely covered in TRACE Disclosing Solution Manufacturer Part No. 231102 from Young Dental of Earth City, Mo. TRACE contains an active ingredient Red No. 28, also known as phloxine. Phloxine is a water-soluble red dye. TRACE is a common dentistry tool used to indicate the presence of plaque in a mouth. TRACE stains plaque a darker red, and also stains non-plaque covered surfaces in the mouth a lighter pink. Other plaque disclosing solutions that behave in a similar fashion comprise: erythrosine, or Red No. 3. As plaque disclosing solutions erythosine and phloxine containing solutions are hampered by their ability to stain non-plaque covered dental surfaces as well as plaque, reducing contrast between areas with plaque and areas without. This problem has resulted in use of Fluorescein, which generally only stains plaque and can be seen only under a UV light.

Figure 19B:
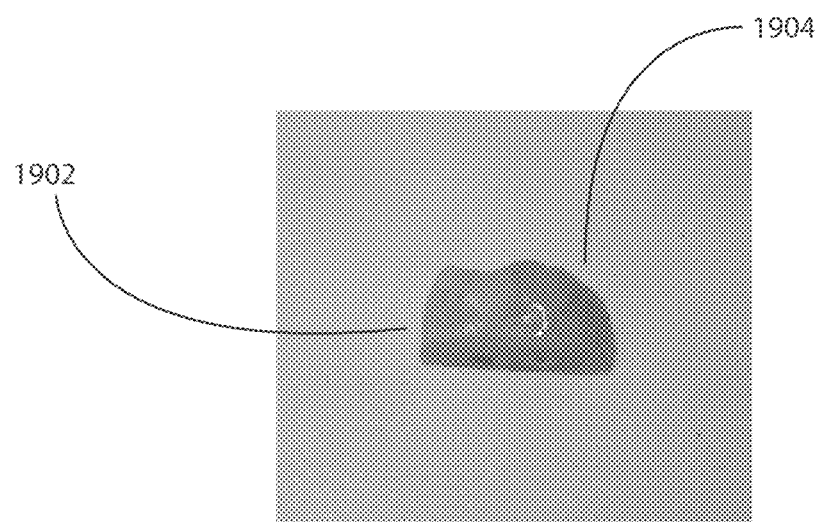
FIG. 19B shows a sectioned human molar with a stain applied having undergone laser treatment on about half its surface, according to some embodiments.

Referring now to FIG. 19B, half of the sectioned extracted human molar has been treated with an E-150i laser, at sub-ablative settings for carbonate removal and acid resistance treatment. A clear distinction is visible between the treated surface, 1902, on the left and the untreated surface on the right, 1904. Presence of disclosing solution during laser treatment has been shown to not significantly alter effectiveness of laser treatment as measured by carbonate removal (FTIR-ATR).

A pellicle is a layer on dental hard tissue within a mouth. The pellicle is formed by saliva within the mouth and is comprised of glycoproteins, including proline rich proteins and mucins. Staining of glycoproteins and mucins is well known in the art of biological staining and histology staining. Some embodiments employ a stain that stains the pellicle covering the dental hard tissue being treated. Examples of pellicle stains include: Bismarck brown Y which stains acid mucins yellow, Mucicarmine stain which is currently used in surgery to detect the presence of mucins, as well as food colorings and dyes. Additional embodiments employ a stain that adheres to the pellicle.

During laser treatment the pellicle, plaque, and biofilm covering the dental hard tissue is ablated. This occurs because treatment requires a surface temperature of the dental hard tissue to be raised to between about 400 degrees Celsius and 1200 degrees Celsius momentarily. Therefore stains which act upon the pellicle or are adhered to the pellicle are removed during treatment. A temperature necessary for removal of a portion of the pellicle, plaque or biofilm is typically over 100 degrees Celsius. For example, dental autoclaves intended to remove or sterilize oral fluids typically operate between 121-132 degrees Celsius.

An embodiment of laser treatment comprises the following steps. A stain is applied to all dental hard tissue surfaces in a patient's mouth. And, a dental laser system is used at appropriate parameters (see above) to treat all stained hard tissue surfaces in the patient's mouth. As a stained treatment region is treated, stain is removed returning the surface to its natural color. Laser treatment continues until all dental hard tissue surfaces are returned to their natural color.

Figure 8B:
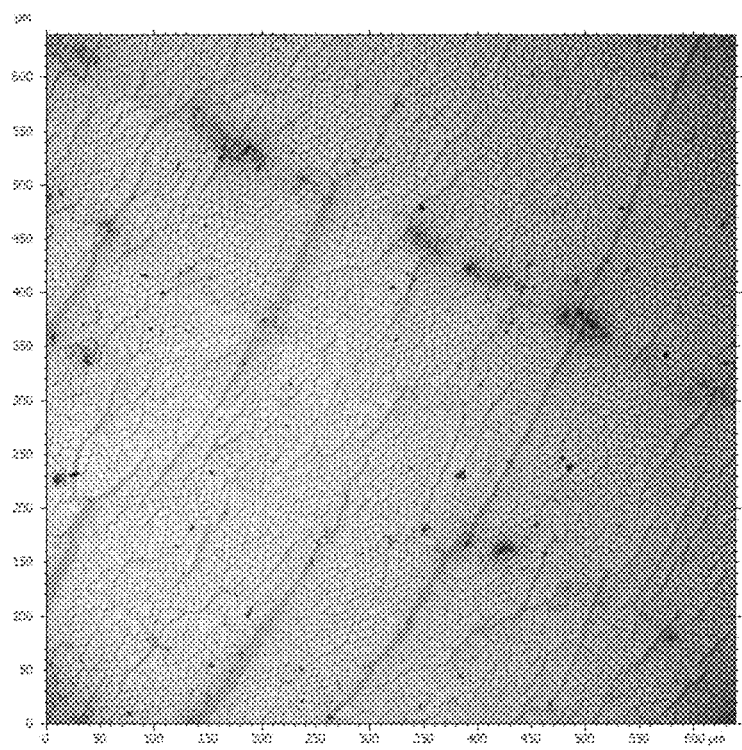
FIG. 8B depicts a microscopic image of ground human enamel heated to about 900 degrees Celsius.
Figure 8C:
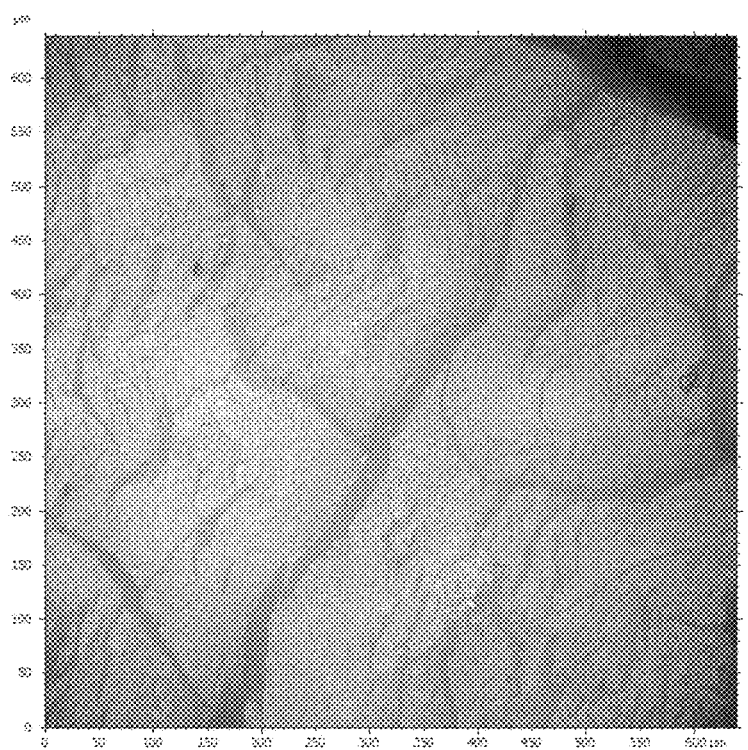
FIG. 8C depicts a microscopic image of ground human enamel heated to about 1200 degrees Celsius.

As described above, according to some embodiments preventative 8 to 12 um laser treatment elevates the local surface temperature of the enamel, such that various biofilms are removed, including: tartar, calculus, and pellicle. Referring to FIG. 8B, enamel under high magnification displays "scales" which are believed to be tops of enamel rods, which comprise tooth enamel. The structure of a tooth's enamel is clearly visible in part, because the biofilm, and any additional smear layer from grinding, have been removed from the tooth's surface. After laser treatment the enamel can be said to have an exposed surface, which is largely free from biofilms. According to some embodiments, the exposed enamel surface is treated with a whitening agent after the biofilms, to some extent, have been removed. The whitening agent would typically contain from 1 to 60% hydrogen peroxide, with or without an optically activated agent added. The optical activation wavelength for various whitening activation agents can be provided from a source with a wide spectral range, for example between 200 nm and 20 um. Hydrogen peroxide breaks down into an oxygen radical which removes stain on the enamel. With the biofilm and pellicle layer generally removed with laser treatment, the whitening agent can be applied more directly to the enamel surface removing more stains. According to some embodiments, the composition of the whitening agent can vary and still be effective as the main advantage is not the actual whitening agent's composition, but applying the whitening agent directly onto an exposed surface of the enamel. The pH of a whitening agent is typically formulated as close to 7 (neutral, non-acidic) as possible. In some embodiments, neutral whitening agent is employed, because the tooth enamel to an acidic whitener typically results in erosion.

According to some embodiments, a fluoride treatment is applied to the exposed enamel surface after laser treatment. It is known in the art that fluoride treatments increase a tooth's resistance to cavities and too some extent erosion. In some embodiments, a fluoride uptake is increased by through application of fluoride directly to the exposed enamel surface. In some embodiments, fluoride treatment comprises a fluoride varnish, such as: Embrace Varnish from Pulpdent of Watertown. Mass. Embrace varnish comprises 5% Sodium Fluoride with Calcium, Phosphate, and Xylitol.

Exemplary Treatment Specifications

Some embodiments of a dental laser system for treatment have specifications according to Table 5 below:

TABLE 5

Laser System Specifications

|  | Min. | Max. | Nom. |
| --- | --- | --- | --- |
| Average Laser Power (W) | 0.05 | 5 | 1 |
| $1/e^2$ Beam Width at Focus (mm) | 0.1 | 10 | 0.8 |
| Laser Wavelength (micron) | 7.0 | 12.0 | 9.35 |
| Scanned Location Spacing (mm) | 0 | 5 | 0.17 |
| No. Pulses per Location (—) | 1 | 1000 | 1 |
| No. of Locations (—) | 1 | 1000 | 19 |
| Energy per Pulse (mJ) | 0.05 | 100 | 3.5 |
| Optical Pulse Duration (uS) | 1 | 100 | 10 |
| Average Repetition Rate (Hz) | 1 | 10000 | 200 |

Some embodiments of treatment have performance specifications according to Table 6 below:

TABLE 6

Treatment Performance Specifications

|  | Min. | Max. | Nom. |
| --- | --- | --- | --- |
| Carbonate Removed per FTIR-ATR Method (%) | 10% | 100% | 50% |
| Pulpal Temperature Rise (° C.) | −5 | 3 | 0 |
| No Enamel Surface Melt Present Under Microscope Magnification (X) | 50 | 10000 | 200 |
| Bovine Enamel Erosion Depth after 7 min 1% Citric Acid Erosive Challenge (micron) | 0 | 2 | 0 |
| Increased Whitening (VITA Shade) | 0.5 | 5 | 1 |
| Increased Fluoride Uptake (%) | 10% | 1000% | 100% |

Closed Loop Laser Control

As outlined above, laser treatment to resist acid dissolution requires that laser energy be delivered within a therapeutic range (Problem No. 2.). $CO_2$ lasers which produce wavelengths well suited for treatment are known to vary in average power and energy per pulse. $CO_2$ laser manufacturers produce lasers only within wide average power specifications, and individual $CO_2$ lasers will vary in average power during use. It is therefore advantageous for a laser system and method for treating dental hard tissue to control the average power, or energy per pulse of the laser.

Figure 20:
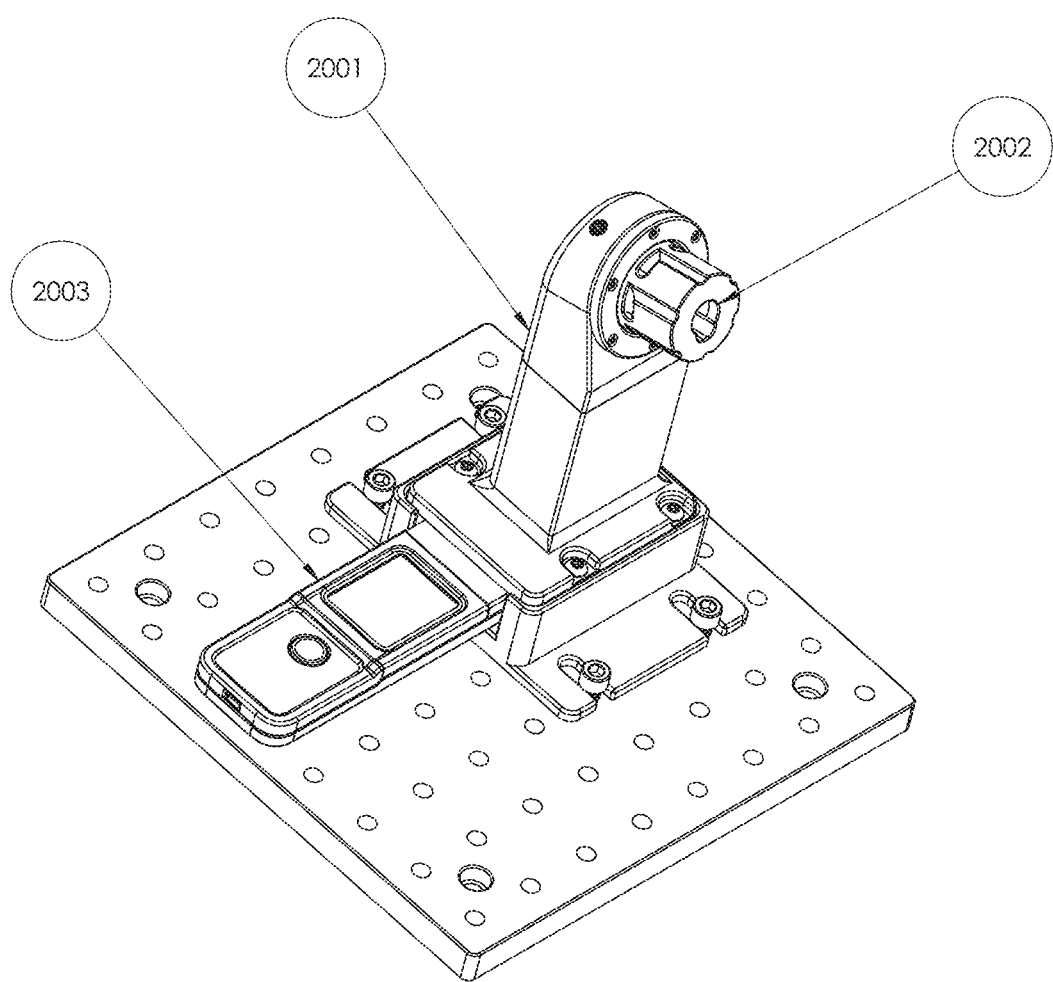
FIG. 20 shows a drawing of a laser output sensor for closed-loop operation, according to some embodiments.

Referring now to FIG. 20, a laser output meter, 2001, is disclosed. The laser output meter, 2001, has a hand piece port, 2002, into which a hand piece of a laser system (not shown) may be inserted. The laser power meter, 2001, is configured to secure the inserted hand piece, and direct an output of the hand piece toward a sensor, 2003. According to some embodiments, the sensor, 2003, comprises a laser power detector such as: The PRONTO-250-PLUS from GenTec-EO of Quebec, QC, Canada. The PRONTO-250-PLUS is well suited for power measurements in the range of 0.1-8.0 W. The PRONTO-250-PLUS offers+/−3% accuracy (compared to +/−5% normally offered by laser power meters of this type).

In order to use the laser output meter, 2001, a clinician places a hand piece into the hand piece port, 2002, and fires a laser at a known repetition rate and pulse duration. The sensor, 2003, measures and reports an actual average output power. The clinician then varies the repetition rate or the pulse energy of the laser until a desired average power reading is achieved. In some embodiments, the pulse duration is varied while the repetition rate is held generally constant. In these embodiments, a change in average output power corresponds to a change in pulse energy. As described above, in some embodiments, pulse energy must be controlled in order to provide the laser energy within a therapeutic range (Problem No. 2). Once the laser sensor, 2003, reports a desired average laser output power the clinician begins treatment.

Figure 21A:
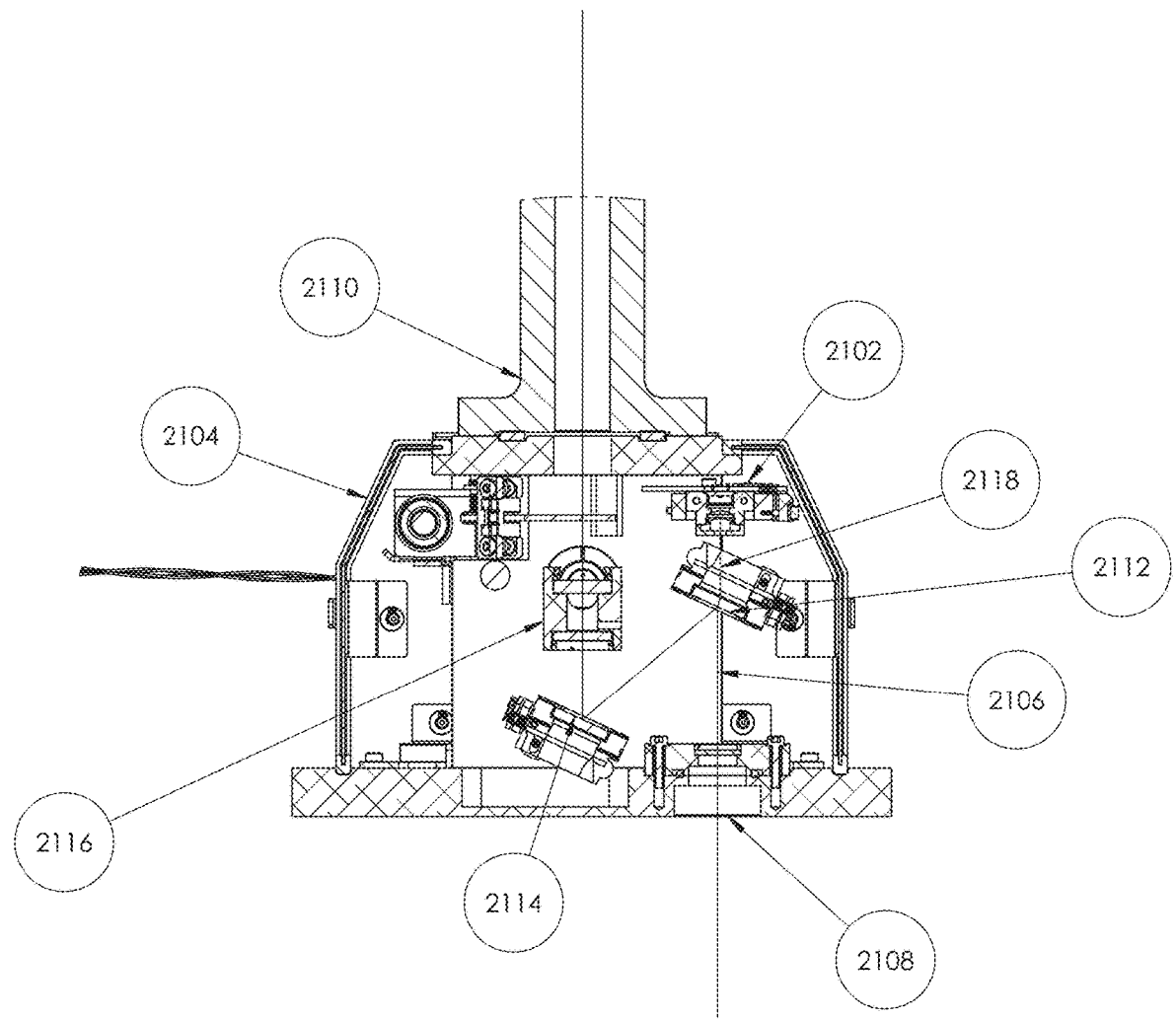
FIG. 21A shows an optical system comprising an integrated laser sensor, according to some embodiments.
Figure 21B:
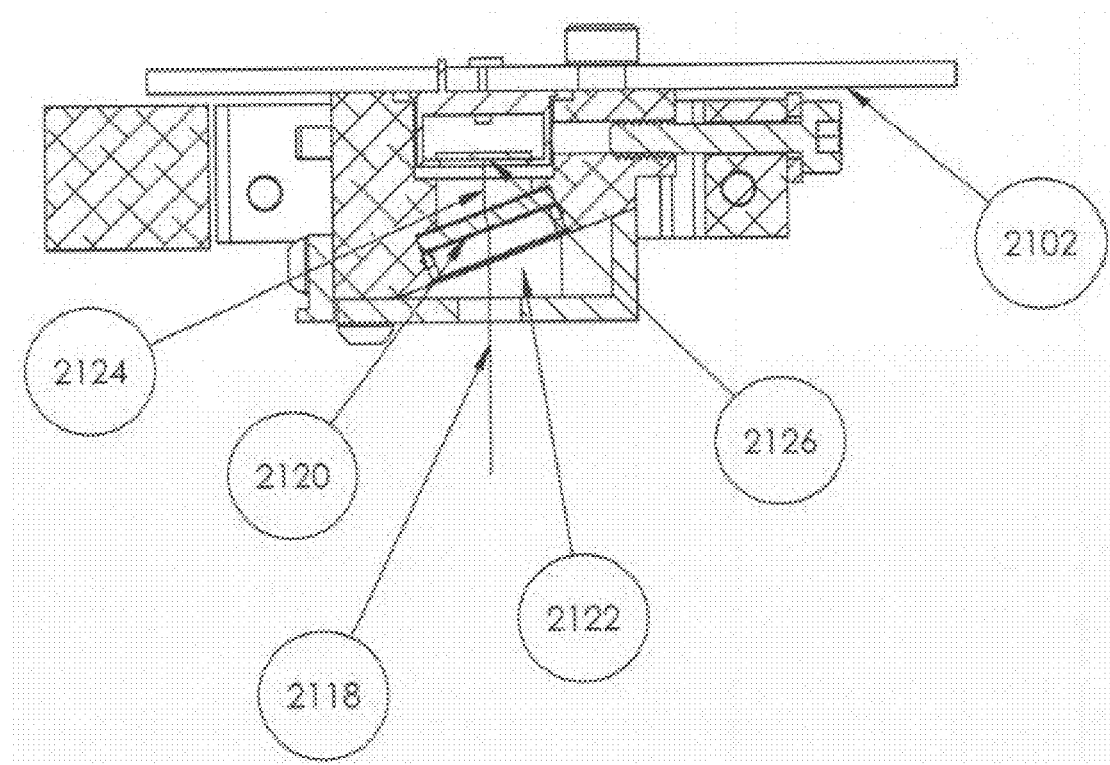
FIG. 21B shows an integrated laser sensor, according to some embodiments.

Another embodiment of closed loop laser control employing an integrated laser sensor, 2102, is illustrated in FIG. 21A-B. FIG. 21A depicts an optical assembly, 2104, adapted to accept a laser beam, 2106, in through an input aperture, 2108, and align the laser beam into an articulating arm, 2110. Within the optical assembly, 2104, the laser beam, 2106, is redirected by a first reflector, 2112, and a second reflector, 2114. In some embodiments, an optical sub-assembly, 2116, acts on the laser beam, 2106. According to some embodiments, the first reflector, 2112, is partially transmissive, such that a laser beam portion, 2118, may pass through the first reflector, 2112, and be directed toward the integrated laser sensor, 2102. According to some embodiments, the first reflectors "picks off" about 1% of the laser beam, 2106, and the laser beam portion, 2118, has a power that is about 1% of that of the laser beam, 2106. The integrated laser sensor, 2102, therefore measures a laser beam portion, 2118, which is representative of the laser beam, 2106. The integrated sensor, 2102, is therefore well-suited for measuring variations in laser power during a treatment in real-time or near-real-time.

FIG. 21B illustrates a cross-section of an integrated laser sensor, 2102, according to some embodiments. A laser beam portion, 2118, is acted upon by an ND filter, 2120. The ND filter may reflect away an unused laser beam portion, 2122. An exemplary ND filter transmits a measurable laser beam portion, 2124, that has a power between 0.30% and 0.17% of that of the laser beam portion, 2118. The measurable laser beam portion, 2124, irradiates a photodetector, 2126. In some embodiments, the photodetector, 2126, comprises one of: Mercury Cadmium Telluride (MCT) sensor. PowerMax Pro Sensor from Coherent (U.S. Pat. No. 9,059,346), and Indium Arsenic Antimony (IAA) sensor.

Figure 22:
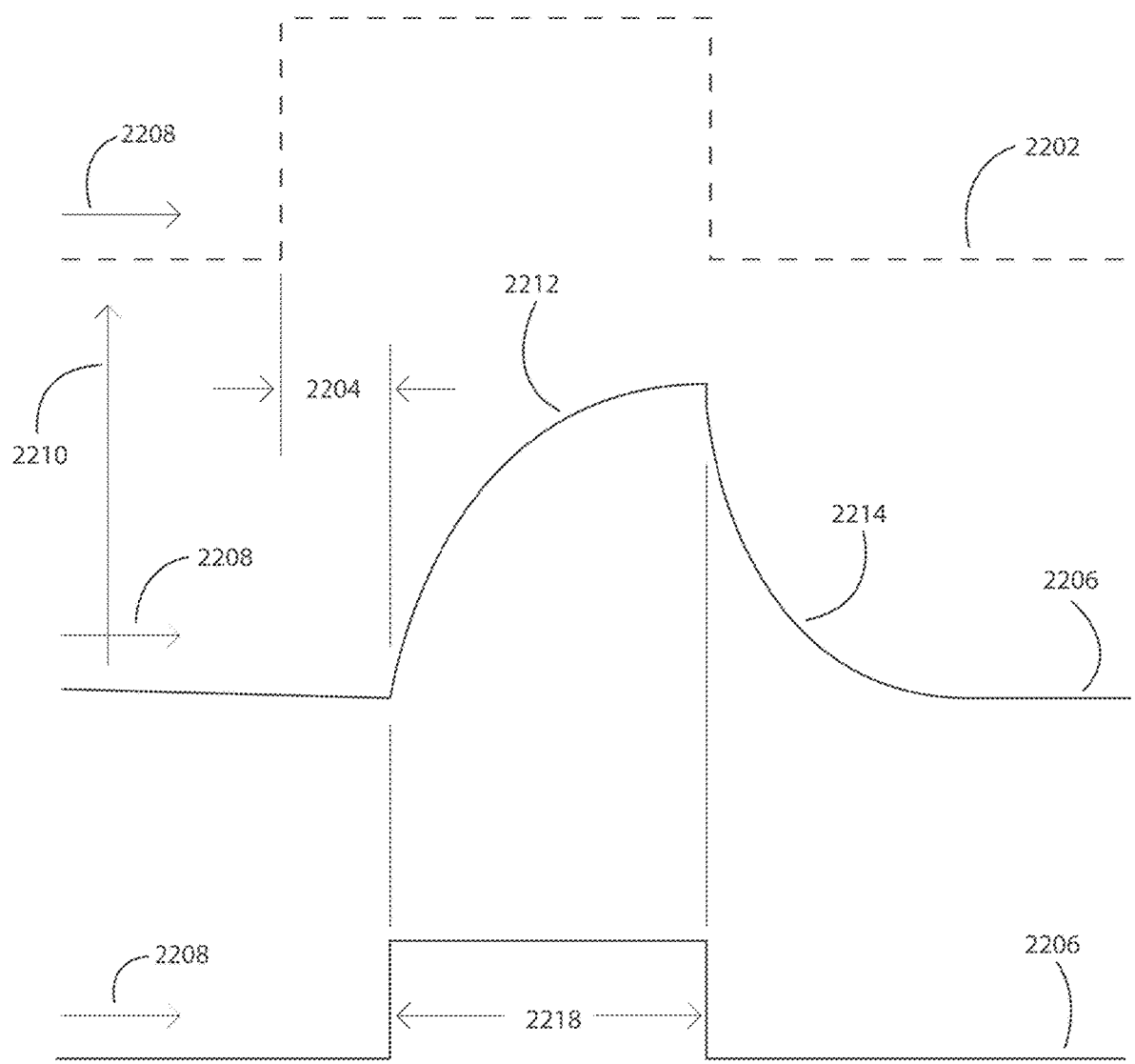
FIG. 22 shows a laser signal and a laser trigger signal related to an integrated laser sensor, according to some embodiments.

FIG. 22A depicts operation of an integrated laser sensor as employed by some embodiments. Typical, $CO_2$ lasers are controlled by a trigger signal, 2202, and begin a laser pulse after an offset, 2204. A laser signal, 2206, is sensed by the integrated laser sensor. The laser signal, 2206, is shown in a graph having time, 2208, in a common horizontal axis, and peak power, 2210, in a vertical axis. Typical $CO_2$ lasers produce a laser pulse that resembles a shark fin, having a rising edge, 2212, and a falling edge, 2214. According to some embodiments, the signal, 2206, from the intergrated laser sensor is filter to produce a digital pulse duration signal, 2216, which is true only during the rising edge, 2212. A rise time, 2218, is equal to a duration of time the digital pulse duration signal is true, and is also a measured representation of an optical pulse duration of the laser. According to some embodiments, feedback from the integrated laser sensor is used to control an optical pulse duration.

Figure 23A:
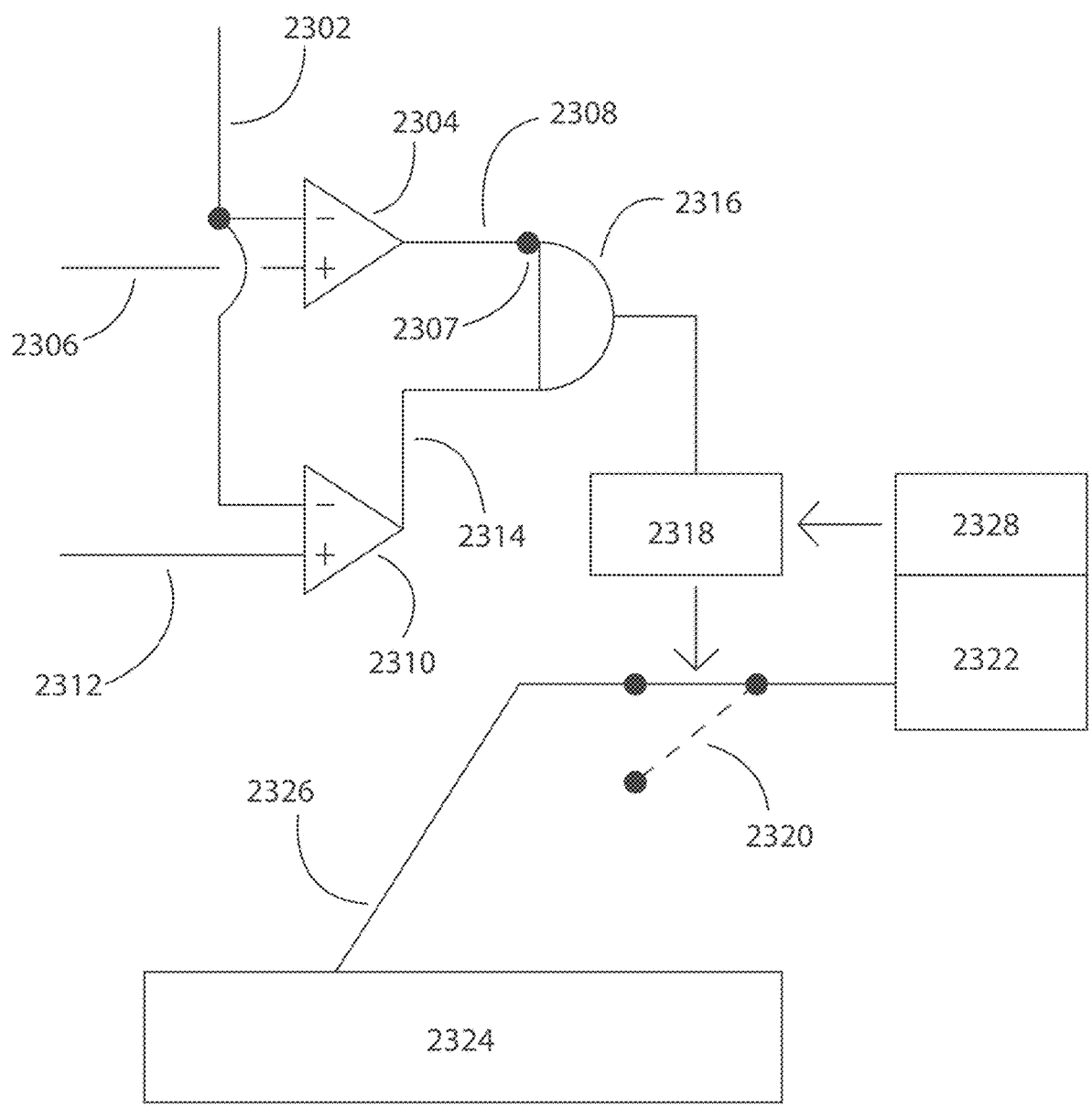
FIG. 23A shows a circuit related to an integrated laser sensor, according to some embodiments.
Figure 23B:
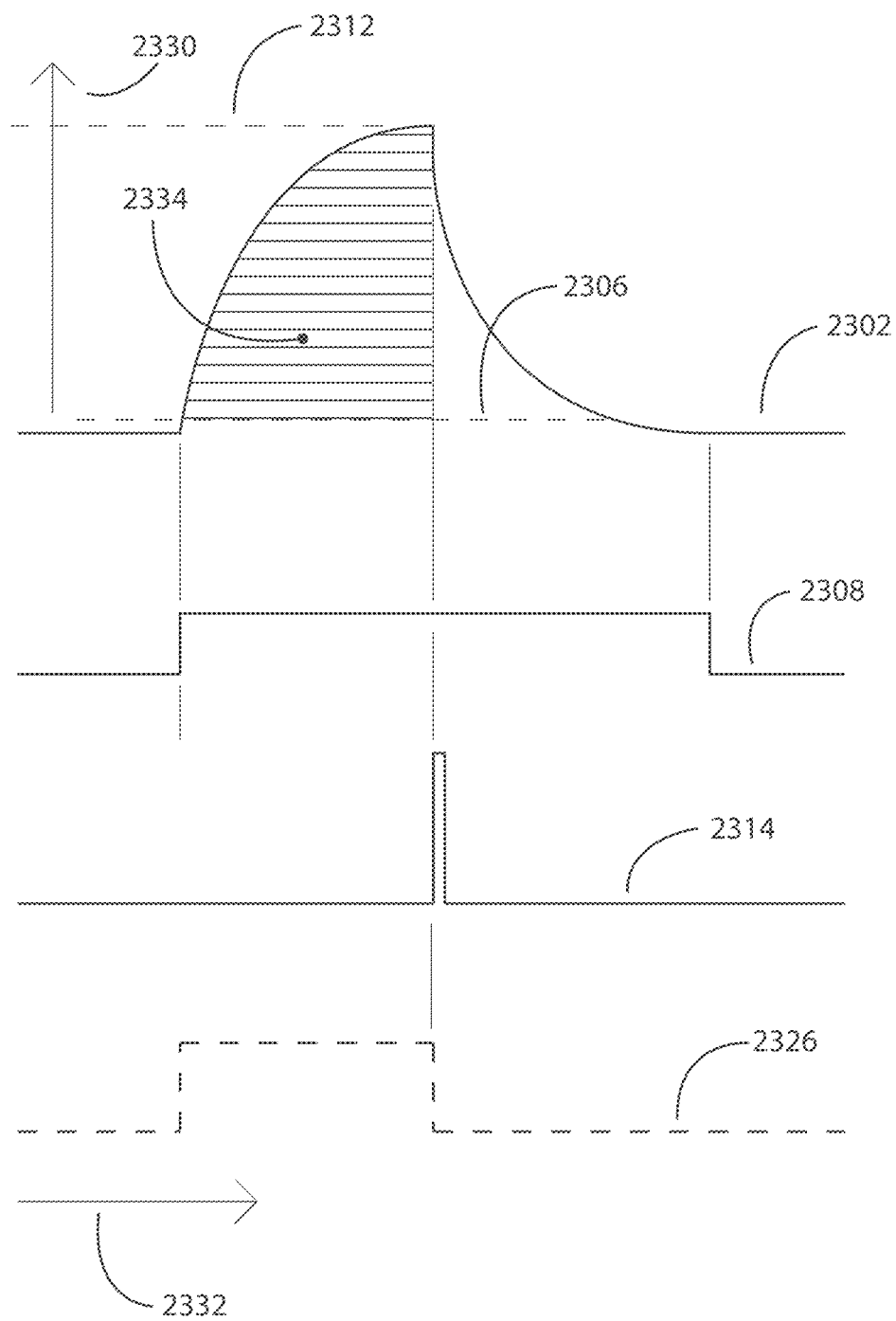
FIG. 23B shows a laser signal and a laser trigger signal related to an integrated laser sensor, according to some embodiments; and, FIG. 24 shows a laser signal and a laser trigger signal related to an integrated laser sensor, according to another embodiment.

Referring now to FIGS. 23A-B, an integrated power sensor is employed according to another embodiment. Referring to FIG. 23A, a laser signal, 2302, is provided by the integrated power sensor. A first comparator, 2304, compares the laser signal, 2302, with a minimum power threshold, 2306. The minimum power threshold, 2306, is a power value that is typically a smallest measurable amount. The first comparator, 2304, and invertor, 2307, output a first comparator signal, 2308, that is digital and has a true value only when the laser power signal, 2302, is greater than the minimum power threshold, 2306. The laser signal, 2302, is further provided to a second comparator, 2310, which compares it with a maximum power threshold, 2312. The second comparator, 2310, outputs a second comparator signal, 2314, that is digital and true only when the laser signal, 2302, is greater than the maximum power threshold, 2312. The first and second comparator signals, 2108 and 2314, enter an and-gate, 2316. The and-gate, 2316, is in communication with a latch, 2318, such that when both first and second comparator signals are true, a connection, 2320, is opened and held open. The connection, 2320, is located within electrical communication, between a laser controller, 2322, and a laser, 2324, such that when the connection, 2320, is open a laser trigger signal, 2326, is interrupted. In some embodiments, the laser controller, 2322, further comprises a clearing system, 2328, which unlatches the latch, 2318, in between laser pulses. FIG. 23B shows the laser signal, 2302, with a vertical axis, 2330, representing a peak power. FIG. 23B also shows the first comparator signal, 2308, the second comparator signal, 2314, and the laser trigger signal, 2326, all on a common horizontal axis, 2332, representing time. According to some embodiments, the laser signal, 2302, is integrated over time to provide an energy signal, 2334. The energy signal, 2334, can be used in a similar circuit to interrupt the laser trigger signal, 2326, once the energy signal reaches a prescribed pulse energy threshold. Additionally in some embodiments, the energy signal, 2326, is used to measure a total energy per pulse.

Figure 24:
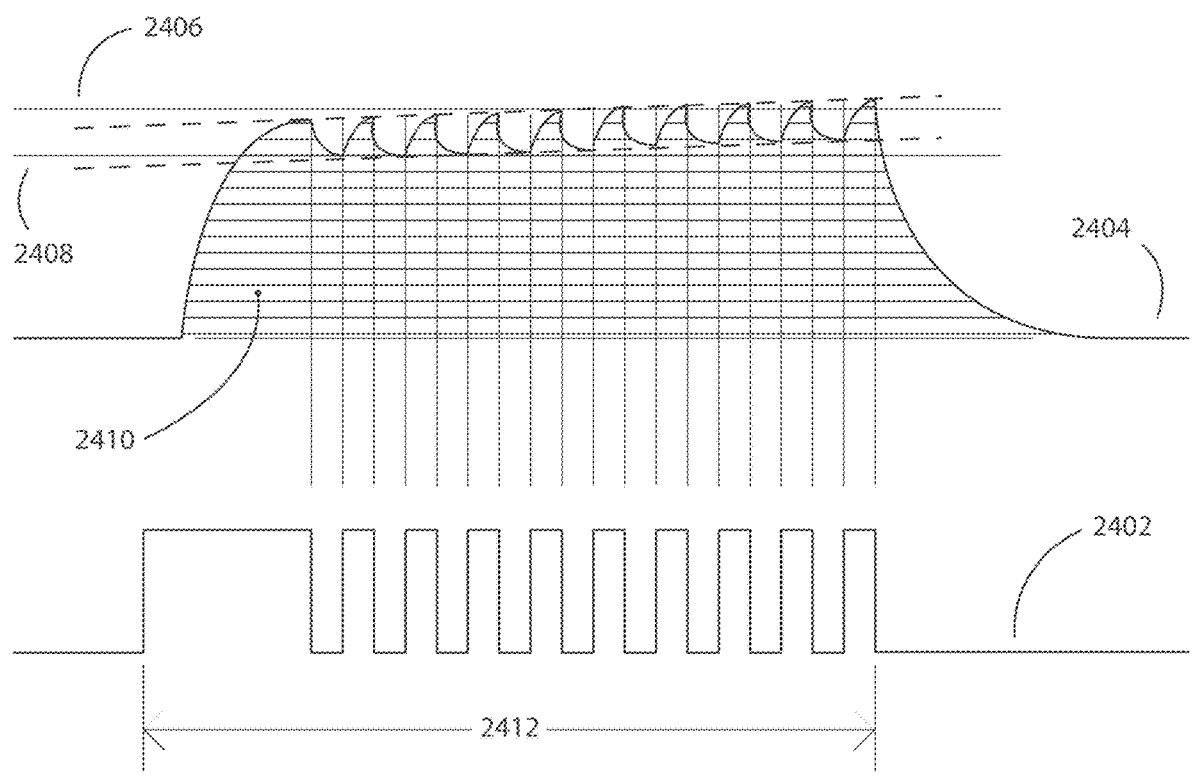

FIG. 24 depicts performance of still another embodiment employing an integrated laser sensor. The embodiment described in reference to FIG. 24 is similar to that of FIG. 23A, but without the latch, 2418, after the and-gate, 2416. According to this embodiment, a laser trigger signal, 2402, is not permanently interrupted once a laser signal, 2404, exceeds a maximum power threshold, 2406. Instead, the laser trigger signal, 2402, is momentarily interrupted, and after a hysteresis period, 2408, the laser trigger signal is uninterrupted. The result of this mode of operation is a laser signal, 2404, that is limited in height (power) according to the maximum power threshold. As described above, the laser signal, 2404, may be integrated to provide a measured pulse energy, 2410. According to some embodiments, a total pulse duration, 2412, of the trigger signal, 2402, is controlled according to the measured pulse energy.

An axiomatic design decomposition for a preventative laser treatment system and method is outlined below in Table 7. Additional system constraints may further influence the design. For example, Coherent E-150i lasers typically must be operated with an optical pulse duration of 5 microseconds or greater.

TABLE 7

Axiomatic Design Decomposition

| Functional Requirements (FR's) | | [FR] Design Range | Design Parameters (DP's) | |
|---|---|---|---|---|
| FR0 | Irradiate teeth to provide Acid Dissolution Resistance (ADR) | >75% Resistance to Acid | DP0 | Preventative Laser Treatment |
| FR1 | Prevent pulpal temperature rise | Less than 5.5 C | DP1 | Balance bulk heat load |
| FR1.1 | Remove heat from laser | pulpal temp rise | DP1.1 | Air sheath |
| FR1.2 | Limit Heat into tooth | | DP1.2 | Laser rep rate selected so that: Average power <~0.7 W |
| FR2 | Prevent melting from multiple laser pulses | No Visible melt at 200X Magnification with BF lighting | DP2 | Period between consecutive pulses acting on the same location greater than a cooling period threshold |
| FR3 | Prevent melting during a single laser pulse | No Visible melt at 200X Magnification with BF lighting | DPS | Focused beam size selected so that: max. local fluence is below upper threshold |
| FR4 | Cover the surface of the tooth evenly with laser pulse locations | Carbonate removed as a function of spacing within 25% maximum value | DP4 | Scanned laser pattern having a spacing between locations |

TABLE 7-continued

Axiomatic Design Decomposition

| Functional Requirements (FR's) | | [FR] Design Range | Design Parameters (DP's) | |
|---|---|---|---|---|
| FR5 | Heat a location of the tooth to a therapeutic range during | 400C > T > 1200 C. | DP5 | Pulse duration calibrated to produce a therapeutic beam width greater than the spacing |
| FR6 | Distinguish between treated and untreated surfaces | Sufficient for clinical treatment | DP6 | Disclosing solution |

A coupling matrix of the laser treatment (DP0) is shown below:

$$\begin{Bmatrix} FR1 \\ FR1.1 \\ FR1.2 \\ FR2 \\ FR3 \\ FR4 \\ FR5 \\ FR6 \end{Bmatrix} = \begin{bmatrix} X & 0 & 0 & 0 & 0 & 0 & 0 & 0 \\ 0 & X & 0 & 0 & 0 & 0 & 0 & 0 \\ 0 & 0 & X & 0 & 0 & 0 & 0 & 0 \\ 0 & 0 & X & X & 0 & 0 & 0 & 0 \\ 0 & 0 & 0 & 0 & X & 0 & 0 & 0 \\ 0 & 0 & 0 & 0 & X & X & 0 & 0 \\ 0 & 0 & 0 & 0 & X & X & X & 0 \\ 0 & 0 & 0 & 0 & 0 & 0 & 0 & X \end{bmatrix} \begin{Bmatrix} DP1 \\ DP1.1 \\ DP1.2 \\ DP2 \\ DP3 \\ DP4 \\ DP5 \\ DP6 \end{Bmatrix}$$

Having described herein illustrative embodiments, persons of ordinary skill in the art will appreciate various other features and advantages of the invention apart from those specifically described above. It should therefore be understood that the foregoing is only illustrative of the principles of the invention, and that various modifications and additions can be made by those skilled in the art without departing from the spirit and scope of the invention. Accordingly, the appended claims shall not be limited by the particular features that have been shown and described, but shall be construed also to cover any obvious modifications and equivalents thereof.

What is claimed is:

1. A method of treating a dental hard tissue to resist acid dissolution by decreasing surface carbonate, the method comprising the steps of:
   generating by using a $CO_2$ laser at least one pulse of a pulsed laser beam having a wavelength in a range from 8 to 12 microns and a pulse duration selected from a range of 0.1 to 100 microseconds;
   defining a laser beam width of the pulsed laser beam and focusing the pulsed laser beam at or near a surface of the dental hard tissue using at least one optic;
   controlling pulse energy of the pulsed laser beam based on the defined beam width, such that the at least one pulse of the pulsed laser beam has a fluence profile at a focus having:
      a maximum local fluence less than an upper threshold fluence, the upper threshold fluence defined as a minimum fluence that causes a surface modification of the dental hard tissue, wherein the maximum local fluence is insufficient to cause surface modification comprising each of melting and ablation, and
      at least one other local fluence greater than a lower threshold fluence, the lower threshold fluence defined as a fluence that causes a minimum decrease in an amount of surface carbonate of the dental hard tissue;
   using a beam guidance system disposed down beam of the at least one optic to:
      (i) direct a first laser pulse of the at least one pulse of the pulsed laser beam to an initial location within a treatment region at or near the surface of the dental hard tissue, such that a surface temperature of the initial location is raised from an initial surface temperature to a raised surface temperature during the first laser pulse, the raised temperature being below an upper temperature threshold defined as a minimum temperature that causes surface modification of the dental hard tissue;
      (ii) thereafter, direct one or more intermediate laser pulses of the at least one pulse of the pulsed laser beam generated by the laser to one or more intermediate locations within the treatment region at or near the surface of the dental hard tissue; and
      (iii) after (i) and (ii), direct another laser pulse of the at least one pulse of the pulsed laser beam to the initial location; and
   thereafter, applying a post-treatment solution to the dental hard tissue.

2. The method of claim 1, wherein the melting is determined by a visual inspection of a treated surface at least one of 200×, 500×, and 1000× magnification.

3. The method of claim 1, wherein the ablation is determined by a visual inspection of a treated surface at least one of 200×, 500×, and 1000× magnification.

4. The method of claim 1, wherein the acid dissolution resistance is determined by at least one of an acidic challenge and a pH cycling study.

5. The method of claim 4, wherein the acidic challenge comprises using at least one of citric acid, acetic acid, and lactic acid.

6. The method of claim 1, wherein the amount of surface carbonate is measured by at least one of reflectance FTIR, FTIR-ATR, Ramen Spectroscopy, and XRD.

7. The method of claim 1, wherein the fluence profile further comprises at least one of a Gaussian profile, a near-Gaussian profile, and a top-hat profile.

8. The method of claim 1, wherein controlling the pulse energy comprises controlling at least one of a pulse duration, average laser input power, and average laser output power.

9. The method of claim 1, wherein the post-treatment solution comprises at least one of hydrogen peroxide, fluoride, chitosan, xylitol, calcium, and phosphate.

10. The method of claim 1, wherein the laser pulse comprises a pulse energy in a range from 0.05 and 100 mJ.

11. The method of claim 1, wherein the location comprises a width in a range from 0.1 to 10 millimeters.

12. The method of claim 1, further comprising directing a fluid to flow at least one of onto and across the dental hard tissue.

13. The method of claim 12, wherein the fluid comprises at least one of air, nitrogen, and water.

14. The method of claim 12, wherein the fluid comprises a liquid.

15. The method of claim 12, wherein the fluid comprises fluoride.

16. The method of claim 12, wherein the fluid comprises a compressible fluid and the method further comprises expanding the fluid prior to directing the fluid upon the dental hard tissue.

17. The method of claim 12, wherein the directing the fluid step is asynchronous with the generating the laser pulse step.

18. The method of claim 12, wherein the directing the fluid step occurs during the generating the laser pulse step.

19. The method of claim 12, further comprising adjusting a flow rate of the fluid sufficient to decrease the surface temperature of the location to a lowered temperature while no pulse burst is directed toward the location, wherein a sum of the lowered temperature and the temperature increase amount is at most equal to the raised temperature.

20. The method of claim 19, wherein:
the fluid comprises compressed air; and
the flow rate is in a range from 1 SLPM to 100 SLPM.

21. The method of claim 12, wherein the directing the fluid step comprises generating a negative pressure differential that causes the fluid to flow across the dental hard tissue.

22. The method of claim 12, wherein the post-treatment solution comprises at least one of hydrogen peroxide, fluoride, chitosan, xylitol, calcium, and phosphate.

23. The method of claim 1, wherein the post-treatment solution comprises fluoride.

* * * * *